US010273299B2

(12) United States Patent
Frankel et al.

(10) Patent No.: US 10,273,299 B2
(45) Date of Patent: Apr. 30, 2019

(54) ANTIBODIES TO TUMOR ENDOTHELIAL MARKER 8

(71) Applicant: SCOTT & WHITE HEALTHCARE, Temple, TX (US)

(72) Inventors: Arthur E. Frankel, Temple, TX (US); Yunpeng Su, Katy, TX (US); Brad St. Croix, Frederick, MD (US); Stephen H. Leppla, Bethesda, MD (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/090,058

(22) Filed: Apr. 4, 2016

(65) Prior Publication Data
US 2016/0319016 A1 Nov. 3, 2016

Related U.S. Application Data

(62) Division of application No. 13/884,899, filed as application No. PCT/US2011/060583 on Nov. 14, 2011, now Pat. No. 9,309,322.

(60) Provisional application No. 61/527,339, filed on Aug. 25, 2011, provisional application No. 61/412,999, filed on Nov. 12, 2010.

(51) Int. Cl.
| A61K 39/395 | (2006.01) |
| C07K 16/28 | (2006.01) |
| A61K 9/00 | (2006.01) |
| A61K 45/06 | (2006.01) |
| A61K 47/68 | (2017.01) |

(52) U.S. Cl.
CPC ............ *C07K 16/28* (2013.01); *A61K 9/0019* (2013.01); *A61K 39/39558* (2013.01); *A61K 45/06* (2013.01); *A61K 47/6809* (2017.08); *A61K 47/6811* (2017.08); *A61K 47/6849* (2017.08); *A61K 47/6851* (2017.08); *C07K 2317/24* (2013.01); *C07K 2317/33* (2013.01); *C07K 2317/35* (2013.01); *C07K 2317/56* (2013.01); *C07K 2317/622* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| 5,530,101 | A | 6/1996 | Queen et al. ............... 530/387.3 |
| 5,550,246 | A | 8/1996 | Nicolaou et al. ............. 546/300 |
| 5,635,483 | A | 6/1997 | Pettit et al. ................... 514/19.3 |
| 5,663,149 | A | 9/1997 | Pettit et al. ................... 514/19.3 |
| 5,714,586 | A | 2/1998 | Kunstmann et al. ....... 530/391.7 |
| 5,739,116 | A | 4/1998 | Hamann et al. ................ 514/25 |
| 5,780,588 | A | 7/1998 | Pettit et al. .................... 530/330 |
| 6,441,163 | B1 | 8/2002 | Chari et al. .................... 540/458 |
| 7,374,762 | B2 | 5/2008 | Amphlett et al. ......... 424/184.1 |
| 7,494,649 | B2 | 2/2009 | Amphlett et al. ......... 424/133.1 |
| 7,501,120 | B2 | 3/2009 | Amphlett et al. ......... 424/133.1 |
| 7,511,121 | B2 | 3/2009 | Arnason et al. ............ 530/387.1 |
| 7,514,080 | B2 | 4/2009 | Amphlett et al. ......... 424/133.1 |
| 7,964,566 | B2 | 6/2011 | Doronina et al. ............ 514/19.3 |
| 9,181,340 | B2 * | 11/2015 | St. Croix ............... C07K 16/28 |
| 9,765,142 | B2 * | 9/2017 | Dimitrov ................ C07K 16/28 |
| 2003/0109682 | A1 | 6/2003 | Santi et al. ................ 530/391.1 |
| 2003/0220287 | A1 * | 11/2003 | Phillips .............. C12N 15/1137 514/44 A |
| 2004/0192900 | A1 | 9/2004 | Kunz et al. ................. 530/391.1 |
| 2005/0036942 | A1 | 2/2005 | Devaux et al. .............. 424/1.49 |
| 2006/0002942 | A1 | 1/2006 | Kunz et al. ................. 424/178.1 |
| 2007/0213511 | A1 | 9/2007 | Kunz et al. ................. 530/391.1 |
| 2008/0138898 | A1 | 6/2008 | Zhou et al. .................... 435/375 |
| 2009/0105461 | A1 | 4/2009 | Kunz et al. ................. 530/391.9 |
| 2009/0221094 | A1 | 9/2009 | Arnaout et al. .............. 436/501 |
| 2009/0304728 | A1 * | 12/2009 | Concetti ............. C12Q 1/6886 424/185.1 |
| 2009/0324491 | A1 | 12/2009 | Aburatani et al. ........... 424/1.49 |
| 2010/0209439 | A1 | 8/2010 | Yoshida ...................... 424/174.1 |
| 2011/0020343 | A1 | 1/2011 | Senter et al. ............... 424/134.1 |
| 2017/0114133 | A1 * | 4/2017 | Saha ....................... C07K 16/28 |

FOREIGN PATENT DOCUMENTS

| CN | 101 591 395 | 7/2009 |
| WO | WO 2002/010217 | 2/2002 |

(Continued)

OTHER PUBLICATIONS

Ruan et al. DNA Vaccine Against Tumor Endothelial Marker 8 Inhibits Tumor Angiogenesis and Growth. (J Immunother 2009;32: 486-491. (Year: 2009).*
Duan et al. Antitumor Activities of TEM8-Fc: An Engineered Antibody-like Molecule Targeting Tumor Endothelial Marker 8. J Natl Cancer Inst 2007;99: 1551-5. (Year: 2007).*
Fernando et al. Targeting Tumor Endothelial Marker 8 in the Tumor Vasculature of Colorectal Carcinomas in Mice. Cancer Res 2009; 69: (12). Jun. 15, 2009. (Year: 2009).*
Owen et al. The genetic engineering of monoclonal antibodies. J Immunol Methods. 168(2):149-165, 1994. (Year: 1994).*

(Continued)

*Primary Examiner* — Maher M Haddad
(74) *Attorney, Agent, or Firm* — Norton Rose Fulbright US LLP

(57) ABSTRACT

The present invention is directed to particular antibodies and fragments thereof that find use in the detection, prevention and treatment of diseases and disorders associated with abnormal angiogenesis. In particular, these antibodies detect tumor endothelial marker 8 (TEM8) in its native and cell-surface expressed form. Also disclosed are improved methods for producing monoclonal antibodies, as well as pharmaceutical compositions and kits.

23 Claims, 20 Drawing Sheets
Specification includes a Sequence Listing.

(56) References Cited

FOREIGN PATENT DOCUMENTS

| WO | WO 2005/048943 | 6/2005 |
|---|---|---|
| WO | WO 2012/174160 | 12/2012 |

OTHER PUBLICATIONS

Fernando et al. Specific Disruption of Tumor Vessels by Targeting TEM8. Molecular Therapy vol. 17, Supplement 1, May 2009. Abstract No. 787 (Year: 2009).*
Abi-Habib RJ, Singh R, Leppla SH, Green JJ, Ding Y, et al. (2006) "Systemic anthrax lethal toxin therapy produces regressions of subcutaneous human melanoma tumors in athymic nude mice." Clin Cancer Res 12: 7437-7443.
Bell SE, et al., (2001) "Differential gene expression during capillary morphogenesis in 3D collagen matrices: Regulated expression of genes involved in basement membrane matrix assembly, cell cycle progression, cellular differentiation and G-protein signaling." Journal Cell Sci 114:2755-2773.
Bradley, Kenneth, et al., "Identification of the cellular receptor for anthrax toxin." Nature 414, 225-229 (Nov. 8, 2001).
Brown et al., "Tolerance of single, but not multiple, amino acid replacements in antibody VH CDR 2: a means of minimizing B cell wastage from somatic hypermutation?" *J Immuno.*, 3285-91, 1996.
Carson-Walter, E. B., Watkins, D. N., Nanda, A., Vogelstein, B., Kinzler, K. W., St. Croix, B. Cell surface tumor endothelial markers are conserved in mice and humans. Cancer Res. 61: 6649-6655, 2001.
Chen, Kuang-Hua et al., "Selection of Anthrax Toxin Protective Antigen Variants That Discriminate between the Cellular Receptors TEM8 and CMG2 and Achieve Targeting of Tumor Cells." Journal of Biological Chemistry; 2007 282: 9834-9845. First Published on Jan. 24, 2007.
Cuesta, et al., "Multivalent Antibodies: When Design Surpasses Evolution." Trends in Biotechnology. Epub May 4, 2001. 28(7): 355-362, p. 356.
Cullen M, Seaman S, Chaudhary A, Yang MY, Hilton MB, Logsdon D, Haines DC, Tessarollo L, St Croix B. Host-derived tumor endothelial marker 8 promotes the growth of melanoma. Cancer Res. 2009;69:6021-6026.
Duan, et al., "Antitumor Activities of TEM8-Fc: An Engineered Antibody-like Molecule Targeting Tumor Endothelial Marker 8." Journal of the National Cancer Institute, 99(20): 1551-1555; 2007.
Duesbery NS, Resau J, Webb CP, Koochekpour S, Koo HM, Leppla SH et al. (2001). Suppression of ras-mediated transformation and inhibition of tumor growth and angiogenesis by anthrax lethal factor, a proteolytic inhibitor of multiple MEK pathways. Proc Natl Acad Sci USA 98: 4089-4094.
Felicetti et al., "Tumor endothelial marker 8 enhances tumor immunity in conjunction with immunization against differentiation Ag." Cytotherapy, vol. 9, No. 1, 23-24. 2007.
Frankel et al., "Tissue Distribution of Breast Cancer-Associated Antigens Defined by Monoclonal Antibodies", J. Biol. Resp. Modifiers 4:273-286 (1985).
Fu, et al., "The Structure of Tumor Endothelial Marker 8 (TEM8) Extracellular Domain and Implications for its Receptor Function for Recognizing Anthrax Toxin," PLoS One. 5(6): e11203. Jun. 18, 2010.
Go M.Y., Chow E.M., Mogridge J. The cytoplasmic domain of anthrax toxin receptor 1 affects binding of the protective antigen. Infect. Immun. 2009;77:52-59.
Hotchkiss, K. A., Basile, C. M., Spring, S. C., Bonuccelli, G., Lisanti, M. P. & Terman, B. I. (2005). Exp. Cell Res. 305, 133-144.
Ikeda H, Hideshima T, Fulciniti M, Lutz RJ, Yasui H, Okawa Y, et al. "The monoclonal antibody nBT062 conjugated to cytotoxic Maytansinoids has selective cytotoxicity against CD138-positive multiple myeloma cells in vitro and in vivo." Clin Cancer Res. 2009;15:4028-4037.
Liu S, Wang H, Currie BM, Molinolo A, Leung HJ, Moayeri M et al. Matrix metalloproteinase-activated anthrax lethal toxin demonstrates high potency in targeting tumor vasculature. J Biol Chem 2008; 283: 529-540.
Nanda, et al., "TEM8 Interacts with the Cleaved C5 Domain of Collagen Alpha 3(VI)." Cancer Research, 64(3):817-820. 2004.
Paul, Fundamental Immunology, $3^{rd}$ Edition, pp. 292-295, 1993.
Phillips et al., "Targeting HER2-positive breast cancer with trastuzumab-DM1, an antibody-cytotoxic drug conjugate." 2008 Cancer Research 68, 9280.
Rouleau et al., "The systemic administration of lethal toxin achieves a growth delay of human melanoma and neuroblastoma xenografts: Assessment of receptor contribution" Int. J. Oncol., 32:739-748, 2008.
Ruan Z, Yang Z, Wang Y, Wang H, Chen Y, et al. (2009) DNA vaccine against tumor endothelial marker 8 inhibits tumor angiogenesis and growth. Journal of Immunotherapy 32: 486-491.
Shukla A. A., Thömmes J. 2010. "Recent advances in large-scale production of monoclonal antibodies and related proteins." Trends in Biotechnology 28:253-261.
St Croix et al., "Genes expressed in human tumor endothelium." Science, 289:1197-1202, 2000.
Vajdos et al., "Comprehensive functional maps of the antigen-binding site of an anti-ErbB2 antibody obtained with shotgun scanning mutagenesis", *J Mol Biol.*, 320(2): 415-28, 2002.
Watson LE, Kuo SR, Katki K, Dang T, Park SK, Dostal DE, et al. Anthrax toxins induce shock in rats by depressed cardiac ventricular function PLoS ONE. 2007a;2:e466.
Werner E., Kowalczyk A.P., Faundez V. Anthrax toxin receptor 1/tumor endothelium marker 8 mediates cell spreading by coupling extracellular ligands to the actin cytoskeleton. J. Biol. Chem. 2006;281:23227-23236.
Yang, et al., "The Cell Surface Structure of Tumor Endothelial Marker 8 (TEM8) is Regulated by the Actin Cytoskeleton." Biochim Biophys Acta. ePub 1813(1):39-49. Dec. 1, 2010.

* cited by examiner

*Characterization and partial epitope mapping of SB antibodies.*

| Anti-TEM8 antibody | Isotype | Reactivity | | | Region of epitope |
|---|---|---|---|---|---|
| | | hCMG2 | hTEM8 | mTEM8 | |
| SB2 | IgG2a, | − | + | + | aa 82 to 145 |
| SB4 | IgG2a, | − | + | + | aa 82 to 145 |
| SB5 | IgG1, | − | + | + | aa 82 to 145 |
| SB8 | IgG1, | − | + | − | aa 268 to 320 |
| SB12 | IgG1, | − | + | + | aa 82 to 145 |

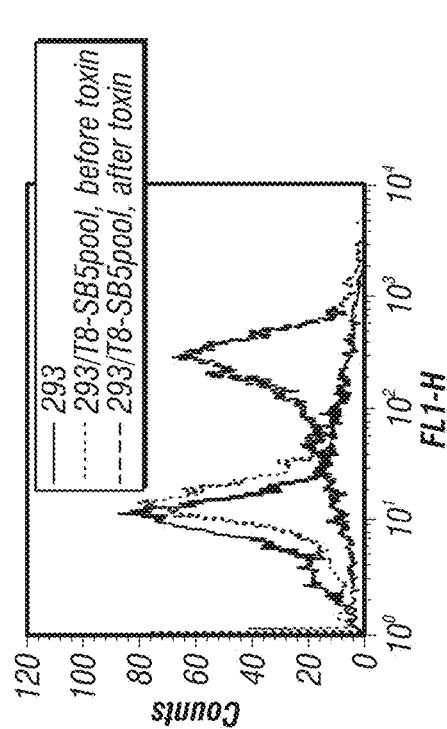
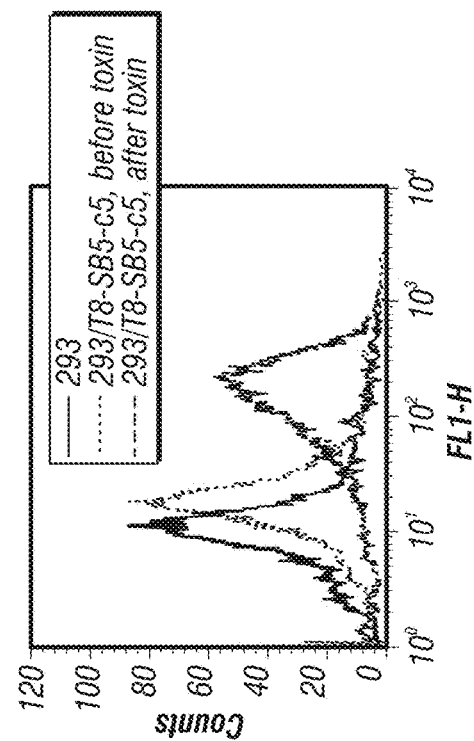
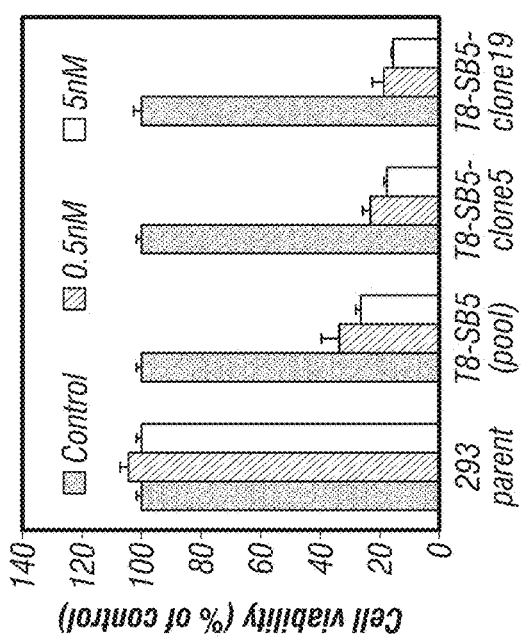
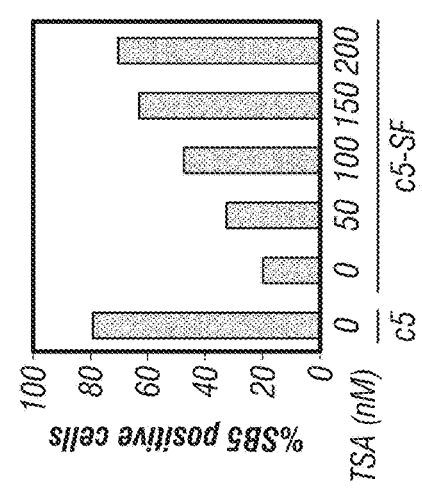
FIG. 3A
FIG. 3B
FIG. 3C

Plasmid #1: pAN6525-VL (9202 bases) for light chain expression

```
CTCTCAGTACAATCTGCTCTGATGCCGCATAGTTAAGCCAGTATCTGCTCCCTGCTTGTGTGTTGGAGGTCGCTGAGTAGT
GCGCGAGCAAAATTTAAGCTACAACAAGGCAAGGCTTGACCGACAATTGCATGAAGAATCTGCTTAGGGTTAGGCGTTTTG
CGCTGCTTCGCGATGTACGGGCCAGATATACGCGTTGACATTGATTATTGACTAGTTATTAATAGTAATCAATTACGGGGT
CATTAGTTCATAGCCCATATATGGAGTTCCGCGTTACATAACTTACGGTAAATGGCCCGCCTGGCTGACCGCCCAACGA
CCCCCGCCCATTGACGTCAATAATGACGTATGTTCCCATAGTAACGCCAATAGGGACTTTCCATTGACGTCAATGGGTG
GAGTATTTACGGTAAACTGCCCACTTGGCAGTACATCAAGTGTATCATATGCCAAGTACGCCCCCTATTGACGTCAATGA
CGGTAAATGGCCCGCCTGGCATTATGCCCAGTACATGACCTTATGGGACTTTCCTACTTGGCAGTACATCTACGTATTAG
TCATCGCTATTACCATGGTGATGCGGTTTTGGCAGTACATCAATGGGCGTGGATAGCGGTTTGACTCACGGGGATTTCC
AAGTCTCCACCCCATTGACGTCAATGGGAGTTTGTTTTGGCACCAAAATCAACGGGACTTTCCAAAATGTCGTAACAACT
CCGCCCCATTGACGCAAATGGGCGGTAGGCGTGTACGGTGGGAGGTCTATATAAGCAGAGCTCTCTGGCTAACTAGAG
AACCCACTGCTTACTGGCTTATCGAAATTAATACGACTCACTATAGGGAGACCCAAGCTGGCTAGCGTTTAAACTTAAGCTT
GGTACCGAGCTCGGATCCACTAGTCCAGTGTGGTGGAATTCTGCAGATATCCACCATGGATTTTCAAGGGCAGATTTTCA
GCCTCCTGCTAATCAGTATCACAGTCATAGTGTCCAGTGGAGACATTGTGATGACCCAGACTCCACCCTCTGTACCTGTC
ACTCCTGGAGAGTCAGTATCCATCTCCTGCAGGTCTAGTAAGAGTCTCCTGCATAGTAATGGCAACACTTACTTGTATTG
GTTCCTGCAGAGGCCAGGCCAGTCTCCTCAGCTCCTGATATATCGGATGTCCAACCTTGCCTCAGGAGTCCCAGACAGG
TTCAGTGGCAGTGGGTCAGGAACTGCTTTCACACTGAGAATCAGTAGAGTGGAGGCTGAGGATGTGGGTGTTTATTACT
GTATGCAACATCTAGAATATCCATTCACGTTCGGCTCGGGGACAAAGTTGGAAATAAAACGTAAGTCGACTTTTCTCATC
TTTTTTATGTGTAAGACACAGGTTTCATGTTAGGAGTTAAAGTCAGTTCAGAAAATCTTGAGAAAATGGAGAGGGCTCATT
ATCAGTTGACGTGGCATACAGTGTCAGATTTTCTGTTTATCAAGCTAGTGAGATTAGGGGCAAAAAGAGGCTTTAGTTGAGA
GGAAAGTAATTAATACTATGGTCACCATCCAAGAGATTGGATCGGAGAATAAGCATGAGTAGTTATTGAGATCTGGGTCTG
ACTGCAGGTAGCGTGGTCTTCTAGACGTTTAAGTGGGAGATTTGGAGGGGATGAGGAATGAAGGAACTTCAGGATAGAAA
AGGGCTGAAGTCAAGTTCAGCTCCTAAAATGGATGTGGGAGCAAACTTTGAAGATAAACTGAATGACCCAGAGGATGAAAC
AGCGCAGATCAAAGAGGGGCCTGGAGCTCTGAGAAGAGAAGGAGACTCATCCGTGTTGAGTTTCCACAAGTACTGTCTTG
AGTTTTGCAATAAAAGTGGGATAGCAGAGTTGAGTGAGCCGTAGGCTGAGTTCTCTCTTTTGTCTCCTAAGTTTTTATGACT
ACAAAAATCAGTGTATGTCCTGAATAATCATTAAGCTGTTTGAAAGTATGACTGCTTGCCATGTAGATACCATGGCTTGCT
GAATAATCAGAAGAGGTGTGACTCTTATTCTAAAATTTGTCACAAAATGTCAAAATGAGAGACTCTGTAGGAACGAGTCCTT
GACAGACAGCTCAAGGGGTTTTTTCCTTTGTCTCATTTCTACATGAAAGTAAATTTGAAATGATCTTTTTTATTATAAGAGTA
GAAATACAGTTGGGTTTGAACTATATGTTTTAATGGCCACGGTTTTGTAAGACATTTGGTCCTTTGTTTTCCCAGTTATTACT
CGATTGTAATTTTATATCGCCAGCAATGGACTGAAACGGTCCGCAACCTCTTCTTTACAACTGGGTGACCTCGCGGCTGTG
CCAGCCATTTGGCGTTCACCCTGCCGCTAAGGGCCATGTGAACCCCCGCGGTAGCATCCCTTGCTCCGCGTGGACCACTT
TCCTGAGGCACAGTGATAGGAACAGAGCCACTAATCTGAAGAGAACAGAGATGTGACAGACTACACTAATGTGAGAAAAAC
AAGGAAAGGGTGACTTATTGGAGATTTCAGAAATAAAATGCATTTATTATTATATTCCCTTATTTTAATTTTCTATTAGGGAAT
TAGAAAGGGCATAAACTGCTTTATCCAGTGTTATATTAAAAGCTTTTTTTTTTTCAGTGCTATTTAATTATTTCAATATCCTCTC
ATCAAATGTATTTAAATAACAAAAGCTCAACCAAAAAGAAAGAAATATGTAATTCTTTCAGAGTAAAAATCACACCCATGACC
TGGCCACTGAGGGCTTGATCAATTCACTTTGAATTTGGCATTAAATACCATTAAGGGTATATTAACTGATTTTAAAATAAGATA
TATTCGTGACCATGTTTTAACTTTCAAAAATGTAGCTGCCAGTGTGTGATTTTATTTCAGTTGTACAAAATATCTAAACCTAT
AGCAATGTGATTAATAAAAAACTTAAACATATTTTCCAGTACCCTTAATTCTGTGATAGGAAAATTTAATCTGAGTATTTAATTT
CATAATCTCTAAAATAGTTTAATGATTTGTCATTGTGTTGCTGTCGTTTACCCCAGCTGATCTCAAAGTGATATTTAAGGAG
ATTATTTGGTCTGCAACAACTTGATAGGACTATTTAGGGCCTTTTAAAGCTCTATTAAAACTAACTTACAACGATTCAAAA
CTGTTTTAAACTATTTCAAAATGATTTAGAGCCTTTTGAAAACTCTTTAAACACTTTTAAACTCTATTAAAACTAATAAGAT
AACTTGAAATAATTTTCATGTCAAATACATTAACTGTTAATGTTTAAATGCCAGATGAAAAATGTAAAGCTATCAAGAATTCA
CCCAGATAGGAGTATCTTCATAGCATGTTTTTCCCTGCTTATTTTCCAGTGATCACATTATTTTGCTACCATGGTTATTTTATA
CAATTATCTGAAAAAAATTAGTTATGAAGATTAAAAGAGAAGAAAATATTAAACATAAGAGATTCAGTCTTTCATGTTGAACT
GCTTGGTTAACAGTGAAGTTAGTTTTAAAAAAAAAAAAAACTATTTCTGTTATCAGCTGACTTCTCCCTATCTGTTGACTTCT
CCCAGCAAAAGATTCTTATTTTACATTTTAACTACTGCTCTCCCACCCAACGGGTGGAATCCCCAGAGGGGGATTTCCAA
GAGGCCACCTGGCAGTTGCTGAGGGTCAGAAGTGAAGCTAGCCACTTCCTCTTAGGCAGGTGGCCAAGATTACAGTTGAC
CTCTCCTGGTATGGCTGAAAATTGCTGCATATGGTTACAGGCCTTGAGGCCTTTGGGAGGGCTTAGAGAGTTGCTGGAAC
AGTCAGAAGGTGGAGGGGCTGACACCACCCAGGCGCAGAGGCAGGGCTCAGGGCCTGCTCTGCAGGGAGGTTTTAGCC
CAGCCCAGCCAAAGTAACCCCCGGGAGCCTGTTATCCCAGCACAGTCCTGGAAGAGGCACAGGGGAAATAAAAGCGGAC
```

*FIG. 6*

```
GGAGGCTTTCCTTGACTCAGCCGCTGCCTGGTCTTCTTCAGACCTGTTCTGAATTCTAAACTCTGAGGGGGTCGGATGACG
TGGCCATTCTTTGCCTAAAGCATTGAGTTTACTGCAAGGTCAGAAAAGCATGCAAAGCCCTCAGAATGGCTGCAAAGAGCT
CCAACAAAACAATTTAGAACTTTATTAAGGAATAGGGGGAAGCTAGGAAGAAACTCAAAACATCAAGATTTTAAATACGCTT
CTTGGTCTCCTTGCTATAATTATCTGGGATAAGCATGCTGTTTTCTGTCTGTCCCTAACATGCCCTGTGATTATCCGCAAAC
AACACACCCAAGGGCAGAACTTTGTTACTTAAACACCATCCTGTTTGCTTCTTTCCTCAGGAACTGTGGCTGCACCATCTGT
CTTCATCTTCCCGCCATCTGATGAGCAGTTGAAATCTGGAACTGCCTCTGTTGTGTGCCTGCTGAATAACTTCTATCCCAGA
GAGGCCAAAGTACAGTGGAAGGTGGATAACGCCCTCCAATCGGGTAACTCCCAGGAGAGTGTCACAGAGCAGGACAGCA
AGGACAGCACCTACAGCCTCAGCAGCACCCTGACGCTGAGCAAAGCAGACTACGAGAAACACAAAGTCTACGCCTGCGAA
GTCACCCATCAGGGCCTGAGCTCGCCCGTCACAAAGAGCTTCAACAGGGGAGAGTGTTAGAGGGAGAAGTGCCCCCACC
TGCTCCTCAGTTCCAGCCTGACCCCTCCCATCCTTTGGCCTCTGACCCTTTTCCACAGGGGAAACCGCTGATCAGCCTC
GACTGTGCCTTCTAGTTGCCAGCCATCTGTTGTTTGCCCCTCCCCGTGCCTTCCTTGACCCTGGAAGGTGCCACTCCCAC
TGTCCTTTCCTAATAAAATGAGGAAATTGCATCGCATTGTCTGAGTAGGTGTCATTCTATTCTGGGGGGTGGGGTGGGGCA
GGACAGCAAGGGGGAGGATTGGCAAGACAATAGCAGGCATGCTGGGGATGCGGTGGGCTCTATGGCTTCTGAGGCGGA
AAGAACCAGCTGGGGCTCTAGGGGGTATCCCCACGCGCCCTGTAGCGGCGCATTAAGCGCGGCGGGTGTGGTGGTTAC
GCGCAGCGTGACCGCTACACTTGCCAGCGCCCTAGCGCCCGCTCCTTTCGCTTTCTTCCCTTCCTTTCTCGCCACGTTCG
CCGGCTTTCCCCGTCAAGCTCTAAATCGGGGGCTCCCTTTAGGGTTCCGATTTAGTGCTTTACGGCACCTCGACCCCAAAA
AACTTGATTAGGGTGATGGTTCACGTAGTGGGCCATCGCCCTGATAGACGGTTTTTCGCCCTTTGACGTTGGAGTCCACGT
TCTTTAATAGTGGACTCTTGTTCCAAACTGGAACAACACTCAACCCTATCTCGGTCTATTCTTTTGATTTATAAGGGATTTTG
```

*FIG. 6 (Cont'd)*

```
CCGATTTCGGCCTATTGGTTAAAAAATGAGCTGATTTAACAAAAATTTAACGCGAATTAATTCTGTGGAATGTGTGTCAGTTA
GGGTGTGGAAAGTCCCCAGGCTCCCCAGCAGGCAGAAGTATGCAAAGCATGCATCTCAATTAGTCAGCAACCAGGTGTGG
AAAGTCCCCAGGCTCCCCAGCAGGCAGAAGTATGCAAAGCATGCATCTCAATTAGTCAGCAACCATAGTCCCGCCCCTAA
CTCCGCCCATCCCGCCCCTAACTCCGCCCAGTTCCGCCCATTCTCCGCCCCATGGCTGACTAATTTTTTTTATTTATGCAG
AGGCCGAGGCCGCCTCTGCCTCTGAGCTATTCCAGAAGTAGTGAGGAGGCTTTTTTGGAGGCCTAGGCTTTTGCAAAAAG
CTCCCGGGAGCTTGTATATCCATTTTCGGATCTGATCAAGAGACAGGATGAGGATCGTTTCGCATGATTGAACAAGATGGA
TTGCACGCAGGTTCTCCGGCCGCTTGGGTGGAGAGGCTATTCGGCTATGACTGGGCACAACAGACAATCGGCTGCTCTGA
TGCCGCCGTGTTCCGGCTGTCAGCGCAGGGGCGCCCGGTTCTTTTTGTCAAGACCGACCTGTCCGGTGCCCTGAATGAA
CTGCAGGACGAGGCAGCGCGGCTATCGTGGCTGGCCACGACGGGCGTTCCTGCGCAGCTGTGCTCGACGTTGTCACTG
AAGCGGGAAGGGACTGGCTGCTATTGGGCGAAGTGCCGGGCAGGATCTCCTGTCATCTCACCTTGCTCCTGCCGAGAA
AGTATCCATCATGGCTGATGCAATGCGGCGGCTGCATACGCTTGATCCGGCTACCTGCCCATTCGACCACCAAGCGAAAC
ATCGCATCGAGCGAGCACGTACTCGGATGGAAGCCGGTCTTGTCGATCAGGATGATCTGGACGAAGAGCATCAGGGGCT
CGCGCCAGCCGAACTGTTCGCCAGGCTCAAGGCGCGCATGCCCGACGGCGAGGATCTCGTCGTGACCCATGGCGATGC
CTGCTTGCCGAATATCATGGTGGAAAATGGCCGCTTTTCTGGATTCATCGACTGTGGCCGGCTGGGTGTGGCGGACCGCT
ATCAGGACATAGCGTTGGCTACCCGTGATATTGCTGAAGAGCTTGGCGGCGAATGGGCTGACCGCTTCCTCGTGCTTTAC
GGTATCGCCGCTCCCGATTCGCAGCGCATCGCCTTCTATCGCCTTCTTGACGAGTTCTTCTGAGCGGGACTCTGGGGTTC
GAAATGACCGACCAAGCGACGCCCAACCTGCCATCACGAGATTTCGATTCCACCGCCGCCTTCTATGAAAGGTTGGGCTT
CGGAATCGTTTTCCGGGACGCCGGCTGGATGATCCTCCAGCGCGGGGATCTCATGCTGGAGTTCTTCGCCCACCCCAACT
TGTTTATTGCAGCTTATAATGGTTACAAATAAAGCAATAGCATCACAAATTTCACAAATAAAGCATTTTTTTCACTGCATTCTA
GTTGTGGTTTGTCCAAACTCATCAATGTATCTTATCATGTCTGTATACCGTCGACCTCTAGCTAGAGCTTGGCGTAATCATG
GTCATAGCTGTTTCCTGTGTGAAATTGTTATCCGCTCACAATTCCACACAACATACGAGCCGGAAGCATAAAGTGTAAAGCC
TGGGGTGCCTAATGAGTGAGCTAACTCACATTAATTGCGTTGCGCTCACTGCCCGCTTTCCAGTCGGGAAACCTGTCGTG
CCAGCTGCATTAATGAATCGGCCAACGCGCGGGGAGAGGCGGTTTGCGTATTGGGCGCTCTTCCGCTTCCTCGCTCACTG
ACTCGCTGCGCTCGGTCGTTCGGCTGCGGCGAGCGGTATCAGCTCACTCAAAGGCGGTAATACGGTTATCCACAGAATCA
GGGGATAACGCAGGAAAGAACATGTGAGCAAAAGGCCAGCAAAAGGCCAGGAACCGTAAAAAGGCCGCGTTGCTGGCGT
TTTTCCATAGGCTCCGCCCCCTGACGAGCATCACAAAAATCGACGCTCAAGTCAGAGGTGGCGAAACCCGACAGGACTA
TAAAGATACCAGGCGTTTCCCCCTGGAAGCTCCCTCGTGCGCTCTCCTGTTCCGACCCTGCCGCTTACCGGATACCTGTC
CGCCTTTCTCCCTTCGGGAAGCGTGGCGCTTTCTCATAGCTCACGCTGTAGGTATCTCAGTTCGGTGTAGGTCGTTCGCTC
CAAGCTGGGCTGTGTGCACGAACCCCCCGTTCAGCCCGACCGCTGCGCCTTATCCGGTAACTATCGTCTTGAGTCCAACC
CGGTAAGACACGACTTATCGCCACTGGCAGCAGCCACTGGTAACAGGATTAGCAGAGCGAGGTATGTAGGCGGTGCTACA
GAGTTCTTGAAGTGGTGGCCTAACTACGGCTACACTAGAAGAACAGTATTTGGTATCTGCGCTCTGCTGAAGCCAGTTACC
TTCGGAAAAAGAGTTGGTAGCTCTTGATCCGGCAAACAAACCACCGCTGGTAGCGGTGGTTTTTTTGTTTGCAAGCAGCAG
ATTACGCGCAGAAAAAAAGGATCTCAAGAAGATCCTTTGATCTTTTCTACGGGGTCTGACGCTCAGTGGAACGAAAACTCA
CGTTAAGGGATTTTGGTCATGAGATTATCAAAAAGGATCTTCACCTAGATCCTTTTAAATTAAAAATGAAGTTTTAAATCAAT
CTAAAGTATATATGAGTAAACTTGGTCTGACAGTTACCAATGCTTAATCAGTGAGGCACCTATCTCAGCGATCTGTCTATTT
CGTTCATCCATAGTTGCCTGACTCCCCGTCGTGTAGATAACTACGATACGGGAGGGCTTACCATCTGGCCCCAGTGCTGC
AATGATACCGCGAGACCCACGCTCACCGGCTCCAGATTTATCAGCAATAAACCAGCCAGCCGGAAGGGCCGAGCGCAGA
AGTGGTCCTGCAACTTTATCCGCCTCCATCCAGTCTATTAATTGTTGCCGGGAAGCTAGAGTAAGTAGTTCGCCAGTTAATA
GTTTGCGCAACGTTGTTGCCATTGCTACAGGCATCGTGGTGTCACGCTCGTCGTTTGGTATGGCTTCATTCAGCTCCGGTT
CCCAACGATCAAGGCGAGTTACATGATCCCCATGTTGTGCAAAAAAGCGGTTAGCTCCTTCGGTCCTCCGATCGTTGTCA
GAAGTAAGTTGGCCGCAGTGTTATCACTCATGGTTATGGCAGCACTGCATAATTCTCTTACTGTCATGCCATCCGTAAGATG
CTTTTCTGTGACTGGTGAGTACTCAACCAAGTCATTCTGAGAATAGTGTATGCGGCGACCGAGTTGCTCTTGCCCGGCGTC
AATACGGGATAATACCGCGCCACATAGCAGAACTTTAAAAGTGCTCATCATTGGAAAACGTTCTTCGGGGCGAAAACTCTC
AAGGATCTTACCGCTGTTGAGATCCAGTTCGATGTAACCCACTCGTGCACCCAACTGATCTTCAGCATCTTTTACTTTCACC
AGCGTTTCTGGGTGAGCAAAAACAGGAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGCGGATACATATTTGAATGTATTTAGAA
AAATAAACAAATAGGGGTTCCGCGCACATTTCCCCGAAAAGTGCCACCTGACG
```

FIG. 6 (Cont'd)

Plasmid #2: pAH6307-VH (9493 bases) for heavy chain expression

```
GATCTCCCGATCCCCTATGGTGCACTCTCAGTACAATCTGCTCTGATGCCGCATAGTTAAGCCAGTATCTGCTCCCTGCTT
GTGTGTTGGAGGTCGCTGAGTAGTGCGCGAGCAAAATTTAAGCTACAACAAGGCAAGGCTTGACCGACAATTGCATGAAG
AATCTGCTTAGGGTTAGGCGTTTTGCGCTGCTTCGCGATGTACGGGCCAGATATACGCGTTGACATTGATTATTGACTAGT
TATTAATAGTAATCAATTACGGGGTCATTAGTTCATAGCCCATATATGGAGTTCCGCGTTACATAACTTACGGTAAATGGCC
CGCCTGGCTGACCGCCCAACGACCCCCGCCCATTGACGTCAATAATGACGTATGTTCCCATAGTAACGCCAATAGGGACT
TTCCATTGACGTCAATGGGTGGAGTATTTACGGTAAACTGCCCACTTGGCAGTACATCAAGTGTATCATATGCCAAGTACG
CCCCCTATTGACGTCAATGACGGTAAATGGCCCGCCTGGCATTATGCCCAGTACATGACCTTATGGGACTTTCCTACTTGG
CAGTACATCTACGTATTAGTCATCGCTATTACCATGGTGATGCGGTTTTGGCAGTACATCAATGGGCGTGGATAGCGGTTT
GACTCACGGGGATTTCCAAGTCTCCACCCCATTGACGTCAATGGGAGTTTGTTTTGGCACCAAAATCAACGGGACTTTCCA
AAATGTCGTAACAACTCCGCCCCATTGACGCAAATGGGCGGTAGGCGTGTACGGTGGGAGGTCTATATAAGCAGAGCTCT
CTGGCTAACTAGAGAACCCACTGCTTACTGGCTTATCGAAATTAATACGACTCACTATAGGGAGACCCAAGCTGGCTAGAC
TCGAGCGGCCGCCACTGTGCTGGATATCCACCATGGGATGGAGCTGGGTCATCCTCTTTCTGGTAGCAACAGCTACAGG
TGTGCACTCCCAGGTCCAGCTGCAGCAGTCTGGGGCTGAGCTGGTGAGGCCTGGGGTCTCAGTGAAGATTTCCTGCAA
GGGTTCTGGCTACACATTCACTGATTATGCTATGCACTGGGTGAAGCAGAGTCATGCAAAGAGTCTAGAGTGGATTGGA
GTTATTAGTACTTACTTTGGTGATGCTACCTACAACCAGAAGTTCAAGGGCAAGGCCACAATGACTGTAGACAAATCCTC
CAGCACACGCTATATGGAACTTGCCAGACTGACATCTGAGGATTCTGCCATCTATTACTGTGCAAGAGAGGATTACGTC
CCGTTTGCTTACTGGGGCCAAGGGACTCTGGTCACTGTCTCTGCAGCTAGCACCAAGGGCCCATCGGTCTTCCCCCTGG
CACCCTCCTCCAAGAGCACCTCTGGGGGCACAGCGGCCCTGGGCTGCCTGGTCAAGGACTACTTCCCCGAACCGGTGA
CGGTGTCGTGGAACTCAGGCGCCCTGACCAGCGGCGTGCACACCTTCCCGGCTGTCCTACAGTCCTCAGGACTCTACT
CCCTCAGCAGCGTGGTGACCGTGCCCTCCAGCAGCTTGGGCACCCAGACCTACATCTGCAACGTGAATCACAAGCCCA
GCAACACCAAGGTGGACAAGAAAGTTGGTGAGAGGCCAGCACAGGGAGGGAGGGTGTCTGCTGGAAGCCAGGCTCAG
CGCTCCTGCCTGGACGCATCCCGGCTATGCAGCCCCAGTCCAGGGCAGCAAGGCAGGCCCCGTCTGCCTCTTCACCCGG
AGGCCTCTGCCCGCCCCACTCATGCTCAGGGAGAGGGTCTTCTGGCTTTTTCCCCAGGCTCTGGGCAGGCACAGGCTAG
GTGCCCCTAACCCAGGCCCTGCACACAAAGGGGCAGGTGCTGGGCTCAGACCTGCCAAGAGCCATATCCGGGAGGACCC
TGCCCCTGACCTAAGCCCACCCCAAAGGCCAAACTCTCCACTCCCTCAGCTCGGACACCTTCTCTCCTCCCAGATTCCAGT
AACTCCCAATCTTCTCTCTGCAGAGCCCAAATCTTGTGACAAAACTCACACATGCCCACCGTGCCCAGGTAAGCCAGCCC
AGGCCTCGCCCTCCAGCTCAAGGCGGGACAGGTGCCCTAGAGTAGCCTGCATCCAGGGACAGGCCCCAGCCGGGTGCT
GACACGTCCACCTCCATCTCTTCCTCAGCACCTGAACTCCTGGGGGGACCGTCAGTCTTCCTCTTCCCCCCAAAACCCAA
GGACACCCTCATGATCTCCCGGACCCCTGAGGTCACATGCGTGGTGGTGGACGTGAGCCACGAAGACCCTGAGGTCAAG
TTCAACTGGTACGTGGACGGCGTGGAGGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAGTACAAGTGCAAGGTCTCCAACAAAGCC
CTCCCAGCCCCCATCGAGAAAACCATCTCCAAAGCCAAAGGTGGGACCCGTGGGGTGCGAGGGCCACATGGACAGAGGC
CGGCTCGGCCCACCCTCTGCCCTGAGAGTGACCGCTGTACCAACCTCTGTCCCTACAGGGCAGCCCCGAGAACCACAGG
TGTACACCCTGCCCCCATCCCGGGATGAGCTGACCAAGAACCAGGTCAGCCTGACCTGCCTGGTCAAAGGCTTCTATCCC
AGCGACATCGCCGTGGAGTGGGAGAGCAATGGGCAGCCGGAGAACAACTACAAGACCACGCCTCCCGTGCTGGACTCCG
ACGGCTCCTTCTTCCTCTACAGCAAGCTCACCGTGGACAAGAGCAGGTGGCAGCAGGGGAACGTCTTCTCATGCTCCGTG
ATGCATGAGGCTCTGCACAACCACTACACGCAGAAGAGCCTCTCCCTGTCTCCGGGTAAATGAGTGCGACGGCCGGCAA
GCCCCCGCTCCCCGGGCTCTCGCGGTCGCACGAGGATGCTTGGCACGTACCCCCTGTACATACTTCCCGGGCGCCCAGC
ATGGAAATAAAGCACCCAGCGCTGCCCTGGGCCCCTGCGAGACTGTGATGGTTCTTTCCACGGGTCAGGCCGAGTCTGA
GGCCTGAGTGGCATGAGGGAGGCAGAGCGGGTCCCACTGTCCCACACTGGCCCAGGCTGTGCAGGTGTGCCTGGGCC
GCCTAGGGTGGGGCTCAGCCAGGGGCTGCCCTCGGCAGGGTGGGGGATTTGCCAGCGTGGCCCTCCCTCCAGCAGCAC
CTGCCCTGGGCTGGGCCACGGGAAGCCCTAGGAGCCCCTGGGGACAGACACACAGCCCCTGCCTCTGTAGGAGACTGT
CCTGTTCTGTGAGCGCCCTGTCCTCCGACCTCCATGCCCACTCGGGGCATGCCTAGTCCATGTGCGTAGGGACAGGCC
CTCCCTCACCCATCTACCCCCACGGCACTAACCCCTGGCTGCCCTGCCCAGCCTCGCACCCGCATGGGGACACAACCGA
CTCCGGGGACATGCACTCTCGGGCCCTGTGGAGGGACTGGTGCAGATGCCCACACACACACTCAGCCCAGACCCGTTCA
ACAAACCCCGCACTGAGGTTGGCCGGCCACACGGCCACCACACACACGTGCACGCCTCACACACGGAGCCTCACCCG
GGCGAACTGCACAGCACCCAGACCAGAGCAAGGTCCTCGCACACGTGAACACTCCTCGGACACAGGCCCCACGAGCCC
CACGCGGCACCTCAAGGCCCACGAGCCTCTCGGCAGCTTCTCCACATGCTGACCTGCTCAGACAAACCCAGCCCTCCTCT
CACAAGGGTGCCCCTGCAGCCGCCACACACACACAGGGGATCACACACCACGTCACGTCCCTGGCCCTGGCCCACTTCC
```

FIG. 7

```
CAGTGCCGCCCTTCCCTGCAGCTGCACCTCGGGGGCTCCCTGCATACGCCCCCCGCCTCCTGCAGCCACACGCATTGCC
CGAGCGACCCTCCCTGGCCCCTGTCGCTACATGGACCCCTGGGGCTTCTCCTCTTTTCTACATGGATGCAGTTTCTCCTCC
TGCTGGGCACGGTGCTGCCTGCCCTGGTCACTCTGCGGGGGACAGGGCCTCCAGGGAAAGCTGGGTCGAGGCTGGGAG
CTGGCTCAGACTGGCCAGGCAGAGCCACAGGGAGGGCCTTCCAGAACCAACCATGGTCCGAAGCGAGAGGTGGGTGTC
AGATCTGTGTGAGTCAGCTCAGGACCACAGCGGGGCGGCTCCCACGGCAGACATGGATCCACTAGAGGGCCCGTTTAAA
CCCGCTGATCAGCCTCGACTGTGCCTTCTAGTTGCCAGCCATCTGTTGTTTGCCCCTCCCCCGTGCCTTCCTTGACCCTGG
AAGGTGCCACTCCCACTGTCCTTTCCTAATAAAATGAGGAAATTGCATCGCATTGTCTGAGTAGGTGTCATTCTATTCTGGG
GGGTGGGGTGGGGCAGGACAGCAAGGGGGAGGATTGGGAAGACAATAGCAGGCATGCTGGGGATGCGGTGGGCTCTAT
GGCTTCTGAGGCGGAAAGAACCAGCTGGGGCTCTAGGGGGTATCCCCACGCGCCCTGTAGCGGCGCATTAAGCGCGGC
GGGTGTGGTGGTTACGCGCAGCGTGACCGCTACACTTGCCAGCGCCCTAGCGCCCGCTCCTTTCGCTTTCTTCCCTTCCT
TTCTCGCCACGTTCGCCGGCTTTCCCCGTCAAGCTCTAAATCGGGGGCTCCCTTTAGGGTTCCGATTTAGTGCTTTACGGC
ACCTCGACCCCAAAAAACTTGATTAGGGTGATGGTTCACGTAGTGGGCCATCGCCCTGATAGACGGTTTTTCGCCCTTTGA
CGTTGGAGTCCACGTTCTTTAATAGTGGACTCTTGTTCCAAACTGGAACAACACTCAACCCTATCTCGGTCTATTCTTTTGA
TTTATAAGGGATTTTGCCGATTTCGGCCTATTGGTTAAAAAATGAGCTGATTTAACAAAAATTTAACGCGAATTAATTCTGTG
GAATGTGTGTCAGTTAGGGTGTGGAAAGTCCCCAGGCTCCCCAGCAGGCAGAAGTATGCAAAGCATGCATCTCAATTAGT
CAGCAACCAGGTGTGGAAAGTCCCCAGGCTCCCCAGCAGGCAGAAGTATGCAAAGCATGCATCTCAATTAGTCAGCAACC
ATAGTCCCGCCCCTAACTCCGCCCATCCCGCCCCTAACTCCGCCCAGTTCCGCCCATTCTCCGCCCCATGGCTGACTAAT
TTTTTTTATTTATGCAGAGGCCGAGGCCGCCTCTGCCTCTGAGCTATTCCAGAAGTAGTGAGGAGGCTTTTTTGGAGGCCT
```

*FIG. 7 (Cont'd)*

```
AGGCTTTTGCAAAAAGCTCAGATCCCGGACCATGAGCTTCAATACCCTGATTGACTGGAACAGCTGTAGCCCTGAACAGCA
GCGTGCGCTGCTGACGCGTCCGGCGATTTCCGCCTCTGACAGTATTACCCGGACGGTCAGCCGATATTCTGGATAATGTAA
AAACGCGCGGTGACGATGCCCTGCGTGAATACAGCGCTAAATTTGATAAAACAGAAGTGACAGCGCTACGCGTCACCCCT
GAAGAGATCGCCGCCGCCGGCGCGCGTCTGAGCGACGAATTAAAACAGGCGATGACCGCTGCCGTCAAAAATATTGAAA
CGTTCCATTCCGCGCAGACGCTACCGCCTGTAGATGTGGAAACCCAGCCAGGCGTGCGTTGCCAGCAGGTTACGCGTCC
CGTCTCGTCTGTCGGTCTGTATATTCCCGGCGGCTCGGCTCCGCTCTTCTCAACGGTGCTGATGCTGGCGACGCCGGCG
CGCATTGCGGGATGCCAGAAGGTGGTTCTGTGCTCGCCGCCGCCCATCGCTGATGAAATCCTCTATGCGGCGCAACTGT
GTGGCGTGCAGGAAATCTTTAACGTCGGCGGCGCGCAGGCGATTGCCGCTCTGGCCTTCGGCAGCGAGTCCGTACCGAA
AGTGGATAAAATTTTTGGCCCCGGCAACGCCTTTGTAACCGAAGCCAAACGTCAGGTCAGCCAGCGTCTCGACGGCGCGG
CTATCGATATGCCAGCCGGGCCGTCTGAAGTACTGGTGATCGCAGACAGCGGCGCAACACCGGATTTCGTCGCTTCTGAC
CTGCTCTCCCAGGCTGAGCACGGCCCGGATTCCCAGGTGATCCTGCTGACGCCTGATGCTGACATTGCCCGCAAGGTGG
CGGAGGCGGTAGAACGTCAACTGGCGGAACTGCCGCGCGCGGACACCGCCCGGCAGGCCCTGAGCGCCAGTCGTCTGA
TTGTGACCAAAGATTTAGCGCAGTGCGTCGCCATCTCTAATCAGTATGGGCCGGAACACTTAATCATCCAGACGCGCAATG
CGCGCGATTTGGTGGATGCGATTACCAGCGCAGGCTCGGTATTTCTCGGCGACTGGTCGCCGGAATCCGCCGGTGATTA
CGCTTCCGGAACCAACCATGTTTTACCGACCTATGGCTATACTGCTACCTGTTCCAGCCTTGGGTTAGCGGATTTCCAGAA
ACGGATGACCGTTCAGGAACTGTCGAAAGCGGGCTTTTCCGCTCTGGCATCAACCATTGAAACATTGGCGGCGGCAGAAC
GTCTGACCGCCCATAAAAATGCCGTGACCCTGCGCGTAAACGCCCTCAAGGAGCAAGCATGAGCACTGAAAACACTCTCA
GCGTCGCTGACTTAGCCCGGGATCTTTGTGAAGGAACCTTACTTCTGTGGTGTGACATAATTGGACAAACTACCTACAGAG
ATTTAAAGCTCTAAGGTAAATATAAAATTTTTAAGTGTATAATGTGTTAAACTACTGATTCTAATTGTTTGTGTATTTAGATTC
CAACCTATGGAACTGATGAATGGGAGCAGTGGTGGAATGCCTTTAATGAGGAAAACCTGTTTTGCTCAGAAGAAATGCCAT
CTAGTGATGATGAGGCTACTGCTGACTCTCAACATTCTACTCCTCCAAAAAAGAAGAGAAAGGTAGAAGACCCCAAGGACT
TTCCTTCAGAATTGCTAAGTTTTTTGAGTCATGCTGTGTTTAGTAATAGAACTCTTGCTTGCTTTGCTATTTACACCACAAAG
GAAAAAGCTGCACTGCTATACAAGAAAATTATGGAAAAATATTCTGTAACCTTTATAAGTAGGCATAACAGTTATAATCATAA
CATACTGTTTTTTCTTACTCCACACAGGCATAGAGTGTCTGCTATTAATAACTATGCTCAAAAATTGTGTACCTTTAGCTTTTT
AATTTGTAAAGGGGTTAATAAGGAATATTTGATGTATAGTGCCTTGACTAGAGATCATAATCAGCCATACCACATTTGTAGA
GGTTTTACTTGCTTTAAAAAACCTCCCACACCTCCCCCTGAACCTGAAACATAAATGAATGCAATTGTTGTTGTTCTGCATT
AATGAATCGGCCAACGCGCGGGGAGAGGCGGTTTGCGTATTGGGCGCTCTTCCGCTTCCTCGCTCACTGACTCGCTGCG
CTCGGTCGTTCGGCTGCGGCGAGCGGTATCAGCTCACTCAAAGGCGGTAATACGGTTATCCACAGAATCAGGGGATAACG
CAGGAAAGAACATGTGAGCAAAAGGCCAGCAAAAGGCCAGGAACCGTAAAAAGGCCGCGTTGCTGGCGTTTTTCCATAGG
CTCCGCCCCCTGACGAGCATCACAAAAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTACCGGATACCTGTCCGCCTTTCTCC
CTTCGGGAAGCGTGGCGCTTTCTCATAGCTCACGCTGTAGGTATCTCAGTTCGGTGTAGGTCGTTCGCTCCAAGCTGGGC
TGTGTGCACGAACCCCCCGTTCAGCCCGACCGCTGCGCCTTATCCGGTAACTATCGTCTTGAGTCCAACCCGGTAAGACA
CGACTTATCGCCACTGGCAGCAGCCACTGGTAACAGGATTAGCAGAGCGAGGTATGTAGGCGGTGCTACAGAGTTCTTGA
AGTGGTGGCCTAACTACGGCTACACTAGAAGAACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGTTTTTTTGTTTGCAAGCAGCAGATTACGCGCA
GAAAAAAAGGATCTCAAGAAGATCCTTTGATCTTTTCTACGGGGTCTGACGCTCAGTGGAACGAAAACTCACGTTAAGGGA
TTTTGGTCATGAGATTATCAAAAAGGATCTTCACCTAGATCCTTTTAAATTAAAAATGAAGTTTTAAATCAATCTAAAGTATAT
ATGAGTAAACTTGGTCTGACAGTTACCAATGCTTAATCAGTGAGGCACCTATCTCAGCGATCTGTCTATTTCGTTCATCCAT
AGTTGCCTGACTCCCCGTCGTGTAGATAACTACGATACGGGAGGGCTTACCATCTGGCCCCAGTGCTGCAATGATACCGC
GAGACCCACGCTCACCGGCTCCAGATTTATCAGCAATAAACCAGCCAGCCGGAAGGGCCGAGCGCAGAAGTGGTCCTGC
AACTTTATCCGCCTCCATCCAGTCTATTAATTGTTGCCGGGAAGCTAGAGTAAGTAGTTCGCCAGTTAATAGTTTGCGCAAC
GTTGTTGCCATTGCTACAGGCATCGTGGTGTCACGCTCGTCGTTTGGTATGGCTTCATTCAGCTCCGGTTCCCAACGATCA
AGGCGAGTTACATGATCCCCCATGTTGTGCAAAAAAGCGGTTAGCTCCTTCGGTCCTCCGATCGTTGTCAGAAGTAAGTTG
GCCGCAGTGTTATCACTCATGGTTATGGCAGCACTGCATAATTCTCTTACTGTCATGCCATCCGTAAGATGCTTTTCTGTGA
CTGGTGAGTACTCAACCAAGTCATTCTGAGAATAGTGTATGCGGCGACCGAGTTGCTCTTGCCCGGCGTCAATACGGGAT
AATACCGCGCCACATAGCAGAACTTTAAAAGTGCTCATCATTGGAAAACGTTCTTCGGGGCGAAAACTCTCAAGGATCTTA
CCGCTGTTGAGATCCAGTTCGATGTAACCCACTCGTGCACCCAACTGATCTTCAGCATCTTTTACTTTCACCAGCGTTTCTG
GGTGAGCAAAAACAGGAAGGCAAAATGCCGCAAAAAAGGGAATAAGGGCGACACGGAAATGTTGAATACTCATACTCTTC
CTTTTTCAATATTATTGAAGCATTTATCAGGGTTATTGTCTCATGAGCGGATACATATTTGAATGTATTTAGAAAAATAAACAA
ATAGGGGTTCCGCGCACATTTCCCCGAAAAGTGCCACCTGACGTCGACGGATCGGGAGATCTCCCGATCCCCTATGGTGC
ACTCTCAGTACAATCTGCTCTGATGCCGCATAGTTAAGCCAGTA
```

*FIG. 7 (Cont'd)* cAF334

Light Chain
DIVMTQTPPSVPVTPGESVSISCR<u>SSKSLLHSNGNTYLY</u>WFLQRPGQSPQLLIY<u>RMSNLAS</u>GVPDRFSGSG
                                            CDR-L1                              CDR-L2

SGTAFTLRISRVEAEDVGVYYC<u>MQHLEYPFT</u>FGSGTKLEIKRTVAAPSVFIFPPSDEQLKSGTASVVCLLN
                      CDR-L3

NFYPREAKVQWKVDNALQSGNSQESVTEQDSKDSTYSLSSTLTLSKADYEKHKVYACEVTHQGLSSPVTKS
FNRGEC

Heavy Chain
QVQLQQSGAELVRPGVSVKISCKGSGYTFTD<u>YAMH</u>WVKQSHAKSLEWIG<u>VISTYFGDATYNQKFKG</u>KATMT
                                   CDR-H1                     CDR-H2

VDKSSSTAYMELARLTSEDSAIYYCARED<u>YVPFAYW</u>GQGTLVTVSAASTKGPSVFPLAPSSKSTSGGTAAL
                             CDR-H3

GCLVKDYFPEPVTVSWNSGALTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRWQQGNVFSCSVMHEALHNHYTQKSLS
LSPGK.

*FIG. 8*

|  | kON (x 105M-1s-1) | Koff(X10-4s-1) | KD(nM) |
|---|---|---|---|
| Dissociation | 1.37  0.18 | 9.32  0.73 | 6.99  1.49 |

| ADC | Cell Line IC50 (M) | | | | |
|---|---|---|---|---|---|
| | IMR32 | CHO | CHO-TEM8 | 293 | 293-TEM8 |
| cAF334-MMAE | 3X10-10 | 1.5X10-7 | 5X10-7 | 3X10-8 | 2X10-10 |
| Rituximab-MMAE | 2X10-8 | 4X10-7 | 4X10-7 | 1X10-7 | 3X10-8 |

SEQUENCE LISTING

<160> NUMBER OF SEQ ID NOS: 52

<210> SEQ ID NO 1
<211> LENGTH: 114
<212> TYPE: PRT
<213> ORGANISM: Artificial Sequence
<220> FEATURE:
<223> OTHER INFORMATION: Synthetic peptide

<400> SEQUENCE: 1

Asp Ile Val Met Thr Gln Thr Pro Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110

Arg Ala

<210> SEQ ID NO 2
<211> LENGTH: 117
<212> TYPE: PRT
<213> ORGANISM: Artificial Sequence
<220> FEATURE:
<223> OTHER INFORMATION: Synthetic peptide

<400> SEQUENCE: 2

Gln Val Lys Leu Glu Glu Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Val Ile Ser Thr Tyr Phe Gly Asp Ala Thr Tyr Asn Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Glu Asp Tyr Val Pro Phe Ala Tyr Trp Gly Gln Gly Thr Leu
            100                 105                 110

Val Thr Val Ser Ala
        115

<210> SEQ ID NO 3
<211> LENGTH: 18
<212> TYPE: DNA
<213> ORGANISM: Artificial Sequence
<220> FEATURE:
<223> OTHER INFORMATION: Synthetic primer

<400> SEQUENCE: 3
cagcttggat acacgccg                                                18

<210> SEQ ID NO 4
<211> LENGTH: 19
<212> TYPE: DNA
<213> ORGANISM: Artificial Sequence
<220> FEATURE:
<223> OTHER INFORMATION: Synthetic primer

<400> SEQUENCE: 4
tgccaaacct acaggtggg                                               19

<210> SEQ ID NO 5
<211> LENGTH: 17
<212> TYPE: DNA
<213> ORGANISM: Artificial Sequence
<220> FEATURE:
<223> OTHER INFORMATION: Synthetic primer

<400> SEQUENCE: 5
cggcaggtca tccacgg                                                 17

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
cggacagctt gtagtaccca g                                            21

<210> SEQ ID NO 7
<211> LENGTH: 18
<212> TYPE: DNA
<213> ORGANISM: Artificial Sequence
<220> FEATURE:
<223> OTHER INFORMATION: Synthetic primer

<400> SEQUENCE: 7
tgctaaccct gcccaacg                                                18

<210> SEQ ID NO 8
<211> LENGTH: 19
<212> TYPE: DNA
<213> ORGANISM: Artificial Sequence
<220> FEATURE:
<223> OTHER INFORMATION: Synthetic primer

<400> SEQUENCE: 8
cctctcaatg gcgaacacg                                               19

<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9
tgtccctgtc cgagtgctg                                               19

<210> SEQ ID NO 10
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 10
ccaggatggc tgagatcacc                                            20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
cccatcctgt ctgtccgaac                                            20

<210> SEQ ID NO 12
<211> LENGTH: 19
<212> TYPE: DNA
<213> ORGANISM: Artificial Sequence
<220> FEATURE:
<223> OTHER INFORMATION: Synthetic primer

<400> SEQUENCE: 12
cacgccattc ttcagccag                                             19

<210> SEQ ID NO 13
<211> LENGTH: 18
<212> TYPE: DNA
<213> ORGANISM: Artificial Sequence
<220> FEATURE:
<223> OTHER INFORMATION: Synthetic primer

<400> SEQUENCE: 13
gccgaccgaa tgcagaag                                              18

<210> SEQ ID NO 14
<211> LENGTH: 23
<212> TYPE: DNA
<213> ORGANISM: Artificial Sequence
<220> FEATURE:
<223> OTHER INFORMATION: Synthetic primer

<400> SEQUENCE: 14
ggacattcac agttgtgtgc tag                                        23

<210> SEQ ID NO 15
<211> LENGTH: 18
<212> TYPE: DNA
<213> ORGANISM: Artificial Sequence
<220> FEATURE:
<223> OTHER INFORMATION: Synthetic primer

<400> SEQUENCE: 15
gccaacggta gacgcctc                                              18

<210> SEQ ID NO 16
<211> LENGTH: 19
<212> TYPE: DNA
<213> ORGANISM: Artificial Sequence
<220> FEATURE:
<223> OTHER INFORMATION: Synthetic primer

<400> SEQUENCE: 16
taggacccac aaggcatcg                                             19
```

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
cgtagccaga aggagttgcc                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
atgtccacac gaagtgaccg                                              20

<210> SEQ ID NO 19
<211> LENGTH: 342
<212> TYPE: DNA
<213> ORGANISM: Artificial Sequence
<220> FEATURE:
<223> OTHER INFORMATION: Synthetic primer

<400> SEQUENCE: 19
gacattgtga tgacccagac tccaccctct gtacctgtca ctcctggaga gtcagtatcc    60
atctcctgca ggtctagtaa gagtctcctg catagtaatg caacacttta cttgtattgg   120
ttcctgcaga ggccaggcca gtctcctcag ctcctgatat atcggatgtc caaccttgcc   180
tcaggagtcc cagacaggtt cagtggcagt gggtcaggaa ctgctttcac actgagaatc   240
agtagagtgg aggctgagga tgtgggtgtt tattactgta tgcaacatct agaatatcca   300
ttcacgttcg gctcggggac aaagttggaa ataaaacggg ct                     342

<210> SEQ ID NO 20
<211> LENGTH: 351
<212> TYPE: DNA
<213> ORGANISM: Artificial Sequence
<220> FEATURE:
<223> OTHER INFORMATION: Synthetic primer

<400> SEQUENCE: 20
caggttaagc tggaggagtc aggggctgag ctggtgaggc ctgggtctc agtgaagatt     60 tcctgcaagg gttctggcta cacattcact gattatgcta tgcactgggt gaagcagagt   120
catgcaaaga gtctagagtg gattggagtt attagtactt actttggtga tgctacctac   180
aaccagaagt tcaagggcaa ggccacaatg actgtagaca atcctccag cacagcctat    240 atggaacttg ccagactgac atctgaggat tctgccatct attactgtgc aagagaggat   300
tacgtcccgt ttgcttactg gggccaaggg actctggtca ctgtctctgc a            351

<210> SEQ ID NO 21
<211> LENGTH: 5540
<212> TYPE: DNA
<213> ORGANISM: Homo sapiens

<400> SEQUENCE: 21
aattgcttcc ggggagttgc gagggagcga gggggaataa aggacccgcg aggaagggcc    60
cgcggatggc gcgtccctga gggtcgtggc gagttcgcgg agcgtgggaa ggagcggacc   120

```
ctgctctccc cgggctgcgg gccatggcca cggcggagcg gagagccctc ggcatcggct    180
tccagtggct ctctttggcc actctggtgc tcatctgcgc cgggcaaggg ggacgcaggg    240
aggatggggg tccagcctgc tacggcggat ttgacctgta cttcattttg gacaaatcag    300
gaagtgtgct gcaccactgg aatgaaatct attactttgt ggaacagttg gctcacaaat    360
tcatcagccc acagttgaga atgtccttta ttgttttctc cacccgagga acaaccttaa    420
tgaaactgac agaagacaga gaacaaatcc gtcaaggcct agaagaactc agaaagttc     480 tgccaggagg agacacttac atgcatgaag gatttgaaag ggccagtgag cagatttatt    540
atgaaaacag acaagggtac aggacagcca gcgtcatcat tgctttgact gatggagaac    600
tccatgaaga tctcttttc tattcagaga gggaggctaa taggtctcga gatcttggtg     660
caattgttta ctgtgttggt gtgaaagatt caatgagac acagctggcc cggattgcgg     720
acagtaagga tcatgtgttt cccgtgaatg acggctttca ggctctgcaa ggcatcatcc    780
actcaatttt gaagaagtcc tgcatcgaaa ttctagcagc tgaaccatcc accatatgtg    840
caggagagtc atttcaagtt gtcgtgagag gaaacggctt ccgacatgcc cgcaacgtgg    900
acagggtcct ctgcagcttc aagatcaatg actcggtcac actcaatgag aagcccttt     960 ctgtggaaga tacttattta ctgtgtccag cgcctatctt aaaagaagtt ggcatgaaag   1020
ctgcactcca ggtcagcatg aacgatggcc tctcttttat ctccagttct gtcatcatca   1080
ccaccacaca ctgttctgac ggttccatcc tggccatcgc cctgctgatc ctgttcctgc   1140
tcctagccct ggctctcctc tggtggttct ggccctctg ctgcactgtg attatcaagg    1200
aggtccctcc acccctgcc gaggagagtg aggaagaaga tgatgatggt ctgcctaaga    1260
aaaagtggcc aacggtagac gcctcttatt atggtgggag aggcgttgga ggcattaaaa   1320
gaatggaggt tcgttgggga gaaaagggct ccacagaaga aggtgctaag ttggaaaagg   1380
caaagaatgc aagagtcaag atgccggagc aggaatatga attccctgag ccgcgaaatc   1440
tcaacaacaa tatgcgtcgg ccttcttccc cccggaagtg gtactctcca atcaagggaa   1500
aactcgatgc cttgtgggtc ctactgagga aaggatatga tcgtgtgtct gtgatgcgtc   1560
cacagccagg agacacgggg cgctgcatca acttcaccag ggtcaagaac aaccagccag   1620
ccaagtaccc actcaacaac gcctaccaca cctcctcgcc gcctcctgcc cccatctaca   1680
ctcccccacc tcctgcgccc cactgccctc ccccgccccc cagcgcccct acccctccca   1740
tcccgtcccc accttccacc cttcccctc ctccccaggc tccacctccc aacagggcac   1800
ctcctccctc ccgccctcct ccaaggcctt ctgtctagag cccaaagttc ctgctctggg   1860
ctctctcaga aacttcagga gatgttagaa caagtctttc cagttagaga agaggagtgg   1920
tgataaagcc cactgacctt cacacattct aaaaattggt tggcaatgcc agtataccaa   1980
caatcatgat cagctgaaag aaacagatat tttaaattgc cagaaaacaa atgatgaggc   2040
aactacagtc agatttatag ccagccatct atcacctcta gaaggttcca gagacagtga   2100
aactgcaaga tgctctcaac aggattatgt ctcatggaga ccagtaagaa aatcatttat   2160
ctgaaggtga aatgcagagt tggataagaa atacattgct gggtttctaa aatgctgcct   2220
tcctgcctct actccacctc catccctgga ctttggaccc ttggcctagg agcctaagga   2280
ccttcacccc tgtgcaccac caagaaaga ggaaaacttt gcctacaact ttggaaatgc     2340
tggggtccct ggtgtggtaa gaaactcaac atcagacggg tatgcagaag gatgttcttc   2400
tgggatttgc aggtacataa aaaatgtatg gcatcttttc cttgcaaatt cttccagttt   2460
```

```
ccaagtgaga aggggagcag gtgtttactg atggaaaagg tatgttgcta tgttgatgtg    2520
taagtgaaat cagttgtgtg caatagacag gggcgtattc atgggagcat cagccagttt    2580
ctaaaaccca caggccatca gcagctagag gtggctggct ttggccagac atggacccta    2640
aatcaacaga caatggcatt gtcgaagagc aacctgttaa tgaatcatgt taaaaatcaa    2700
ggtttggctt cagtttaaat cacttgaggt atgaagttta tcctgttttc cagagataaa    2760
cataagttga tcttcccaaa ataccatcat taggacctat cacacaatat cactagtttt    2820
ttttgtttgt ttgttttttg ttttttttct tggtaaagcc atgcaccaca gacttctggg    2880
cagagctgag agacaatggt cctgacataa taaggatctt tgattaaccc ccataaggca    2940
tgtgtgtgta tacaaatata cttctctttg gcttttcgac atagaacctc agctgttaac    3000
caaggggaaa tacatcagat ctgcaacaca gaaatgctct gcctgaaatt tccaccatgc    3060
ctaggactca ccccatttat ccaggtcttt ctggatctgt ttaatcaata gccctataa    3120 tcacttgcta aacactgggc ttcatcaccc agggataaaa acagagatca ttgtcttgga    3180
cctcctgcat cagcctattc aaaattatct ctctctctag ctttccacaa atcctaaaat    3240
tcctgtccca agccacccaa attctcagat cttttctgga acaaggcaga atataaaata    3300
aatatacatt tagtggcttg ggctatggtc tccaaagatc cttcaaaaat acatcaagcc    3360
agcttcattc actcacttta cttagaacag agatataagg gcctgggatg catttatttt    3420
atcaatacca attttgtgg ccatggcaga cattgctaat caatcacagc actatttcct    3480
attaagccca ctgatttctt cacaatcctt ctcaaattac aattccaaag agccgccact    3540
caacagtcag atgaacccaa cagtcagatg agagaaatga accctacttg ctatctctat    3600
cttagaaagc aaaaacaaac aggagtttcc agggagaatg ggaaagccag ggggcataaa    3660
aggtacagtc aggggaaaat agatctaggc agagtgcctt agtcagggac cacgggcgct    3720
gaatctgcag tgccaacacc aaactgacac atctccaggt gtacctccaa ccctagcctt    3780
ctcccacagc tgcctacaac agagtctccc agccttctca gagagctaaa accagaaatt    3840
tccagactca tgaaagcaac ccccagcct ctccccaacc ctgccgcatt gtctaatttt    3900
tagaacacta ggcttcttct ttcatgtagt tcctcataag caggggccag aatatctcag    3960
ccacctgcag tgacattgct ggaccctga aaaccattcc ataggagaat gggttcccca    4020
ggctcacagt gtagagacat tgagcccatc acaactgttt tgactgctgg cagtctaaaa    4080
cagtccaccc acccatggc actgccgcgt gattcccgcg gccattcaga agttcaagcc    4140
gagatgctga cgttgctgag caacgagatg gtgagcatca gtgcaaatgc accattcagc    4200
acatcagtca tatgcccagt gcagttacaa gatgttgttt cggcaaagca ttttgatgga    4260
atagggaact gcaaatgtat gatgattttg aaaaggctca gcaggatttg ttcttaaacc    4320
gactcagtgt gtcatccccg gttatttaga attacagtta agaaggagaa acttctataa    4380
gactgtatga acaaggtgat atcttcatag tgggctatta caggcaggaa aatgttttaa    4440
ctggtttaca aaatccatca atacttgtgt cattccctgt aaaaggcagg agacatgtga    4500
ttatgatcag gaaactgcac aaaattattg ttttcagccc ccgtgttatt gtccttttga    4560 actgttttt ttttattaaa gccaaatttg tgttgtatat attcgtattc catgtgttag    4620
atggaagcat ttcctatcca gtgtgaataa aaagaacagt tgtagtaaat tattataaag    4680
ccgatgatat ttcatggcag gttattctac caagctgtgc ttgttggttt ttcccatgac    4740
tgtattgctt ttataaatgt acaaatagtt actgaaatga cgagacccct gtttgcacag    4800
cattaataag aaccttgata agaaccatat tctgttgaca gccagctcac agtttcttgc    4860
```

```
ctgaagcttg gtgcaccctc cagtgagaca caagatctct cttttaccaa agttgagaac    4920
agagctggtg gattaattaa tagtcttcga tatctggcca tgggtaacct cattgtaact    4980
atcatcagaa tgggcagaga tgatcttgaa gtgtcacata cactaaagtc caaacactat    5040
gtcagatggg ggtaaaatcc attaaagaac aggaaaaaat aattataaga tgataagcaa    5100
atgtttcagc ccaatgtcaa cccagttaaa aaaaaatta atgctgtgta aatggttga     5160 attagtttgc aaactatata aagacatatg cagtaaaaag tctgttaatg cacatcctgt    5220
gggaatggag tgttctaacc aattgccttt tcttgttatc tgagctctcc tatattatca    5280
tactcagata accaaattaa aagaattaga atatgatttt taatacactt aacattaaac    5340
tcttctaact ttcttctttc tgtgataatt cagaagatag ttatggatct tcaatgcctc    5400
tgagtcattg ttataaaaaa tcagttatca ctataccatg ctataggaga ctgggcaaaa    5460
cctgtacaat gacaaccctg gaagttgctt tttttaaaaa aataataaat ttcttaaatc    5520
aaaaaaaaaa aaaaaaaaaa                                                5540
```

<210> SEQ ID NO 22
<211> LENGTH: 295
<212> TYPE: PRT
<213> ORGANISM: Homo sapiens

<400> SEQUENCE: 22

```
Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
        115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
    210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
```

```
                    245                 250                 255
Gly Ala Val Val Phe Val Val Ile Ile Leu Val Ile Ile Leu Ala Ile
            260                 265                 270
Ser Leu His Lys Cys Arg Lys Ala Gly Val Gly Gln Ser Trp Lys Glu
            275                 280                 285
Asn Ser Pro Leu Asn Val Ser
        290                 295
```

<210> SEQ ID NO 23
<211> LENGTH: 238
<212> TYPE: PRT
<213> ORGANISM: Homo sapiens

<400> SEQUENCE: 23

```
Met Glu Thr Pro Ala Trp Pro Arg Val Pro Arg Pro Glu Thr Ala Val
1               5                   10                  15
Ala Arg Thr Leu Leu Leu Gly Trp Val Phe Ala Gln Val Ala Gly Ala
            20                  25                  30
Ser Gly Thr Thr Asn Thr Val Ala Ala Tyr Asn Leu Thr Trp Lys Ser
        35                  40                  45
Thr Asn Phe Lys Thr Ile Leu Glu Trp Glu Pro Lys Pro Val Asn Gln
    50                  55                  60
Val Tyr Thr Val Gln Ile Ser Thr Lys Ser Gly Asp Trp Lys Ser Lys
65                  70                  75                  80
Cys Phe Tyr Thr Thr Asp Thr Glu Cys Asp Leu Thr Asp Glu Ile Val
                85                  90                  95
Lys Asp Val Lys Gln Thr Tyr Leu Ala Arg Val Phe Ser Tyr Pro Ala
            100                 105                 110
Gly Asn Val Glu Ser Thr Gly Ser Ala Gly Glu Pro Leu Tyr Glu Asn
        115                 120                 125
Ser Pro Glu Phe Thr Pro Tyr Leu Glu Thr Asn Leu Gly Gln Pro Thr
    130                 135                 140
Ile Gln Ser Phe Glu Gln Val Gly Thr Lys Val Asn Val Thr Val Glu
145                 150                 155                 160
Asp Glu Arg Thr Leu Val Arg Arg Asn Asn Thr Phe Leu Ser Leu Arg
                165                 170                 175
Asp Val Phe Gly Lys Asp Leu Ile Tyr Thr Leu Tyr Tyr Trp Lys Ser
            180                 185                 190
Ser Ser Ser Gly Lys Lys Tyr Ser Thr Ser Leu Glu Leu Trp Tyr Leu
        195                 200                 205
Trp Ser Ser Ser Leu Ser Ser Ser Trp Leu Tyr Leu Tyr Thr Ser Val
    210                 215                 220
Glu Arg Gln Glu Trp Gly Arg Ala Gly Arg Arg Thr Pro His
225                 230                 235
```

<210> SEQ ID NO 24
<211> LENGTH: 32
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (18)..(18)
<223> OTHER INFORMATION: n is a, c, g, or t

<400> SEQUENCE: 24
cttccggaat tcsargtnma gctgsagsag tc                                32

<210> SEQ ID NO 25
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (18)..(18)
<223> OTHER INFORMATION: n is a, c, g, or t

<400> SEQUENCE: 25
cttccggaat tcsargtnma gctgsagsag tcwgg                              35

<210> SEQ ID NO 26
<211> LENGTH: 33
<212> TYPE: DNA
<213> ORGANISM: Artificial Sequence
<220> FEATURE:
<223> OTHER INFORMATION: Synthetic primer

<400> SEQUENCE: 26
ggaagatctg acatttggga aggactgact ctc                                33

<210> SEQ ID NO 27
<211> LENGTH: 30
<212> TYPE: DNA
<213> ORGANISM: Artificial Sequence
<220> FEATURE:
<223> OTHER INFORMATION: Synthetic primer

<400> SEQUENCE: 27
ggtgcatgcg gatacagttg gtgcagcatc                                    30

<210> SEQ ID NO 28
<211> LENGTH: 32
<212> TYPE: DNA
<213> ORGANISM: Artificial Sequence
<220> FEATURE:
<223> OTHER INFORMATION: Synthetic primer

<400> SEQUENCE: 28
gggagctcga yattgtgmts acmcarwctm ca                                 32

<210> SEQ ID NO 29
<211> LENGTH: 18
<212> TYPE: DNA
<213> ORGANISM: Artificial Sequence
<220> FEATURE:
<223> OTHER INFORMATION: Synthetic primer

<400> SEQUENCE: 29
aggcgtgtac ggtgggag                                                 18

<210> SEQ ID NO 30
<211> LENGTH: 82
<212> TYPE: DNA
<213> ORGANISM: Artificial Sequence
<220> FEATURE:
<223> OTHER INFORMATION: Synthetic primer

<400> SEQUENCE: 30
cttgtcatcg tcatccttgt aatcgatgtc atgatcttta taatcaccgt catggtcttt   60
gtagtccccg gcgcagatga gc                                            82

<210> SEQ ID NO 31
<211> LENGTH: 40
<212> TYPE: DNA
<213> ORGANISM: Artificial Sequence
<220> FEATURE:
<223> OTHER INFORMATION: Synthetic primer

<400> SEQUENCE: 31
gattacaagg atgacgatga caagcaaggg ggacgcaggg                          40

<210> SEQ ID NO 32
<211> LENGTH: 20
<212> TYPE: DNA
<213> ORGANISM: Artificial Sequence
<220> FEATURE:
<223> OTHER INFORMATION: Synthetic primer

<400> SEQUENCE: 32
ctggtgaagt tgatgcagcg                                                20

<210> SEQ ID NO 33
<211> LENGTH: 9201
<212> TYPE: DNA
<213> ORGANISM: Artificial Sequence
<220> FEATURE:
<223> OTHER INFORMATION: Synthetic primer

<400> SEQUENCE: 33
ctctcagtac aatctgctct gatgccgcat agttaagcca gtatctgctc cctgcttgtg    60
tgttggaggt cgctgagtag tgcgcgagca aatttaagc tacaacaagg caaggcttga    120
ccgacaattg catgaagaat ctgcttaggg ttaggcgttt tgcgctgctt cgcgatgtac   180
gggccagata tacgcgttga cattgattat tgactagtta ttaatagtaa tcaattacgg   240
ggtcattagt tcatagccca tatatggagt tccgcgttac ataacttacg gtaaatggcc   300
cgcctggctg accgcccaac gacccccgcc cattgacgtc aataatgacg tatgttccca   360
tagtaacgcc aatagggact ttccattgac gtcaatgggt ggagtattta cggtaaactg   420
cccacttggc agtacatcaa gtgtatcata tgccaagtac gccccctatt gacgtcaatg   480
acggtaaatg gcccgcctgg cattatgccc agtacatgac cttatgggac tttcctactt   540
ggcagtacat ctacgtatta gtcatcgcta ttaccatggt gatgcggttt tggcagtaca   600
tcaatgggcg tggatagcgg tttgactcac ggggatttcc aagtctccac cccattgacg   660
tcaatgggag tttgttttgg caccaaaatc aacgggactt tccaaaatgt cgtaacaact   720
ccgccccatt gacgcaaatg ggcggtaggc gtgtacggtg ggaggtctat ataagcagag   780
ctctctggct aactagagaa cccactgctt actggcttat cgaaattaat acgactcact   840
atagggagac ccaagctggc tagcgtttaa acttaagctt ggtaccgagc tcggatccac   900
tagtccagtg tggtggaatt ctgcagatat ccaccatgga ttttcaaggg cagattttca   960
gcctcctgct aatcagtatc acagtcatag tgtccagtgg agacattgtg atgacccaga  1020
ctccaccctc tgtacctgtc actcctggag agtcagtatc catctcctgc aggtctagta  1080
agagtctcct gcatagtaat ggcaacactt acttgtattg gttcctgcag aggccaggcc  1140
agtctcctca gctcctgata tatcggatgt ccaaccttgc ctcaggagtc ccagacaggt  1200
tcagtggcag tgggtcagga actgctttca cactgagaat cagtagagtg gaggctgagg  1260
atgtgggtgt ttattactgt atgcaacatc tagaatatcc attcacgttc ggctcgggga  1320
caaagttgga aataaaacgt aagtcgactt ttctcatctt tttttatgtg taagacacag  1380

```
gttttcatgt taggagttaa agtcagttca gaaaatcttg agaaaatgga gagggctcat    1440
tatcagttga cgtggcatac agtgtcagat tttctgtttta tcaagctagt gagattaggg    1500
gcaaaaagag ctttagttg agaggaaagt aattaatact atggtcacca tccaagagat    1560
tggatcggag aataagcatg agtagttatt gagatctggg tctgactgca ggtagcgtgg    1620
tcttctagac gtttaagtgg gagatttgga ggggatgagg aatgaaggaa cttcaggata    1680
gaaaagggct gaagtcaagt tcagctccta aatggatgt gggagcaaac tttgaagata    1740
aactgaatga cccagaggat gaaacagcgc agatcaaaga ggggcctgga gctctgagaa    1800
gagaaggaga ctcatccgtg ttgagttcc acaagtactg tcttgagttt tgcaataaaa    1860
gtgggatagc agagttgagt gagccgtagg ctgagttctc tcttttgtct cctaagtttt    1920
tatgactaca aaaatcagtg tatgtcctga aataatcatt aagctgtttg aaagtatgac    1980
tgcttgccat gtagatacca tggcttgctg aataatcaga agaggtgtga ctcttattct    2040
aaaatttgtc acaaaatgtc aaatgagag actctgtagg aacgagtcct tgacagacag    2100 ctcaagggt ttttttcctt tgtctcattt ctacatgaaa gtaaatttga aatgatcttt    2160
tttattataa gagtagaaat acagttgggt ttgaactata tgttttaatg gccacggttt    2220
tgtaagacat ttggtccttt gttttcccag ttattactcg attgtaattt tatatcgcca    2280
gcaatggact gaaacggtcc gcaacctctt ctttacaact gggtgacctc gcggctgtgc    2340
cagccatttg gcgttcaccc tgccgctaag ggccatgtga accccgcgg tagcatccct    2400 tgctccgcgt ggaccacttt cctgaggcac agtgatagga acagagccac taatctgaag    2460
agaacagaga tgtgacagac tacactaatg tgagaaaaac aaggaaaggg tgacttattg    2520
gagatttcag aaataaaatg catttattat tatattccct tatttaatt ttctattagg    2580 gaattagaaa gggcataaac tgctttatcc agtgttatat taaaagcttt ttttttttca    2640
gtgctattta attatttcaa tatcctctca tcaaatgtat ttaaataaca aaagctcaac    2700
caaaaagaaa gaaatatgta attctttcag agtaaaaatc acacccatga cctggccact    2760
gagggcttga tcaattcact ttgaatttgg cattaaatac cattaaggta tattaactga    2820
ttttaaaata agatatattc gtgaccatgt ttttaacttt caaaaatgta gctgccagtg    2880 tgtgattttta tttcagttgt acaaaatatc taaacctata gcaatgtgat taataaaac    2940 ttaaacatat tttccagtac cttaattctg tgataggaaa attttaatct gagtatttta    3000
atttcataat ctctaaaata gtttaatgat ttgtcattgt gttgctgtcg tttaccccag    3060
ctgatctcaa aagtgatatt taaggagatt attttggtct gcaacaactt gataggacta    3120
ttttagggcc ttttaaagc tctattaaaa ctaacttaca acgattcaaa actgttttaa    3180
actatttcaa aatgatttta gagccttttg aaaactcttt taaacacttt ttaaactcta    3240
ttaaaactaa taagataact tgaataatt ttcatgtcaa atacattaac tgtttaatgt    3300
ttaaatgcca gatgaaaaat gtaaagctat caagaattca cccagatagg agtatcttca    3360
tagcatgttt ttccctgctt attttccagt gatcacatta ttttgctacc atggttattt    3420
tatacaatta tctgaaaaaa attagttatg aagattaaaa gagaagaaaa tattaaacat    3480
aagagattca gtctttcatg ttgaactgct tggttaacag tgaagttagt tttaaaaaaa    3540
aaaaaaacta tttctgttat cagctgactt ctccctatct gttgacttct cccagcaaaa    3600
gattcttatt ttcatttta actactgctc tcccacccaa cgggtggaat cccccagagg    3660
gggatttcca agaggccacc tggcagttgc tgagggtcag aagtgaagct agccacttcc    3720
```

```
tcttaggcag gtggccaaga ttacagttga cctctcctgg tatggctgaa aattgctgca    3780
tatggttaca ggccttgagg cctttgggag ggcttagaga gttgctggaa cagtcagaag    3840
gtggagggc tgacaccacc caggcgcaga ggcagggctc agggcctgct ctgcagggag     3900
gttttagccc agcccagcca aagtaacccc cgggagcctg ttatcccagc acagtcctgg    3960
aagaggcaca ggggaaataa aagcggacgg aggctttcct tgactcagcc gctgcctggt    4020
cttcttcaga cctgttctga attctaaact ctgaggggt cggatgacgt ggccattctt     4080
tgcctaaagc attgagttta ctgcaaggtc agaaaagcat gcaaagccct cagaatggct    4140
gcaaagagct ccaacaaaac aatttagaac tttattaagg aatagggga agctaggaag     4200
aaactcaaaa catcaagatt ttaaatacgc ttcttggtct ccttgctata attatctggg    4260
ataagcatgc tgttttctgt ctgtccctaa catgccctgt gattatccgc aaacaacaca    4320
cccaagggca gaactttgtt acttaaacac catcctgttt gcttctttcc tcaggaactg    4380
tggctgcacc atctgtcttc atcttcccgc catctgatga gcagttgaaa tctggaactg    4440
cctctgttgt gtgcctgctg aataacttct atcccagaga ggccaaagta cagtggaagg    4500
tggataacgc cctccaatcg ggtaactccc aggagagtgt cacagagcag gacagcaagg    4560
acagcaccta cagcctcagc agcaccctga cgctgagcaa agcagactac gagaaacaca    4620
aagtctacgc ctgcgaagtc acccatcagg gcctgagctc gcccgtcaca aagagcttca    4680
acaggggaga gtgttagagg gagaagtgcc cccacctgct cctcagttcc agcctgaccc    4740
cctcccatcc tttggcctct gacccttttt ccacagggga aaccgctgat cagcctcgac    4800
tgtgccttct agttgccagc catctgttgt ttgcccctcc ccgtgccttt ccttgaccct    4860
ggaaggtgcc actcccactg tccttttccta ataaaatgag gaaattgcat cgcattgtct    4920
gagtaggtgt cattctattc tggggggtgg ggtggggcag gacagcaagg gggaggattg    4980
gcaagacaat agcaggcatg ctggggatgc ggtgggctct atggcttctg aggcggaaag    5040
aaccagctgg ggctctaggg ggtatcccca cgcgccctgt agcggcgcat taagcgcggc    5100
gggtgtggtg gttacgcgca gcgtgaccgc tacacttgcc agcgccctag cgcccgctcc    5160
tttcgctttc ttcccttcct ttctcgccac gttcgccggc tttccccgtc aagctctaaa    5220
tcggggctc cctttagggt tccgatttag tgctttacgg cacctcgacc ccaaaaaact    5280
tgattagggt gatggttcac gtagtgggcc atcgccctga tagacggttt ttcgcccttt    5340
gacgttggag tccacgttct ttaatagtgg actcttgttc caaactggaa caacactcaa    5400
ccctatctcg gtctattctt ttgatttata agggattttg ccgatttcgg cctattggtt    5460
aaaaaatgag ctgatttaac aaaaatttaa cgcgaattaa ttctgtggaa tgtgtgtcag    5520
ttagggtgtg gaaagtcccc aggctcccca gcaggcagaa gtatgcaaag catgcatctc    5580
aattagtcag caaccaggtg tggaaagtcc ccaggctccc cagcaggcag aagtatgcaa    5640
agcatgcatc tcaattagtc agcaaccata gtcccgcccc taactccgcc catcccgccc    5700
ctaactccgc ccagttccgc ccattctccg ccccatggct gactaatttt ttttatttat    5760
gcagaggccg aggccgcctc tgcctctgag ctattccaga agtagtgagg aggctttttt    5820
ggaggcctag gcttttgcaa aaagctcccg ggagcttgta tatccatttt cggatctgat    5880
caagagacag gatgaggatc gtttcgcatg attgaacaag atggattgca cgcaggttct    5940
ccggccgctt gggtggagag gctattcggc tatgactggg cacaacagac aatcggctgc    6000
tctgatgccg ccgtgttccg gctgtcagcg caggggcgcc cggttctttt tgtcaagacc    6060
gacctgtccg gtgccctgaa tgaactgcag gacgaggcag cgcggctatc gtggctggcc    6120
```

```
acgacgggcg ttccttgcgc agctgtgctc gacgttgtca ctgaagcggg aagggactgg    6180
ctgctattgg gcgaagtgcc ggggcaggat ctcctgtcat ctcaccttgc tcctgccgag    6240
aaagtatcca tcatggctga tgcaatgcgg cggctgcata cgcttgatcc ggctacctgc    6300
ccattcgacc accaagcgaa acatcgcatc gagcgagcac gtactcggat ggaagccggt    6360
cttgtcgatc aggatgatct ggacgaagag catcaggggc tcgcgccagc cgaactgttc    6420
gccaggctca aggcgcgcat gcccgacggc gaggatctcg tcgtgaccca tggcgatgcc    6480
tgcttgccga atatcatggt ggaaaatggc cgcttttctg gattcatcga ctgtggccgg    6540
ctgggtgtgg cggaccgcta tcaggacata gcgttggcta cccgtgatat tgctgaagag    6600
cttggcggcg aatgggctga ccgcttcctc gtgctttacg gtatcgccgc tcccgattcg    6660
cagcgcatcg ccttctatcg ccttcttgac gagttcttct gagcgggact ctggggttcg    6720
aaatgaccga ccaagcgacg cccaacctgc catcacgaga tttcgattcc accgccgcct    6780
tctatgaaag gttgggcttc ggaatcgttt tccgggacgc cggctggatg atcctccagc    6840
gcggggatct catgctggag ttcttcgccc accccaactt gtttattgca gcttataatg    6900
gttacaaata aagcaatagc atcacaaatt tcacaaataa agcatttttt tcactgcatt    6960
ctagttgtgg tttgtccaaa ctcatcaatg tatcttatca tgtctgtata ccgtcgacct    7020
ctagctagag cttggcgtaa tcatggtcat agctgtttcc tgtgtgaaat tgttatccgc    7080
tcacaattcc acaacacata cgagccggaa gcataaagtg taaagcctgg ggtgcctaat    7140
gagtgagcta actcacatta attgcgttgc gctcactgcc cgctttccag tcgggaaacc    7200
tgtcgtgcca gctgcattaa tgaatcggcc aacgcgcggg gagaggcggt ttgcgtattg    7260
ggcgctcttc cgcttcctcg ctcactgact cgctgcgctc ggtcgttcgg ctgcggcgag    7320
cggtatcagc tcactcaaag gcggtaatac ggttatccac agaatcaggg gataacgcag    7380
gaaagaacat gtgagcaaaa ggccagcaaa aggccaggaa ccgtaaaaag gccgcgttgc    7440
tggcgttttt ccataggctc cgcccccctg acgagcatca caaaaatcga cgctcaagtc    7500
agaggtggcg aaacccgaca ggactataaa gataccaggc gtttccccct ggaagctccc    7560
tcgtgcgctc tcctgttccg accctgccgc ttaccggata cctgtccgcc tttctccctt    7620
cgggaagcgt ggcgctttct catagctcac gctgtaggta tctcagttcg gtgtaggtcg    7680
ttcgctccaa gctgggctgt gtgcacgaac cccccgttca gcccgaccgc tgcgccttat    7740
ccggtaacta tcgtcttgag tccaacccgg taagacacga cttatcgcca ctggcagcag    7800
ccactggtaa caggattagc agagcgaggt atgtaggcgg tgctacagag ttcttgaagt    7860
ggtggcctaa ctacggctac actagaagaa cagtatttgg tatctgcgct ctgctgaagc    7920
cagttacctt cggaaaaaga gttggtagct cttgatccgg caaacaaacc accgctggta    7980
gcggtggttt ttttgtttgc aagcagcaga ttacgcgcag aaaaaaagga tctcaagaag    8040
atcctttgat cttttctacg gggtctgacg ctcagtggaa cgaaaactca cgttaaggga    8100
ttttggtcat gagattatca aaaaggatct tcacctagat ccttttaaat taaaaatgaa    8160
gttttaaatc aatctaaagt atatatgagt aaacttggtc tgacagttac caatgcttaa    8220
tcagtgaggc acctatctca gcgatctgtc tatttcgttc atccatagtt gcctgactcc    8280
ccgtcgtgta gataactacg atacgggagg gcttaccatc tggccccagt gctgcaatga    8340
taccgcgaga cccacgctca ccggctccag atttatcagc aataaaccag ccagccgaag    8400
gggccgagcg cagaagtggt cctgcaactt tatccgcctc catccagtct attaattgtt    8460
```

```
gccgggaagc tagagtaagt agttcgccag ttaatagttt gcgcaacgtt gttgccattg    8520
ctacaggcat cgtggtgtca cgctcgtcgt ttggtatggc ttcattcagc tccggttccc    8580
aacgatcaag gcgagttaca tgatccccca tgttgtgcaa aaaagcggtt agctccttcg    8640
gtcctccgat cgttgtcaga agtaagttgg ccgcagtgtt atcactcatg gttatggcag    8700
cactgcataa ttctcttact gtcatgccat ccgtaagatg ctttctgtg actggtgagt      8760 actcaaccaa gtcattctga gaatagtgta tgcggcgacc gagttgctct tgcccggcgt    8820
caatacggga taataccgcg ccacatagca gaactttaaa agtgctcatc attggaaaac    8880
gttcttcggg gcgaaaactc tcaaggatct taccgctgtt gagatccagt tcgatgtaac    8940
ccactcgtgc acccaactga tcttcagcat ctttactttt caccagcgtt tctgggtgag    9000
caaaaacagg aaggcaaaat gccgcaaaaa agggaataag ggcgacacgg aaatgttgaa    9060
tactcatact cttccttttt caatattatt gaagcattta tcagggttat tgtctcatga    9120
gcggatacat atttgaatgt atttagaaaa ataaacaaat aggggttccg cgcacatttc    9180
cccgaaaagt gccacctgac g                                              9201

<210> SEQ ID NO 34
<211> LENGTH: 403
<212> TYPE: DNA
<213> ORGANISM: Mus musculus

<400> SEQUENCE: 34
atggattttc aagggcagat tttcagcctc ctgctaatca gtatcacagt catagtgtcc      60
agtggagaca ttgtgatgac ccagactcca ccctctgtac ctgtcactcc tggagagtca    120
gtatccatct cctgcaggtc tagtaagagt ctcctgcata gtaatggcaa cacttacttg    180
tattggttcc tgcagaggcc aggccagtct cctcagctcc tgatatatcg gatgtccaac    240
cttgcctcag gagtcccaga caggttcagt ggcagtgggt caggaactgc tttcacactg    300
agaatcagta gtggaggc tgaggatgtg ggtgtttatt actgtatgca acatctagaa      360
tatccattca cgttcggctc ggggacaaag ttggaaataa aac                      403

<210> SEQ ID NO 35
<211> LENGTH: 321
<212> TYPE: DNA
<213> ORGANISM: Homo sapiens

<400> SEQUENCE: 35
actgtggctg caccatctgt cttcatcttc ccgccatctg atgagcagtt gaaatctgga     60
actgcctctg ttgtgtgcct gctgaataac ttctatccca gagaggccaa agtacagtgg    120
aaggtggata acgccctcca atcgggtaac tcccaggaga gtgtcacaga gcaggacagc    180
aaggacagca cctacagcct cagcagcacc ctgacgctga gcaaagcaga ctacgagaaa    240
cacaaagtct acgcctgcga agtcacccat cagggcctga gctcgcccgt cacaaagagc    300
ttcaacaggg gagagtgtta g                                              321

<210> SEQ ID NO 36
<211> LENGTH: 219
<212> TYPE: PRT
<213> ORGANISM: Artificial Sequence
<220> FEATURE:
<223> OTHER INFORMATION: Synthetic peptide

<400> SEQUENCE: 36

Asp Ile Val Met Thr Gln Thr Pro Pro Ser Val Pro Val Thr Pro Gly
```

```
             1               5                  10                 15
           Glu Ser Val Ser Ile Ser Cys Arg Ser Ser Lys Ser Leu Leu His Ser
                           20                  25                  30

Asn Gly Asn Thr Tyr Leu Tyr Trp Phe Leu Gln Arg Pro Gly Gln Ser
                       35                  40                  45

Pro Gln Leu Leu Ile Tyr Arg Met Ser Asn Leu Ala Ser Gly Val Pro
                   50                  55                  60

Asp Arg Phe Ser Gly Ser Gly Ser Gly Thr Ala Phe Thr Leu Arg Ile
           65                  70                  75                  80

Ser Arg Val Glu Ala Glu Asp Val Gly Val Tyr Tyr Cys Met Gln His
                               85                  90                  95

Leu Glu Tyr Pro Phe Thr Phe Gly Ser Gly Thr Lys Leu Glu Ile Lys
                           100                 105                 110

Arg Thr Val Ala Ala Pro Ser Val Phe Ile Phe Pro Pro Ser Asp Glu
                       115                 120                 125

Gln Leu Lys Ser Gly Thr Ala Ser Val Val Cys Leu Leu Asn Asn Phe
                   130                 135                 140

Tyr Pro Arg Glu Ala Lys Val Gln Trp Lys Val Asp Asn Ala Leu Gln
           145                 150                 155                 160

Ser Gly Asn Ser Gln Glu Ser Val Thr Glu Gln Asp Ser Lys Asp Ser
                               165                 170                 175

Thr Tyr Ser Leu Ser Ser Thr Leu Thr Leu Ser Lys Ala Asp Tyr Glu
                           180                 185                 190

Lys His Lys Val Tyr Ala Cys Glu Val Thr His Gln Gly Leu Ser Ser
                       195                 200                 205

Pro Val Thr Lys Ser Phe Asn Arg Gly Glu Cys
                   210                 215
```

<210> SEQ ID NO 37
<211> LENGTH: 568
<212> TYPE: DNA
<213> ORGANISM: Artificial Sequence
<220> FEATURE:
<223> OTHER INFORMATION: Synthetic primer

<400> SEQUENCE: 37

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagct                                       568
```

<210> SEQ ID NO 38
<211> LENGTH: 9493
<212> TYPE: DNA
<213> ORGANISM: Artificial Sequence
<220> FEATURE:
<223> OTHER INFORMATION: Synthetic primer

<400> SEQUENCE: 38

```
gatctcccga tccctatgg tgcactctca gtacaatctg ctctgatgcc gcatagttaa      60
gccagtatct gctccctgct tgtgtgttgg aggtcgctga gtagtgcgcg agcaaaattt     120
aagctacaac aaggcaaggc ttgaccgaca attgcatgaa gaatctgctt agggttaggc     180
gttttgcgct gcttcgcgat gtacgggcca gatatacgcg ttgacattga ttattgacta     240
gttattaata gtaatcaatt acggggtcat tagttcatag cccatatatg gagttccgcg     300
ttacataact tacggtaaat ggcccgcctg gctgaccgcc caacgacccc cgcccattga     360
cgtcaataat gacgtatgtt cccatagtaa cgccaatagg gactttccat tgacgtcaat     420
gggtggagta tttacggtaa actgcccact tggcagtaca tcaagtgtat catatgccaa     480
gtacgccccc tattgacgtc aatgacggta aatggcccgc ctggcattat gcccagtaca     540
tgaccttatg ggactttcct acttggcagt acatctacgt attagtcatc gctattacca     600
tggtgatgcg gttttggcag tacatcaatg ggcgtggata gcggtttgac tcacggggat     660
ttccaagtct ccaccccatt gacgtcaatg ggagtttgtt ttggcaccaa aatcaacggg     720
actttccaaa atgtcgtaac aactccgccc cattgacgca aatgggcggt aggcgtgtac     780
ggtgggaggt ctatataagc agagctctct ggctaactag agaacccact gcttactggc     840
ttatcgaaat taatacgact cactataggg agacccaagc tggctagact cgagcggccg     900
ccactgtgct ggatatccac catgggatgg agctgggtca tcctctttct ggtagcaaca     960
gctacaggtg tgcactccca ggtccagctg cagcagtctg ggctgagct ggtgaggcct    1020
ggggtctcag tgaagatttc ctgcaagggt tctggctaca cattcactga ttatgctatg    1080
cactgggtga agcagagtca tgcaaagagt ctagagtgga ttggagttat tagtacttac    1140
tttggtgatg ctacctacaa ccagaagttc aagggcaagg ccacaatgac tgtagacaaa    1200
tcctccagca cagcctatat ggaacttgcc agactgacat ctgaggattc tgccatctat    1260
tactgtgcaa gagaggatta cgtcccgttt gcttactggg gccaagggac tctggtcact    1320
gtctctgcag ctagcaccaa gggcccatcg gtcttccccc tggcaccctc ctccaagagc    1380
acctctgggg gcacagcggc cctgggctgc ctggtcaagg actacttccc cgaaccggtg    1440
acggtgtcgt ggaactcagg cgccctgacc agcggcgtgc acaccttccc ggctgtccta    1500
cagtcctcag gactctactc cctcagcagc gtggtgaccg tgccctccag cagcttgggc    1560
acccagacct acatctgcaa cgtgaatcac aagcccagca caccaaggt ggacaagaaa     1620
gttggtgaga ggccagcaca gggagggagg gtgtctgctg gaagccaggc tcagcgctcc    1680
tgcctggacg catcccggct atgcagcccc agtccagggc agcaaggcag ccccgtctg     1740
cctcttcacc cggaggcctc tgcccgcccc actcatgctc agggagaggg tcttctggct    1800
ttttcccag gctctgggca ggcacaggct aggtgcccct aacccaggcc ctgcacacaa      1860
aggggcaggt gctgggctca gacctgccaa gagccatatc cgggaggacc ctgcccctga    1920
cctaagccca cccaaaggc caaactctcc actccctcag ctcggacacc ttctctcctc     1980
ccagattcca gtaactccca atcttctctc tgcagagccc aaatcttgtg acaaaactca    2040
cacatgccca ccgtgcccag gtaagccagc ccaggcctcg ccctccagct caaggcggga    2100
caggtgccct agagtagcct gcatccaggg acaggcccca gccgggtgct gacacgtcca    2160
cctccatctc ttcctcagca cctgaactcc tggggggacc gtcagtcttc ctcttccccc    2220
caaaacccaa ggacaccctc atgatctccc ggacccctga ggtcacatgc gtggtggtgg    2280
acgtgagcca cgaagaccct gaggtcaagt tcaactggta cgtggacggc gtggaggtgc    2340
```

```
ataatgccaa gacaaagccg cgggaggagc agtacaacag cacgtaccgt gtggtcagcg   2400
tcctcaccgt cctgcaccag gactggctga atggcaagga gtacaagtgc aaggtctcca   2460
acaaagccct cccagccccc atcgagaaaa ccatctccaa agccaaaggt gggacccgtg   2520
gggtgcgagg gccacatgga cagaggccgg ctcggcccac cctctgccct gagagtgacc   2580
gctgtaccaa cctctgtccc tacagggcag ccccgagaac acaggtgta caccctgccc   2640 ccatcccggg atgagctgac caagaaccag gtcagcctga cctgcctggt caaaggcttc   2700
tatcccagcg acatcgccgt ggagtgggag agcaatgggc agccggagaa caactacaag   2760
accacgcctc ccgtgctgga ctccgacggc tccttcttcc tctacagcaa gctcaccgtg   2820
gacaagagca ggtggcagca ggggaacgtc ttctcatgct ccgtgatgca tgaggctctg   2880
cacaaccact acacgcagaa gagcctctcc ctgtctccgg gtaaatgagt gcgacggccg   2940
gcaagccccc gctccccggg ctctcgcggt cgcacgagga tgcttggcac gtacccctg    3000 tacatacttc ccgggcgccc agcatggaaa taaagcaccc agcgctgccc tgggcccctg   3060
cgagactgtg atggttcttt ccacgggtca ggccgagtct gaggcctgag tggcatgagg   3120
gaggcagagc gggtcccact gtccccacac tggcccaggc tgtgcaggtg tgcctgggcc   3180
gcctagggtg gggctcagcc aggggctgcc ctcggcaggg tgggggattt gccagcgtgg   3240
ccctccctcc agcagcacct gccctgggct gggccacggg aagccctagg agccctgggg   3300
gacagacaca cagcccctgc ctctgtagga gactgtcctg ttctgtgagc gccctgtcct   3360
ccgacctcca tgcccactcg ggggcatgcc tagtccatgt gcgtagggac aggccctccc   3420
tcacccatct accccacgg cactaacccc tggctgccct gccagcctc gcacccgcat    3480 ggggacacaa ccgactccgg ggacatgcac tctcggggccc tgtggaggga ctggtgcaga   3540
tgcccacaca cacactcagc ccagacccgt tcaacaaacc ccgcactgag gttggccggc   3600
cacacggcca ccacacacac acgtgcacgc ctcacacacg gagcctcacc cgggcgaact   3660
gcacagcacc cagaccagag caaggtcctc gcacacgtga acactcctcg gacacaggcc   3720
cccacgagcc ccacgcggca cctcaaggcc cacgagcctc tcggcagctt ctccacatgc   3780
tgacctgctc agacaaaccc agccctcctc tcacagggt gccc tgcag ccgccacaca    3840 cacacagggg atcacacacc acgtcacgtc cctggccctg gcccacttcc cagtgccgcc   3900
cttccctgca gctgcacctc gggggctccc tgcatacgcc ccccgcctcc tgcagccaca   3960
cgcattgccc gagcgaccct ccctggcccc tgtcgctaca tggacccctg gggcttctcc   4020
tcttttctac atggatgcag tttctcctcc tgctgggcac ggtgctgcct gccctggtca   4080
ctctgcgggg gacagggcct ccagggaaag ctgggtcgag gctgggagct ggctcagact   4140
ggccaggcag agccacaggg agggccttcc agaaccaacc atggtccgaa gcgagaggtg   4200
ggtgtcagat ctgtgtgagt cagctcagga ccacagcggg gcggctccca cggcagacat   4260
ggatccacta gagggcccgt ttaaacccgc tgatcagcct cgactgtgcc ttctagttgc   4320
cagccatctg ttgtttgccc ctccccgtg ccttccttga ccctggaagg tgccactccc    4380
actgtccttt cctaataaaa tgaggaaatt gcatcgcatt gtctgagtag tgtcattct    4440 attctggggg gtggggtggg gcaggacagc aaggggagg attgggaaga caatagcagg    4500
catgctgggg atgcggtggg ctctatggct tctgaggcgg aaagaaccag ctggggctct   4560 aggggtatc cccacgcgcc ctgtagcggc gcattaagcg cggcgggtgt ggtggttacg    4620
cgcagcgtga ccgctacact tgccagcgcc ctagcgcccg ctcctttcgc tttcttccct   4680
```

```
tcctttctcg ccacgttcgc cggctttccc cgtcaagctc taaatcgggg gctcccttta    4740
gggttccgat ttagtgcttt acggcacctc gacccccaaaa aacttgatta gggtgatggt   4800
tcacgtagtg ggccatcgcc ctgatagacg ttttttcgcc ctttgacgtt ggagtccacg    4860
ttctttaata gtggactctt gttccaaact ggaacaacac tcaaccctat ctcggtctat    4920
tcttttgatt tataagggat tttgccgatt tcggcctatt ggttaaaaaa tgagctgatt    4980
taacaaaaat ttaacgcgaa ttaattctgt ggaatgtgtg tcagttaggg tgtggaaagt    5040
ccccaggctc cccagcaggc agaagtatgc aaagcatgca tctcaattag tcagcaacca    5100
ggtgtggaaa gtccccaggc tccccagcag gcagaagtat gcaaagcatg catctcaatt    5160
agtcagcaac catagtcccg ccctaactc cgcccatccc gcccctaact ccgcccagtt    5220
ccgcccattc tccgcccat ggctgactaa ttttttttat ttatgcagag gccgaggccg    5280
cctctgcctc tgagctattc cagaagtagt gaggaggctt ttttggaggc ctaggctttt    5340
gcaaaaagct cagatcccgg accatgagct caatacccct gattgactgg aacagctgta    5400
gccctgaaca gcagcgtgcg ctgctgacgc gtccggcgat ttccgcctct gacagtatta    5460
cccggacggt cagcgatatt ctggataatg taaaaacgcg cggtgacgat gccctgcgtg    5520
aatacagcgc taaatttgat aaaacagaag tgacagcgct acgcgtcacc cctgaagaga    5580
tcgccgccgc cggcgcgcgt ctgagcgacg aattaaaaca ggcgatgacc gctgccgtca    5640
aaaatattga aacgttccat tccgcgcaga cgctaccgcc tgtagatgtg aaacccagc    5700
caggcgtgcg ttgccagcag gttacgcgtc ccgtctcgtc tgtcggtctg tatattcccg    5760
gcggctcggt tccgctcttc tcaacggtgc tgatgctggc gacgccggcg cgcattgcgg    5820
gatgccagaa ggtggttctg tgctcgccgc cgcccatcgc tgatgaaatc ctctatgcgg    5880
cgcaactgtg tggcgtgcag gaaatcttta acgtcggcgg cgcgcaggcg attgccgctc    5940
tggccttcgg cagcgagtcc gtaccgaaag tggataaaat ttttggcccc ggcaacgcct    6000
ttgtaaccga agccaaacgt caggtcagcc agcgtctcga cggcgcggct atcgatatgc    6060
cagccgggcc gtctgaagta ctggtgatcg cagacagcgg cgcaacaccg gatttcgtcg    6120
cttctgacct gctctcccag gctgagcacg gcccggattc ccaggtgatc ctgctgacgc    6180
ctgatgctga cattgcccgc aaggtggcgg aggcggtaga acgtcaactg gcggaactgc    6240
cgcgcgcgga caccgcccgg caggccctga gcgccagtcg tctgattgtg accaaagatt    6300
tagcgcagtg cgtcgccatc tctaatcagt atgggccgga acacttaatc atccagacgc    6360
gcaatgcgcg cgatttggtg gatgcgatta ccagcgcagg ctcggtatttt ctcggcgact   6420
ggtcgccgga atccgccggt gattacgctt ccggaaccaa ccatgtttta ccgacctatg    6480
gctatactgc tacctgttcc agccttgggt tagcggattt ccagaaacgg atgaccgttc    6540
aggaactgtc gaaagcgggc ttttccgctc tggcatcaac cattgaaaca ttggcggcgg    6600
cagaacgtct gaccgcccat aaaaatgccg tgacctgcg cgtaaacgcc ctcaaggagc    6660
aagcatgagc actgaaaaca ctctcagcgt cgctgactta gcccgggatc tttgtgaagg    6720
aaccttactt ctgtggtgtg acataattgg acaaactacc tacagagatt taaagctcta    6780
aggtaaatat aaaattttta agtgtataat gtgttaaact actgattcta attgtttgtg    6840
tattttagat tccaacctat ggaactgatg aatgggagca gtggtggaat gcctttaatg    6900
aggaaaacct gttttgctca gaagaaatgc catctagtga tgatgaggct actgctgact    6960
ctcaacattc tactcctcca aaaaagaaga gaaaggtaga agaccccaag gactttcctt    7020
cagaattgct aagttttttg agtcatgctg tgtttagtaa tagaactctt gcttgctttg    7080
```

```
ctatttacac cacaaaggaa aaagctgcac tgctatacaa gaaaattatg gaaaaatatt    7140
ctgtaacctt tataagtagg cataacagtt ataatcataa catactgttt tttcttactc    7200
cacacaggca tagagtgtct gctattaata actatgctca aaaattgtgt acctttagct    7260
ttttaatttg taaaggggtt aataaggaat atttgatgta tagtgccttg actagagatc    7320
ataatcagcc ataccacatt tgtagaggtt ttacttgctt taaaaaacct cccacacctc    7380
cccctgaacc tgaaacataa aatgaatgca attgttgttg ttctgcatta atgaatcggc    7440
caacgcgcgg ggagaggcgg tttgcgtatt gggcgctctt ccgcttcctc gctcactgac    7500
tcgctgcgct cggtcgttcg gctgcggcga gcggtatcag ctcactcaaa ggcggtaata    7560
cggttatcca cagaatcagg ggataacgca ggaaagaaca tgtgagcaaa aggccagcaa    7620
aaggccagga accgtaaaaa ggccgcgttg ctggcgtttt tccataggct ccgcccccct    7680
gacgagcatc acaaaaatcg acgctcaagt cagaggtggc gaaacccgac aggactataa    7740
agataccagg cgtttccccc tggaagctcc ctcgtgcgct ctcctgttcc gaccctgccg    7800
cttaccggat acctgtccgc ctttctccct tcgggaagcg tggcgctttc tcatagctca    7860
cgctgtaggt atctcagttc ggtgtaggtc gttcgctcca agctgggctg tgtgcacgaa    7920
ccccccgttc agcccgaccg ctgcgcctta tccggtaact atcgtcttga gtccaacccg    7980
gtaagacacg acttatcgcc actggcagca gccactggta acaggattag cagagcgagg    8040
tatgtaggcg gtgctacaga gttcttgaag tggtggccta actacggcta cactagaaga    8100
acagtatttg gtatctgcgc tctgctgaag ccagttacct tcggaaaaag agttggtagc    8160
tcttgatccg gcaaacaaac caccgctggt agcggtggtt tttttgtttg caagcagcag    8220
attacgcgca gaaaaaaagg atcctttga tcttttctac ggggtctgac    8280
gctcagtgga acgaaaactc acgttaaggg attttggtca tgagattatc aaaaaggatc    8340
ttcacctaga tccttttaaa ttaaaaatga agttttaaat caatctaaag tatatatgag    8400
taaacttggt ctgacagtta ccaatgctta atcagtgagg cacctatctc agcgatctgt    8460
ctatttcgtt catccatagt tgcctgactc ccgtcgtgt agataactac gatacgggag    8520
ggcttaccat ctggccccag tgctgcaatg ataccgcgag acccacgctc accggctcca    8580
gatttatcag caataaacca gccagccgga agggccgagc gcagaagtgg tcctgcaact    8640
ttatccgcct ccatccagtc tattaattgt tgccgggaag ctagagtaag tagttcgcca    8700
gttaatagtt tgcgcaacgt tgttgccatt gctacaggca tcgtggtgtc acgctcgtcg    8760
tttggtatgg cttcattcag ctccggttcc caacgatcaa ggcgagttac atgatccccc    8820
atgttgtgca aaaaagcggt tagctccttc ggtcctccga tcgttgtcag aagtaagttg    8880
gccgcagtgt tatcactcat ggttatggca gcactgcata attctcttac tgtcatgcca    8940
tccgtaagat gcttttctgt gactggtgag tactcaacca agtcattctg agaatagtgt    9000
atgcggcgac cgagttgctc ttgcccggcg tcaatacggg ataataccgc gccacatagc    9060
agaactttaa aagtgctcat cattggaaaa cgttcttcgg ggcgaaaact ctcaaggatc    9120
ttaccgctgt tgagatccag ttcgatgtaa cccactcgtg cacccaactg atcttcagca    9180
tcttttactt tcaccagcgt ttctgggtga gcaaaaacag gaaggcaaaa tgccgcaaaa    9240
aagggaataa gggcgacacg gaaatgttga atactcatac tcttcctttt tcaatattat    9300
tgaagcattt atcagggtta ttgtctcatg agcggataca tatttgaatg tatttagaaa    9360
aataaacaaa taggggttcc gcgcacattt ccccgaaaag tgccacctga cgtcgacgga    9420
```

```
tcgggagatc tcccgatccc ctatggtgca ctctcagtac aatctgctct gatgccgcat      9480
agttaagcca gta                                                        9493

<210> SEQ ID NO 39
<211> LENGTH: 365
<212> TYPE: DNA
<213> ORGANISM: Mus musculus

<400> SEQUENCE: 39
atgggatgga gctgggtcat cctctttctg gtagcaacag ctacaggtgt gcactcccag        60
gtccagctgc agcagtctgg ggctgagctg gtgaggcctg ggtctcagt  gaagatttcc       120 tgcaagggtt ctggctacac attcactgat tatgctatgc actgggtgaa gcagagtcat       180
gcaaagagtc tagagtggat tggagttatt agtacttact ttggtgatgc tacctacaac       240
cagaagttca agggcaaggc cacaatgact gtagacaaat cctccagcac agcctatatg       300
gaacttgcca gactgacatc tgaggattct gccatctatt actgtgcaag agaggattac       360
gtccc                                                                  365

<210> SEQ ID NO 40
<211> LENGTH: 295
<212> TYPE: DNA
<213> ORGANISM: Homo sapiens

<400> SEQUENCE: 40
gctagcacca agggcccatc ggtcttcccc ctggcaccct cctccaagag cacctctggg        60
ggcacagcgg ccctgggctg cctggtcaag gactacttcc ccgaaccggt gacggtgtcg       120
tggaactcag gcgccctgac cagcggcgtg cacaccttcc cggctgtcct acagtcctca       180
ggactctact ccctcagcag cgtggtgacc gtgccctcca gcagcttggg cacccagacc       240
tacatctgca acgtgaatca caagcccagc aacaccaagg tggacaagaa agttg           295

<210> SEQ ID NO 41
<211> LENGTH: 330
<212> TYPE: DNA
<213> ORGANISM: Homo sapiens

<400> SEQUENCE: 41
cacctgaact cctgggggga ccgtcagtct tcctcttccc cccaaaaccc aaggacaccc        60
tcatgatctc ccggacccct gaggtcacat gcgtggtggt ggacgtgagc cacgaagacc       120
ctgaggtcaa gttcaactgg tacgtggacg gcgtggaggt gcataatgcc aagacaaagc       180
cgcgggagga gcagtacaac agcacgtacc gtgtggtcag cgtcctcacc gtcctgcacc       240
aggactggct gaatggcaag gagtacaagt gcaaggtctc caacaaagcc ctcccagccc       300
ccatcgagaa aaccatctcc aaagccaaag                                       330

<210> SEQ ID NO 42
<211> LENGTH: 323
<212> TYPE: DNA
<213> ORGANISM: Homo sapiens

<400> SEQUENCE: 42
ggcagccccg agaaccacag gtgtacaccc tgcccccatc ccgggatgag ctgaccaaga        60
accaggtcag cctgacctgc ctggtcaaag gcttctatcc cagcgacatc gccgtggagt       120
gggagagcaa tgggcagccg gagaacaact acaagaccac gcctcccgtg ctggactccg       180
acggctcctt cttcctctac agcaagctca ccgtggacaa gagcaggtgg cagcagggga       240
```

```
acgtcttctc atgctccgtg atgcatgagg ctctgcacaa ccactacacg cagaagagcc    300
tctccctgtc tccgggtaaa tga                                            323
```

<210> SEQ ID NO 43
<211> LENGTH: 447
<212> TYPE: PRT
<213> ORGANISM: Artificial Sequence
<220> FEATURE:
<223> OTHER INFORMATION: Synthetic peptide

<400> SEQUENCE: 43

```
Gln Val Gln Leu Gln Gln Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Val Ile Ser Thr Tyr Phe Gly Asp Ala Thr Tyr Asn Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Glu Asp Tyr Val Pro Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
```

```
                    340                 345                 350
Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 44
<211> LENGTH: 45
<212> TYPE: DNA
<213> ORGANISM: Artificial Sequence
<220> FEATURE:
<223> OTHER INFORMATION: Synthetic primer

<400> SEQUENCE: 44
agcccaaatc ttgtgacaaa actcacacat gcccaccgtg cccag             45

<210> SEQ ID NO 45
<211> LENGTH: 10
<212> TYPE: PRT
<213> ORGANISM: Artificial Sequence
<220> FEATURE:
<223> OTHER INFORMATION: Synthetic peptide

<400> SEQUENCE: 45

Gly Tyr Thr Phe Thr Asp Tyr Ala Met His
1               5                   10

<210> SEQ ID NO 46
<211> LENGTH: 17
<212> TYPE: PRT
<213> ORGANISM: Artificial Sequence
<220> FEATURE:
<223> OTHER INFORMATION: Synthetic peptide

<400> SEQUENCE: 46

Val Ile Ser Thr Tyr Phe Gly Asp Ala Thr Tyr Asn Gln Lys Phe Lys
1               5                   10                  15

Gly

<210> SEQ ID NO 47
<211> LENGTH: 8
<212> TYPE: PRT
<213> ORGANISM: Artificial Sequence
<220> FEATURE:
<223> OTHER INFORMATION: Synthetic peptide

<400> SEQUENCE: 47

Glu Asp Tyr Val Pro Phe Ala Tyr
1               5

<210> SEQ ID NO 48
<211> LENGTH: 16
<212> TYPE: PRT
<213> ORGANISM: Artificial Sequence
<220> FEATURE:
```

```
<223> OTHER INFORMATION: Synthetic peptide

<400> SEQUENCE: 48

Arg Ser Ser Lys Ser Leu Leu His Ser Asn Gly Asn Thr Tyr Leu Tyr
1               5                   10                  15

<210> SEQ ID NO 49
<211> LENGTH: 7
<212> TYPE: PRT
<213> ORGANISM: Artificial Sequence
<220> FEATURE:
<223> OTHER INFORMATION: Synthetic peptide

<400> SEQUENCE: 49

Arg Met Ser Asn Leu Ala Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide

<400> SEQUENCE: 50

Met Gln His Leu Glu Tyr Pro Phe Thr
1               5

<210> SEQ ID NO 51
<211> LENGTH: 24
<212> TYPE: PRT
<213> ORGANISM: Artificial Sequence
<220> FEATURE:
<223> OTHER INFORMATION: Synthetic peptide

<400> SEQUENCE: 51

Arg Asn Leu Thr Ile Arg Arg Val Arg Lys Glu Asp Glu Gly Leu Tyr
1               5                   10                  15

Thr Cys Gln Ala Cys Ser Val Leu
            20

<210> SEQ ID NO 52
<211> LENGTH: 24
<212> TYPE: PRT
<213> ORGANISM: Artificial Sequence
<220> FEATURE:
<223> OTHER INFORMATION: Synthetic peptide

<400> SEQUENCE: 52

Ser Thr Leu Phe Ile Glu Arg Val Thr Glu Glu Asp Glu Gly Val Tyr
1               5                   10                  15

His Cys Lys Ala Thr Asn Gln Lys
            20
```

ANTIBODIES TO TUMOR ENDOTHELIAL MARKER 8

This patent application is a divisional of U.S. patent application Ser. No. 13/884,899, filed Aug. 16, 2013, which is a national phase application under 35 U.S.C. § 371 of International Patent Application No. PCT/US2011/060583, filed Nov. 14, 2011, which claims priority to U.S. Provisional Patent Application Ser. No. 61/527,339, filed Aug. 25, 2011, and U.S. Provisional Patent Application Ser. No. 61/412,999, filed Nov. 12, 2010, the entire contents of which are both herein specifically incorporated by reference in their entirety.

This invention was made with government support under Grant No. Z01 BC010484 awarded by the National Institutes of Health. The government has certain rights in the invention.

BACKGROUND OF THE INVENTION

1. Field of the Invention

The present invention relates generally to the fields of molecular biology, immunology and oncology. More particularly, it concerns the development of monoclonal antibodies and fragments thereof and their use in the prevention and therapy of diseases associated with abnormal vascular proliferation, such as cancer.

2. Description of Related Art

Tumor markers are substances produced by tumor cells or by other cells of the body in response to cancer. These substances can be found in the blood, in the urine, in the tumor tissue, or in other tissues, such as the surrounding tissues including the vasculature that feeds the tumor. Different tumor markers are found in different types of cancer, and levels of the same tumor marker can be altered in more than one type of cancer. In addition, tumor marker levels are not altered in all people with cancer, especially if the cancer is early stage. Some tumor marker levels can also be altered in patients with non-cancerous conditions. As such, tumor markers are highly useful in diagnostic procedures, and in certain cases, can even be used as therapeutic targets, i.e., to allow a therapy to discriminate between diseased and healthy tissues.

One successful example of a tumor marker that has been used to target a cancer therapy is the proto-oncogene human epidermal growth factor receptor 2 (HER-2; also known as neu and ErbB-2). Epidermal growth factor receptors are proteins embedded in the cell membrane that help regulate cell growth, survival, adhesion, migration, and differentiation. These functions are amplified in some cancers, notably some breast cancers, in which there is an amplification of the HER-2 gene or over-expression of its protein product, which causes breast cells to reproduce uncontrollably. Antibodies to the protein HER-2, such as HERCEPTIN, are currently used to treat breast cancer.

Another way of exploiting tumor markers is to attack molecules with which the marker interacts. For example, vascular endothelial growth factor receptor (VEGFR) is often up-regulated in vascular tissue surrounding tumors, and tumor cells can secrete excess VEGF. As a result, blood vessel growth proceeds in an uncontrolled fashion, much like the growth of the tumor. The anti-VEGF antibody, Bevacizumab, binds to VEGF and prevents it from interacting with its cognate receptor. This in turn results in impaired blood vessel development surrounding the tumor, thereby limiting tumor growth. However, just as with many other cancer therapies, not all cancers and not all patients will respond to these kinds of treatments. One of the limitations of current tumor marker strategies in cancer therapy is that these therapies cannot separate physiological and pathological angiogenesis. Consequently, various effects associated with the use of these agents have been reported (Higa and Abraham, 2009).

Tumor endothelial Marker 8 (TEM8), an 85 kDa integrin-like cell surface receptor, was originally identified as one of several unrelated genes (called TEM1-TEM9) overexpressed in vascular endothelial cells derived from tumor versus normal colorectal tissues (St Croix et al., 2000). Subsequent studies have shown that TEM8 is overexpressed in the blood vessels of a variety of human cancer types (St Croix et al., 2000; Nanda et al., 2004).

Insights into the physiological functions of TEM8 are beginning to emerge. In vitro studies suggest that TEM8 can bind collagens, such as collagen I and collagen VI which, in turn, can promote the migration of endothelial cells (Nanda et al., 2004; Hotchkiss et al., 2005). Migration of cells on extracellular matrix is dependent on actin cytoskeleton reorganization, and recent studies suggest that the TEM8 cytosolic domain may link extracellular matrix molecules to the actin cytoskeleton (Werner et al., 2006; Go et al., 2009). However, it is unclear which components of the actin cytoskeleton are involved in binding TEM8 under physiological conditions, and how this binding contributes to TEM8 function. TEM8 may also be involved in collagen uptake through an endocytosis-mediated degradation pathway, as TEM8 knockout mice are viable but display an excess buildup of collagen in select organs (Cullen et al., 2009).

TEM8 shares 58% amino acid identity with CMG2, another cell surface receptor that binds extracellular matrix (ECM) proteins, in this case laminin and collagen type IV (Bell et al., 2001). Both TEM8 and CMG2 share an integrin-like von Willebrand factor A domain in their extracellular region. TEM8 and CMG2 have both been found to bind anthrax toxin proteins (Bradley et al., 2001; Scobie et al., 2003), and have therefore been given the alternative names anthrax toxin receptor 1 (ANTXR1) and ANTXR2, respectively. Protective antigen (PA) is the subunit of anthrax toxin responsible for binding TEM8 or CMG2, and the PA-receptor interaction is critical for toxin entry into cells. TEM8 is highly conserved, and mouse TEM8 protein, which shares 98% amino acid identity with human TEM8, is also overexpressed in mouse tumor vessels (Carson-Walter et al., 2001).

TEM8 is unique among the original TEMs identified in that it has not been found to be detected in the angiogenic vessels of adult ovaries, and in TEM8$^{-/-}$ knockout mice developmental angiogenesis appeared unaffected (St Croix et al., 2000; Nanda et al., 2004; Cullen et al., 2009). However, in tumor challenge studies tumor growth was impaired in TEM8 knockout compared to wild-type mice (Cullen et al., 2009).

SUMMARY OF THE INVENTION

Antibodies made using traditional approaches—peptides or purified antigens—failed to recognize the normal cell surface form of TEM8 because the predominant form of TEM8 that is expressed on the cell surface is in fact concealed by two cellular factors, alpha-smooth muscle actin and transgelin, both of which play an important role in the actin cytoskeleton. Using an innovative approach, the applicants have produced a new anti-TEM8 antibody that is able to recognize the predominant form of TEM8 on the surface of live cells, independent of the conformational status of TEM8.

The applicants' further recognized that host-derived TEM8 promotes pathological but not physiological angiogenesis. Knowing that improved therapies targeting tumor and tumor-related antigens are needed, applicants further recognized that targeting TEM8 could be an effective strategy for combating cancers which are dependent upon angiogenesis for survival.

Embodiments are based in part on the inventors' identification of certain antibodies and antibody fragments that bind to native cell surface-expressed TEM8, and the finding that these antibodies and fragments, as well as chimeric antibodies that include the antibodies or fragments that bind to native cell surface-expressed TEM8), have application in the treatment or prevention (or both) of diseases associated with abnormal vascular proliferation. These antibodies and antibody fragments have the ability to selectively target abnormal vasculature through their ability to bind to native cell surface-expressed TEM8.

Thus, the present invention in part includes isolated and purified antibodies or antibody fragments that bind immunologically to native cell-surface expressed TEM8. The antibody may be of any type, such as an IgG or IgM antibody.

In some embodiments, the antibody or antibody fragment may be chimeric, wherein a "chimeric" antibody is defined as an antibody that includes a fragment from one species fused with a fragment from another species. In more particular embodiments, the chimeric antibody is humanized. A humanized chimeric antibody is an antibody including a human fragment and a fragment from another species. The antibody may be a single chain antibody. In other embodiments, the antibody or antibody fragment is bivalent.

The humanized antibody may include a non-human variable region that binds to native cell surface-expressed TEM8 on a human cell, and a human constant chain region. For example, the antibody may include a light chain variable region sequence of a mouse anti-TEM8 antibody encoded by SEQ ID NO:34 or a heavy chain variable region sequence of a mouse anti-TEM8 antibody encoded by SEQ ID NO:39, or both. One non-limiting example of a human Ig kappa light chain constant region sequence that may be included in a humanized antibody of the present invention is the sequence encoded by SEQ ID NO:35. Non-limiting examples of human Ig kappa heavy chain constant region sequences that may be included in a humanized antibody of the present invention includes sequences encoded by SEQ ID NO:40 (heavy chain constant region CH1), SEQ ID NO:41 (heavy chain constant region CH2), and SEQ ID NO:42 (heavy chain constant region CH3), or sequences having at least 90% sequence identity to any of SEQ ID NOs:40-42.

In one embodiment, the humanized antibody includes an amino acid sequence comprising a light chain variable region sequence of mouse anti-TEM8 antibody and a human Ig kappa light chain constant region sequence that has at least 80%, 85%, 90%, 91%, 92%, 93%, 94%, 95%, 96%, 97%, 98%, or 99% sequence identity to SEQ ID NO:36. In a particular embodiment, the humanized antibody includes SEQ ID NO:36. The humanized antibody may include at least 50, at least 70, at least 90, and least 120, at least 150, or at least 180 contiguous amino acids of SEQ ID NO:36.

The antibody sequence of SEQ ID NO:36 is encoded by plasmid Plasmid #1: pAN6525-VL, and the nucleic acid sequence of this plasmid is set forth in SEQ ID NO:33. SEQ ID NO:34: is the nucleic acid encoding a signal peptide and light chain variable region sequence of mouse anti-TEM8 antibody that is included in this antibody, and SEQ ID NO:35 is the nucleic acid encoding human Ig kappa light chain constant region sequence of this antibody.

In one embodiment, the humanized antibody includes an amino acid sequence comprising a heavy chain variable region sequence of mouse anti-TEM8 antibody and a human Ig kappa heavy chain constant region sequence that has at least 80%, 85%, 90%, 91%, 92%, 93%, 94%, 95%, 96%, 97%, 98%, or 99% sequence identity to SEQ ID NO:43. In a particular embodiment, the humanized antibody includes SEQ ID NO:43. The humanized antibody may include at least 50, at least 100, at least 150, and least 200, at least 250, at least 300, at least 350, at least 400, or at least 450 contiguous amino acids of SEQ ID NO:43.

The antibody of SEQ ID NO:43 is encoded by plasmid Plasmid #2: pAH6307-VH, and the nucleic acid sequence of this plasmid is set forth in SEQ ID NO:38. SEQ ID NO:39: is the nucleic acid encoding a signal peptide and heavy chain variable region sequence of mouse anti-TEM8 antibody that is included in this antibody, and SEQ ID NOs:40, 41, and 42 are nucleic acid sequences encoding human Ig kappa heavy chain constant region CH1, CH2, and CH3 sequences of this antibody, respectively. SEQ ID NO:44 is the nucleic acid encoding the IgG1 hinge. The antibodies or fragments of the present invention may comprise IgG1 sequences that have at least 90% sequence identity to any of the aforementioned sequences.

In a particular embodiment, a humanized antibody of the present invention may comprise a light chain amino acid sequence that includes SEQ ID NO:36 and a heavy chain amino acid sequence that includes SEQ ID NO:43. In a more particular embodiment, the chimeric antibody is a heterotetramer that contains two identical heavy chains and two identical light chains, such as two identical heavy chains comprising SEQ ID NO:43 and two identical heavy chains comprising SEQ ID NO:36. Human 293-HEK cells that make this antibody (herein designated cAF334) have been deposited with the ATCC on Jun. 8, 2011 (ATCC Patent Deposit Designation PTA-11937).

In some embodiments, a humanized antibody or a fragment thereof includes a variable heavy chain ($V_H$) domain or a variable light chain ($V_L$) domain, or both. The $V_H$ domain may comprise an amino acid sequence that includes one, two or three complementarity determining regions (CDRs) selected from the group consisting of the following: a CDR1 sequence comprising an amino acid sequence having at least 20%, 40%, 60%, 80% or 100% sequence identity to the sequence of SEQ ID NO: 45; a CDR2 sequence comprising an amino acid sequence having at least 5%, 11%, 17%, 23%, 29%, 35%, 41%, 47%, 52%, 58%, 64%, 70%, 76%, 82%, 88%, 94%, or 100% sequence identity to the sequence of SEQ ID NO: 46; and a CDR3 sequence comprising an amino acid sequence having at least 11%, 22%, 33%, 44%, 55%, 66%, 77%, 88% or 100% sequence identity to the sequence of SEQ ID NO: 47. The $V_L$ domain may comprise an amino acid sequence that includes one, two or three complementarity determining regions (CDRs) selected from the group consisting of the following: a CDR4 sequence comprising an amino acid sequence having at least 7.5%, 15%, 23%, 30%, 38%, 46%, 53%, 61%, 69%, 76%, 84%, 92% or 100% sequence identity to the sequence of SEQ ID NO: 48; a CDR5 sequence comprising an amino acid sequence having at least 14%, 28%, 42%, 57%, 71%, 85% or 100% sequence identity to the sequence of SEQ ID NO: 49; and a CDR6 sequence comprising an amino acid sequence having at least 9%, 18%, 27%, 36%, 45%, 54%, 63%, 72%, 81%, 90% or 100% sequence identity to the sequence of SEQ ID NO: 50.

The antibody fragment may be any antibody fragment that retains the ability to bind immunologically to native cell-surface expressed TEM8. In some embodiments, the isolated and purified antibody fragment is Fab' or F(ab')$_2$.

In some embodiments, an isolated or purified antibody having any of the SEQ ID NOs set forth herein is not the AF344 antibody. It is a recombinant or chimeric version of the AF344 antibody such that it has sequences from AF344 but less than 100% of the sequences. In certain embodiments an isolated or purified antibody has, has at least, or has at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, or 99.9 percent identity (or any range derivable therein) to AF344, but is not AF344. In certain embodiments, the TEM-8 antibody that binds native TEM-8 has sequences from 1, 2, 3, 4, 5, 6 or more SEQ ID NOs discussed herein, but does not have the entire sequence of AF344.

In particular embodiments, the antibody or antibody fragment is conjugated to a therapeutic agent or a diagnostic agent. The diagnostic agent may be a detectable label. The detectable label may be of a type that can be utilized for in vitro detection. In other embodiments, the detectable label can be utilized for in vivo imaging. For example, the detectable label may be a radionuclide. Numerous other examples of detectable labels are discussed elsewhere in this specification.

In some embodiments, an antibody fragment of the present invention is fused to a polypeptide that is a therapeutic agent or drug, resulting in a fusion protein. In some embodiments, the fusion protein comprises any of the heavy chain variable regions or light chain variable regions set forth herein fused to the extracellular domain of a growth factor receptor. Non-limiting examples of growth factor receptors include Vascular Endothelial Growth Factor Receptor (VEGFR) 1, VEGFR-2, VEGFR-3, Fibroblast Growth Factor Receptor (FGFR) 1, FGFR-2, FGFR-3, FGFR-4, a nerve growth factor receptor (e.g., ciliary neurotrophic factor receptor), Transforming Growth Factor (TGF)-beta 1 receptor, TGF-beta 2 receptor, insulin-like growth factor 1 receptor, insulin-like growth factor 2 receptor, platelet-derived growth factor receptor A, and platelet-derived growth factor receptor B. In some embodiments, the extracellular domain has at least 90, 91, 92, 93, 94, 95, 96, 97, 98, or 99% sequence identity to SEQ ID NO:51 (RNLTIRRVRKEDE-GLYTCQACSVL) or SEQ ID NO:52 (STLFIERVTEEDE-GVYHCKATNQK).

In some embodiments, the antibody or antibody fragment of the present invention is conjugated to a therapeutic agent or a drug. Anti-TEM8 antibody drug conjugates may facilitate selective destruction of tumor blood vessels and thereby enhance anti-cancer efficacy of the agent or drug and reduce normal tissue toxicities. Non-limiting examples of drugs include a chemotherapeutic, a radiotherapeutic, a thrombogenic agent, an immunomodulatory domain, a lymphocyte binding domain, or a toxin.

In other embodiments, the antibody or antibody fragment may be conjugated to a drug that is dolastatin/auristatin or an analog of dolastatin/auristatin. These agents have been shown to interfere with microtubule dynamics, GTP metabolism, and cell division. Examples of drugs of similar to dolastatin/auristatin are described in U.S. Pat. Nos. 5,635,483; 5,780,588; 5,663,149; 7,964,566; and U.S. Patent Application Pub. No. 2011/0020343 (U.S. Ser. No. 12/933,364, each of which is herein specifically incorporated by reference in its entirety).

In some embodiments, the drug with similarity to dolastatin/auristatin may be of the formula I or II:

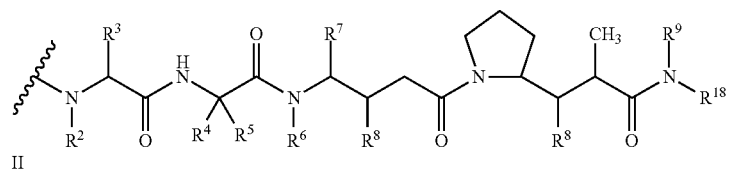

Formula I

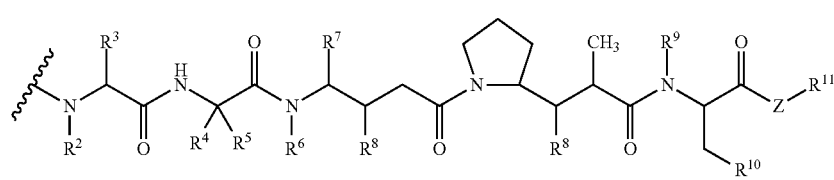

Formula II wherein, independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)rn$-$R^{14}$, or —$(R^{13}O)_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, $-(CH_2)_n-N(R^{16})_2$, $-(CH_2)_n-SO_3H$, or $-(CH_2)_n-SO_3-C_1-C_8$ alkyl;

each occurrence of $R^{16}$ is independently H, $C_1-C_8$ alkyl, or $-(CH_2)_n-COOH$;

$R^{18}$ is selected from $-C(R^8)_2-C(R^8)_2$-aryl, $-C(R^8)_2-C(R^8)_2-(C_3-C_8$ heterocycle), and $-C(R^8)_2-C(R^8)_2-(C_3-C_8$ carbocycle); and n is an integer ranging from 0 to 6.

and pharmaceutically acceptable salts or solvents thereof, wherein MMAE is monomethyl auristatin E (N-methylvaline-valine-dolaisoleuine-dolaproine-norephedrine), and MMAF is monomethyl auristatin F (N-methylvaline-valine-dolaisoleuine-dolaproine-phenylalanine).

In other embodiments, the drug with similarity to dolastatin/auristatin may be of formula V, as further detailed in U.S. Patent Application Pub. No. 2011/0020343, herein specifically incorporated by reference:

Formula V

In one embodiment, $R^3$, $R^4$ and $R^7$ are independently isopropyl or sec-butyl and $R^{15}$ is —H. In an exemplary embodiment, $R^3$ and $R^4$ are each isopropyl, $R^{15}$ is H. and $R^7$ is sec-butyl.

In another embodiment, $R^2$ and $R^6$ are each methyl, and $R^9$ is H.

In still another embodiment, each occurrence of $R^8$ is —OCH$_3$

In an exemplary embodiment, $R^3$ and $R^4$ are each isopropyl, $R^2$ and $R^6$ are each methyl, $R^{15}$ is H, $R^7$ is sec-butyl, each occurrence of $R^8$ is —OCH$_3$, and $R^9$ is H.

In one embodiment, Z is —O— or —NH—.

In one embodiment, $R^{10}$ is aryl In an exemplary embodiment, $R^{10}$ is -phenyl.

In an exemplary embodiment, when Z is —O—, $R_{11}$ is H, methyl or t-butyl.

In one embodiment, when Z is —NH, $R_{11}$ is —CH(R$_{15}$)$_2$, wherein $R_{15}$ is —(CH$_2$)$_n$—N(R$_6$)$_2$, and $R_{16}$ is —C$_1$-C$_8$ alkyl or —(CH$_2$)$_n$—COOH.

In another embodiment, when Z is —NH, $R_{11}$ is —CH(R$_{15}$)$_2$, wherein $R_{15}$ is —(CH$_2$)$_n$—SO$_3$H.

Illustrative Drug units (-D) include the drug units having the following Structures:

wherein the wavy line indicates the attachment to a Linker unit (LU);

$R^1$ and $R^2$ is independently selected from the group consisting of hydrogen (H) and —C$_1$-C$_8$ alkyl; with the proviso that both $R^1$ and $R^2$ are not H;

$R^3$ is selected from the group consisting of H, —C$_1$-C$_8$ alkyl, —C$_3$-C$_8$ carbocycle, aryl, —X$^1$-aryl, —X$^1$—(C$_3$-C$_8$ carbocycle), —C$_3$-C$_8$ heterocycle and —X$^1$—(C$_3$-C$_8$ heterocycle);

$R^4$ is selected from the group consisting of H, —C$_1$-C$_8$ alkyl, —C$_3$-C$_8$ carbocycle, -aryl, —X$^1$-aryl, —X$^1$—(C$_3$-C$_8$ carbocycle), —C$_3$-C$_8$ heterocycle and —X$^1$—(C$_3$-C$_8$ heterocycle);

$R^5$ is selected from the group consisting of H and methyl;

or $R^4$ and $R^5$ jointly form a carbocyclic ring and have the formula —(CR$^a$R$^b$)$_n$—, wherein $R^a$ and $R^b$ are independently selected from the group consisting of H and —C$_1$-C$_8$ alkyl and n is selected from the group consisting of 2, 3, 4, 5 and 6;

$R^6$ is selected from the group consisting of H and —C$_1$-C$_8$ alkyl;

Formula III

MMAE

Formula IV

MMAF $R^7$ is selected from the group consisting of H, —$C_1$-$C_8$ alkyl, —$C_3$-$C_8$ carbacycle, aryl, —$X^1$-aryl, —$X^1$—($C_3$-$C_8$ carbocycle), —$C_3$-$C_8$ heterocycle and —$X^1$—($C_3$-$C_8$ heterocycle);

each $R^8$ is independently selected from the group consisting of H, —OH, —$C_1$-$C_8$ alkyl, —$C_3$-$C_8$ carbacycle and —O—($C_1$-$C_8$ alkyl);

$R^{12}$ is selected from H, —$C_1$-$C_8$ alkyl, aryl, —$X^1$ aryl, —$C_3$-$C_8$ carbocycle, —$X^1$—($C_3$-$C_8$ carbocycle), —$C_1$-$C_8$ alkylene-$NH_2$, —$C_3$-$C_8$ heterocycle and —$X^1$—($C_3$-$C_8$ heterocycle); and each $X^1$ is independently —$C_1$-$C_{10}$ alkylene;

or a pharmaceutically acceptable salt or solvate thereof.

In some embodiments, $R^4$ and $R^{12}$ are each independently selected from a side chain of a natural amino acid. In some embodiments, $R^{12}$ is the side chain of phenylalanine. In some embodiments, $R^{12}$ is the side chain of methionine. In some embodiments, $R^{12}$ is the side chain of tryptophan.

In some embodiments, the antibody or antibody fragment of the present invention ("Ab") is conjugated to the drug unit via a linker to provide a drug-linker-Ab conjugate. A "linker" refers to a moiety that connects a first molecule to a second molecule through chemical bonds. A linker can be used to link a drug unit and an antibody or antibody fragment to form a drug-linker-antibody (or antibody fragment) conjugate. Various non-limiting examples of linker units are set forth in U.S. Pat. Nos. 5,635,483; 5,780,588; 5,663,149; 7,964,566; and U.S. Patent Application Pub. No. 2011/0020343 (U.S. Ser. No. 12/933,364), each of which is herein specifically incorporated by reference in its entirety). The antibody or antibody fragment of the present invention may include a functional group which can form a bond with a functional group of the linker. Non-limiting examples of useful functional groups include sulfhydryl (—SH), amino, hydroxyl, carboxy, the anomeric hydroxyl group of a carbohydrate, and carboxyl. The linker may optionally include a "stretcher" unit as defined in U.S. Pat. No. 7,964,566, herein specifically incorporated by reference.

In some embodiments, the linker includes one or more amino acid moieties. For example, the linker may include a dipeptide, a tripeptide, a tetrapeptide, a pentapeptide, a hexapeptide, a heptapeptide, an octapeptide, a nonapeptide, a decapeptide, an undecapeptide, or a dodecapeptide unit. The linker may optionally comprise valine-citrulline, phenylalanine-lysine, N-methylvaline-citrulline, 5-aminovaleric acid, homo phenylalanine lysine, tetraisoquinolinecarboxylate lysine, cyclohexylalanine lysine, isonepecotic acid lysine, beta-alanine-lysine, glycine serine valine glutamine and isonepecotic acid. The amino acids may be natural amino acids or non-natural amino acids.

If the linker comprising one or more amino acid moieties, a spacer unit may optionally link an amino acid moiety to the drug moiety. Non-limiting examples of spacers include those set forth in U.S. Pat. No. 7,964,566, herein specifically incorporated by reference. The spacer unit may be self-immolative or non self-immolative. A non self-immolative spacer unit is one in which part or all of the spacer unit remains bound to the drug moiety after cleavage, particularly enzymatic, or an amino acid unit from the drug-linker-ab conjugate. An example includes glycine-glycine, or glycine. In another embodiment, the spacer is a p-aminobenzyl alcohol (PAB) unit, whose phenylene portion is substituted with Qm, wherein Q is —$C_1$-$C_8$ alkyl, —O—($C_1$-$C_8$ alkyl), -halogen, -nitro, or -cyano, and m is an integer ranging from 0 to 4. Other examples of spacers include PAB variants such as 2-aminoimidazol-5-methanol derivatives, and ortho or para-aminobenzylacetals, and franched bis (hydroxylmethyl)styrenes.

In some aspects, compounds of formula VI are provided:

Ab﹙L-D﹚p                                   Formula VI:

or a pharmaceutically acceptable salt or solvate thereof, wherein Ab is an antibody or antibody fragment of the present invention which binds immunologically to native cell-surface expressed TEM8, L is a linker unit, D is a drug unit, and p ranges from 1 to about 20. In certain embodiments, the drug unit is of formula I, formula II, formula III, formula IV, or formula V.

In some aspects the auristatin (such as MMAF) is conjugated to the antibody or antibody fragment at the N-terminal amino acid of the auristatin via a cathepsin B cleavable peptide linker maleimidocaproyl-valine-citrulline (mc-vc-) and a self-immolative group p-aminobenzyl-carbamoyl (PABC) to produce antibody or fragment ("ab")-linker-drug conjugates of the structure ab-mc-vc-PABC-auristatin. Upon release of the peptide linker, the PABC group releases itself from the auristatin resulting in release of free drug. In one specific example, the conjugate is of formula ab-mc-vc-PABC-MMAF.

In a specific embodiment, the conjugate of the present invention is of formula VII or formula VIII.

Formula VII

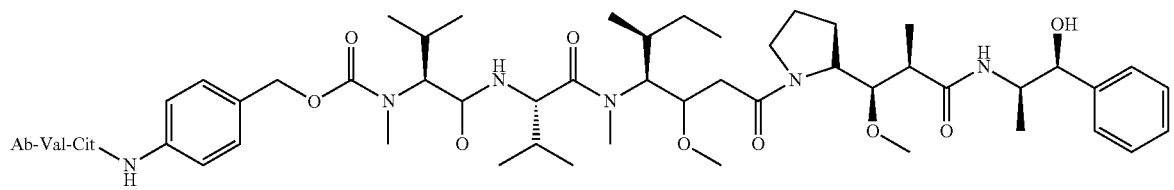

Ab-Val-Cit-PABC spacer-MMAE

-continued

Formula VIII

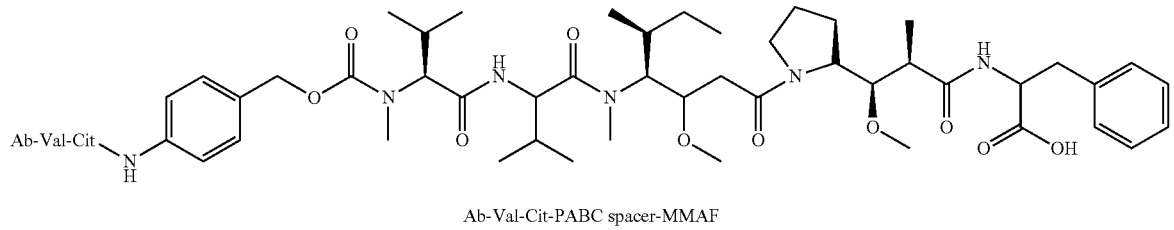

Ab-Val-Cit-PABC spacer-MMAF

In other embodiments, the antibody or antibody fragment is conjugated to a drug that is maytansine or a derivative of maytansine. A linker moiety may optionally link the drug to the maytansine or derivative of maytansine. Maytansine is an antimitotic agent that inhibits tubulin polymerization, thus interfering with the formation of microtubules in the cell nucleus. It may also inhibit DNA, RNA, and protein synthesis, with most effect on DNA synthesis. Information concerning maytansine and derivatives of maytansine and drug conjugates using these molecules can be found in U.S. Pat. Nos. 7,514,080; 7,501,120; 7,494,649; 7,374,762; 6,441,163; and U.S. Patent Application Pub. No. 2003/0109682, each of which is herein specifically incorporated by reference in its entirety. In some embodiments the derivative of maytansine is emtansine (4-(3-mercapto-2,5-dioxo-1-pyrrolidinylmethyl)-cylohexanecarboxylic acid) or mertansine (.N$_2$'-deacetyl-N$_2$'-(3-mercapto-1-oxopropyl)-maytansine). Maytansine and selected derivatives are shown in Formula IX.

Formula IX

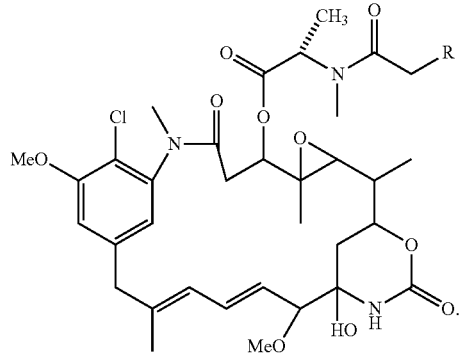

Maytansines are of the following general formula:

Formula X

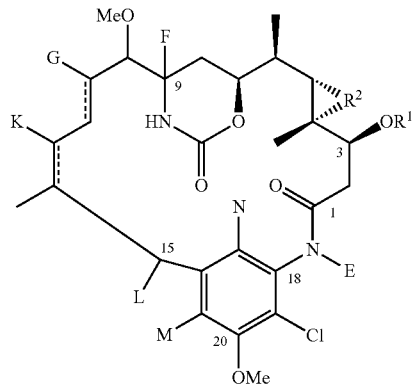

wherein $R^1$ is H or acyl; $R^2$ is O or a bond; E is H or $C_1$-$C_4$ alkyl; F is an oxygen, nitrogen, or sulfur atom; G and K are independently H or OH; L is H or OH; and M and N are independently H, OH, or $NH_2$. Preferred examples of ansamitocins include but are not limited to maytansine, maytanbutine ($R^4$=isopropyl), maytanprine ($R^4$=ethyl), maytanvaline ($R^4$=isobutyl), maytansinol, ansamitocin P0, ansamitocin P1, ansamitocin P2, ansamitocin P3, ansamitocin P3', and ansamitocin P4.

In some embodiments, the conjugate of the present invention is of formula XI:

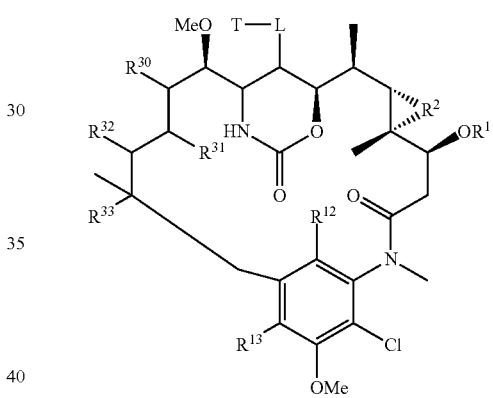

Wherein T is an antibody or antibody fragment of the present invention, L is a linker, $R^1$ is H, C(=O)$R^4$, or C(=O)—CHMe-N(Me)—C(=O)—$R^4$, wherein $R^4$ is C1-C6 straight or branched alkyl;

$R^2$ is O or a bond;

$R^{12}$ and $R^{13}$ are each independently H, OH, or $NH_2$; and $R^+$ is OH, $R^{31}$ is H, and $R^{32}$ and $R^{33}$ together form a bond, or $R^{32}$— is OH, $R^{33}$ is H, and $R^{30}$ and $R^{31}$ together form a bond.

The linker may be any of the aforementioned linkers. In particular embodiments, the linker is of Formula XII, XIII, or XIV:

Formula XII

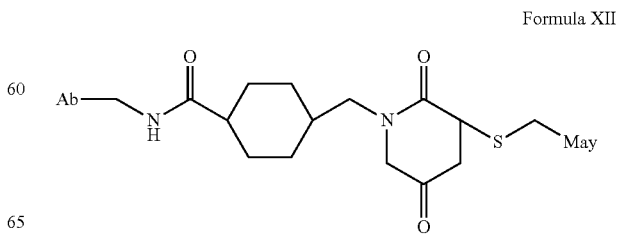

wherein May represents maytansine or a derivative of maytansine.

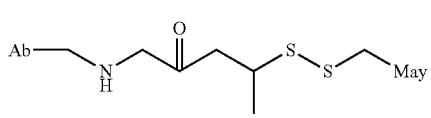

Formula XIII wherein May represents maytansine or a derivative of maytansine.

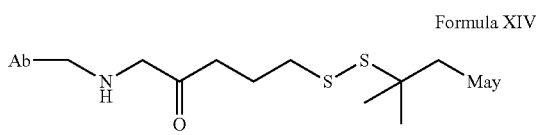

Formula XIV wherein May represents maytansine or a derivative of maytansine.

Other specific examples of linkers are set forth in U.S. Pat. Nos. 7,514,080; 7,501,120; 7,494,649; 7,374,762; 6,441,163; and U.S. Patent Application Pub. No. 2003/0109682, each of which is herein specifically incorporated by reference in its entirety. In some embodiments the linker allows the maytansine or maytanine derivative to be linked to a lysine residue of the antibody or antibody fragment. Three examples of linkers for maytansine or maytansine derivatives are set forth below. Additional information regarding linker design for conjugates that include maytansine or a maytansine derivative can be found in Phillips et al., 2008 Cancer Res. 68, 9280; Ikeda et al., 2009 Clin. Cancer Res. 15, 4028, and Chen et al., 2007 Clin. Cancer Res. 13, 2689, each of which is herein specifically incorporated by reference.

In other embodiments, the antibody or antibody fragment is conjugated to a drug that is a calicheamicin. Calicheamicins are enediyne antibiotics that are toxic to cells, and have been used as targeted therapy against cancer. Two examples of calicheamicins include calicheamicin γ1, N-acetyl gamma calicheamicin, and esperamicin, depicted in Formula XV, Formula XVI, and Formula XVII, respectively below.

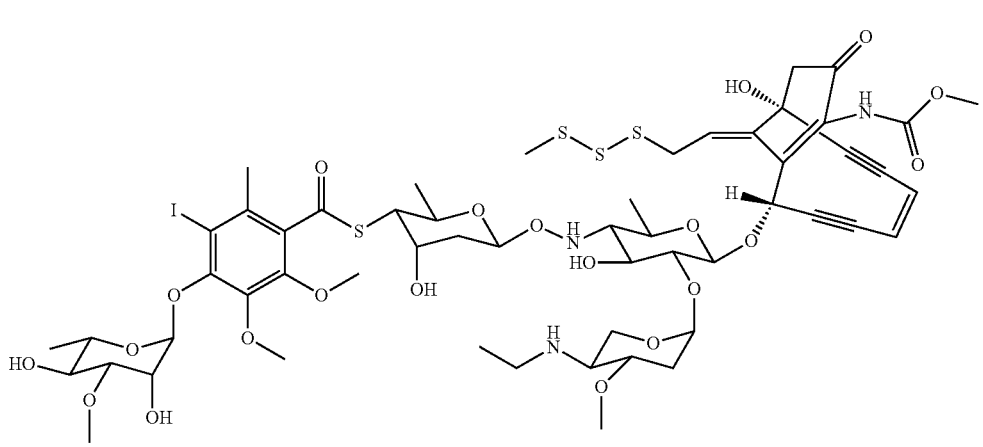

Formula XV

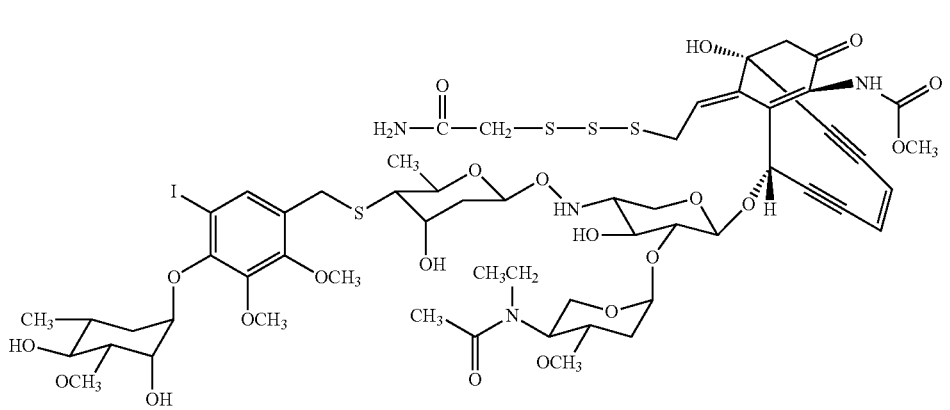

Formula XVI

-continued

Formula XVII

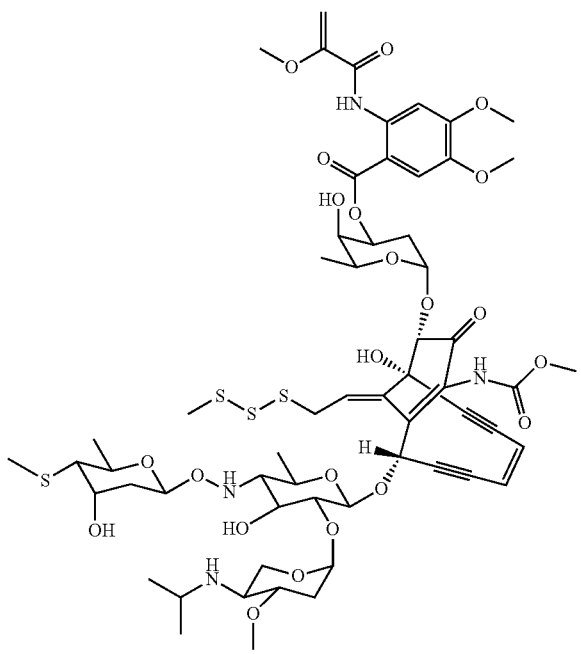

In some embodiments, a linker is used to conjugate the calicheamicin to the antibody or antibody fragment. The linker may be capable of releasing the cytotoxic drug from the conjugate after binding and entry into target cells. In a specific embodiment, the linker is 4-(4-acetylphenoxy) butanoic acid (AcBut), as set forth in Formula XVIII.

Formula XVIII

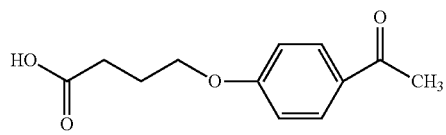

4-(4-acetylphenoxy)butnoid acid

Additional information concerning calicheamicins and calicheamicin conjugates can be found in U.S. 20090105461, U.S. 20060002942, US20070213511, US20040192900, U.S. Pat. Nos. 5,739,116,5,550,246, and 5,714,586, each of which is herein specifically incorporated by reference in its entirety.

In particular embodiments, the antibody or antibody fragment comprises a light chain variable region sequence having at least 70%, at least 75%, at least 80%, at least 85%, at least 90%, at least 95%, at least 99% or greater sequence identity to SEQ ID NO: 1. In some embodiments, the light chain variable region of the antibody or antibody fragment comprises SEQ ID NO:1. In some embodiments, the antibody or antibody fragment comprises a heavy chain variable region sequence having at least 70%, at least 75%, at least 80%, at least 85%, at least 90%, at least 95%, at least 99% or greater sequence identity to SEQ ID NO: 2. and a heavy chain variable region sequence of SEQ ID NO:2. In some embodiments, the heavy chain variable region of the antibody or antibody fragment comprises SEQ ID NO:2. In further embodiments, the antibody or antibody fragment comprises a light chain variable region sequence having at least 70%, at least 75%, at least 80%, at least 85%, at least 90%, at least 95%, at least 99% or greater sequence identity to SEQ ID NO: 1 and a heavy chain variable region sequence having at least 70%, at least 75%, at least 80%, at least 85%, at least 90%, at least 95%, at least 99% or greater sequence identity to SEQ ID NO: 2. In a particular embodiment, the antibody or antibody fragment comprises a light chain variable region comprising SEQ ID NO:1, and a heavy chain variable region comprising SEQ ID NO:2. In a specific embodiment, the antibody or antibody fragment comprises a light chain variable region consisting of SEQ ID NO:1, and a heavy chain variable region consisting of SEQ ID NO:2. In another specific embodiment, the isolated and purified antibody is AF334.

Some non-limiting examples of classes of drugs that can be conjugated to the antibodies or antibody fragments of the present invention (with or without a linker) include a toxin, an immunomodulatory domain (e.g., IL2), a lymphocyte binding domain (e.g., anti-CD3) or a thrombogenic peptide. Non-limiting examples of toxins include gelonin, maize RIP, saporin, ricin, ricin A chain, barley RIP, momordin, alpha-momorcharin, beta-momorcharin, Shiga-like RIP, an a-sarcin, abrin, an aquatic-derived cytotoxin, *Pseudomonas* exotoxin, a DNA synthesis inhibitor, a RNA synthesis inhibitor, a prodrug, a light-activated porphyrin, trichosanthin, tritin, pokeweed antiviral protein, mirabilis antiviral protein (MAP), Dianthin 32, Dianthin 30, bryodin, shiga, diphtheria toxin, diphtheria toxin A chain, dodecandrin, tricokirin, bryodin and luffin. Non-limiting examples of thrombogenic peptides include tissue factor peptides, as discussed in greater detail elsewhere in this specification.

The invention also includes hybridoma cells producing antibodies or antibody fragments that bind immunologically to native cell-surface expressed TEM8. The antibody may be any of the foregoing antibodies. In a specific embodiment, the antibody is AF334. Cells from the AF334 mouse hybridoma were deposited with ATCC on Nov. 4, 2010 (ATCC Patent Deposit Designation PTA-11454).

The invention also includes cells to which an anti-TEM8 antibody of the present invention is attached. In a particular embodiment, the cell is a T cell.

Also disclosed is a polyclonal antiserum, comprising one or more antibodies or antibody fragments of the present invention.

Compositions comprising one or more antibodies or antibody fragments or cells of the present invention are also disclosed, wherein the composition includes one or more antibodies or antibody fragments of the present invention dispersed in a physiologically acceptable medium, buffer, or diluent. Examples of physiologically acceptable media, buffers, and diluents are well-known to those of ordinary skill in the art, and some are disclosed elsewhere in this specification.

In still other aspects, the invention provides compositions comprising an effective amount of an antibody (or antibody fragment)-drug conjugate and a pharmaceutically acceptable carrier or vehicle.

In another aspects, the invention provides pharmaceutical compositions comprising an effective amount of a drug-linker-antibody (or antibody fragment) conjugate and a pharmaceutically acceptable carrier or vehicle.

In still another aspect, the invention provides for compositions comprising an effective amount of a drug-antibody (or antibody fragment) conjugate having a cleavable drug unit (moiety) from the drug-antibody conjugate and a pharmaceutically acceptable carrier or vehicle.

Also included in the present invention are kits that include a container having disposed therein an antibody or antibody fragment or conjugate of the present invention that binds immunologically to native cell-surface expressed TEM8. The antibody or antibody fragments may optionally be fused to a therapeutic agent or a detectable marker, or both a therapeutic agent and a detectable marker. The kit may optionally include one or more secondary therapeutic agents directed to the treatment of a disease associated with abnormal angiogenesis.

The present invention also includes methods of imaging tumor vasculature comprising administering to a subject having a vascularized tumor an antibody or antibody fragment of the invention that binds immunologically to native cell-surface expressed TEM8, wherein said antibody is conjugated to an detectable label. In one embodiment, the antibody is an IgG antibody.

Also disclosed are methods of treating a subject with a disease associated with abnormal vascularization comprising administering to said subject an antibody, antibody fragment, or conjugate of the present invention. In some embodiments, the subject has a vascularized tumor. Non-limiting examples of tumors include a brain tumor, an ocular tumor, a head & neck tumor, a skin tumor, a lung tumor, an esophageal tumor, a pancreatic tumor, a stomach tumor, a liver tumor, a prostate tumor, a colon tumor, a rectal tumor, a breast tumor, an ovarian tumor, a uterine tumor, a cervical tumor, a lymphoma, or a testicular tumor. Other examples of tumors are discussed elsewhere in this specification. In some embodiments, the subject has recurrent cancer, metastatic cancer or multi-drug resistant cancer. In particular embodiments, the tumor includes endothelial cells expressing native cell surface TEM8. In other embodiments, the subject has an ophthalmic disease associated with abnormal vascularization. For example, the ophthalmic disease may be corneal neovascularization, neovascularization of the iris, or macular degeneration (such as age-related macular degeneration associated with neovascularization). In particular embodiments, the ophthalmic disease includes vascular endothelial cells that express cell surface TEM8.

The composition that includes the antibodies or antibody fragments of the present invention may be administered by any method known to those of ordinary skill in the art. Administration may be intravenous administration, injection directly into tumor vasculature, or administered into a resected tumor bed. Other examples of routes of administration are set forth elsewhere in this specification. For ophthalmic applications, examples of administration include topically, intraocularly, intravitreally, subretinally, or by sub-Tenon's injection.

The composition may be administered a single time, or multiple times to the subject. For example, the antibody or antibody fragment may be administered to the subject at least two, three, four, five, six, seven, eight, nine or ten or more times.

In some embodiments, the subject is known or suspected to have a tumor that is cancerous, and the subject is further administered a distinct secondary cancer therapy. Administration of the distinct cancer therapy may be concurrent with administration of the composition of the present invention, or it may be prior to or subsequent to administration of the composition of the present invention. Non-limiting examples of distinct cancer therapies include surgery, radiotherapy, chemotherapy, toxin therapy, dendritic cell therapy, radioimmunotherapy, cryotherapy or gene therapy. Non-limiting examples of secondary therapy for treatment of ophthalmic disease associated with abnormal vascularization include anti-VEGF therapy, laser photocoagulation, and vitreoretinal surgery.

In some embodiments, the method further includes evaluating the subject for expression of TEM8 on the surface of vascular endothelial cells at a site of disease in the subject. For example, the site of disease may be a tumor or other site of abnormal vascularization.

The invention also provides for methods for killing or inhibiting the multiplication or a tumor cell or cancer cell including administering to a patient in need thereof an effective amount of a drug-linker-antibody (or antibody fragment) conjugate. In another aspect, the invention provides methods for killing or inhibiting the multiplication of a tumor cell or cancer cell including administering to a patient in need thereof an effective amount of a drug-linker-antibody conjugate having a cleavable drug unit from the drug-antibody conjugate.

In yet another embodiment, the invention provides methods for treating cancer including administering to a patient in need thereof an effective amount of a drug-linker-antibody conjugate.

Further embodiments include methods of manufacturing a drug-linker-antibody (or antibody fragment) conjugate of the present invention, comprising contacting a drug-linker to an antibody (or antibody fragment), wherein a drug-linker-antibody (or antibody fragment) conjugate is formed such that said drug-linker is covalently attached to said antibody (or antibody fragment). Further embodiments include methods of manufacturing a drug-linker-antibody (or antibody fragment) conjugate of the present invention, comprising contacting a drug with a linker-antibody (or antibody fragment) conjugate to form a drug-linker-antibody (or antibody fragment) conjugate, wherein the drug is covalently attached to the linker-antibody. Compositions comprising a drug-linker or linker-antibody (or linker-antibody fragment) for use as intermediates in the manufacturing of drug-linker-antibody (or antibody fragment) conjugates are also disclosed.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features, and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawing forms part of the present specification and is included to further demonstrate certain aspects of the present invention. The invention may be better understood by reference to this drawing in combination with the detailed description of specific embodiments presented herein:

FIG. 10A—Purification of bacterially expressed GST-TEM8-ECD by GSH-Sepharose beads, 10% SDS-Page/coomassie blue staining; FIG. 10B—ELISA (glutathione-coated plate), 100 ng GST or GST-TEM8-ECD per well, G1, G2 purified from 293 cells with CDM, CHO-S: Purified from transient transfected CHO-S cells with Free-Style medium.

DESCRIPTION OF ILLUSTRATIVE EMBODIMENTS

Figures 1A, 1B:
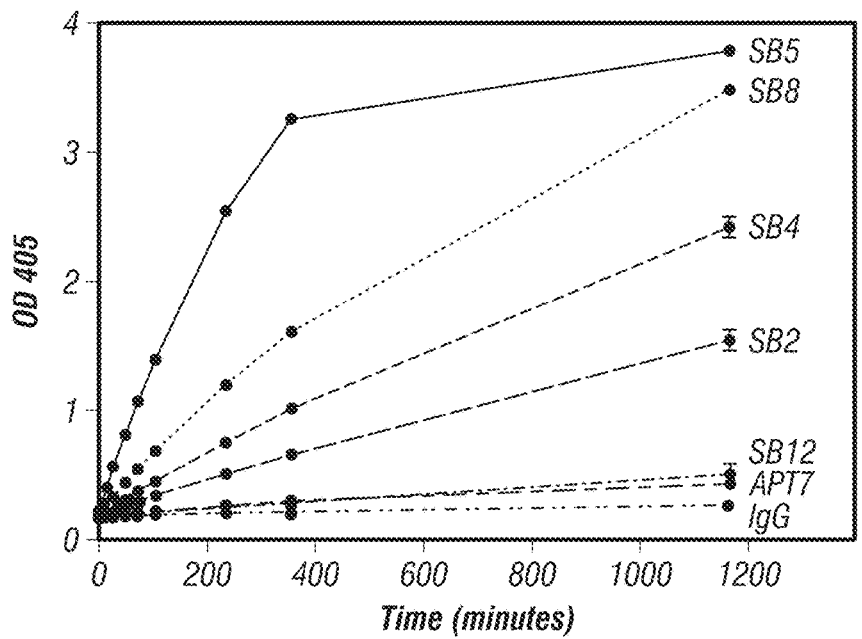
FIGS. 1A-C. SB antibodies recognize TEM8 at the cell surface following selection with SB5 antibodies. A. Table showing SB antibody isotypes, cross-reactivity with homologous proteins, and the amino acid (aa) region of TEM8 (Genbank No. AF279145; SEQ ID NO:21) containing the SB epitopes. B. ELISA used to measure reactivity of SB mAbs with soluble AP-TEM8 fusion protein. C. SB5 mAbs failed to detect TEM8 on the surface of 293 or 293/TEM8 cells by flow cytometry whereas 293/TEM8 cells selected with SB5-immunomagnetic beads (293/T8-SB5) were strongly labeled (D, upper panel). AF334 anti-TEM8 antibody was able to detect TEM8 on both 293/TEM8 and 293/T8-SB5 cells (D, lower panel).

As discussed above, improved therapies targeting tumor and tumor-related antigens are needed. In exploratory studies aimed at evaluating the potential of TEM8 as a target for antibody-based therapeutics, the inventors compared various antibodies against TEM8 including those commercially available and the so called "SB" series of anti-TEM8 mAbs developed earlier (Nanda et al., 2004). Surprisingly, none of the antibodies tested recognized the predominant form of TEM8 expressed on the cell surface, although some of the SB antibodies could recognize a cryptic population of TEM8-expressing cells. Based on its similarity to integrins, which are known to harbor both open and closed conformations, TEM8 may have more than one conformation at the cell surface, and its conformation may be regulated by the expression of other host-cell factors. Thus, the inventors set out to identify these host-cell factors by using the SB5 antibody in an unbiased genetic screen, and identified components of the actin cytoskeleton as critical dominant-acting factors capable of regulating TEM8 conformation at the cell surface.

Owing to its high expression in tumor versus normal vessels, TEM8 has been considered as a potential target for anti-tumor therapy based on an anti-angiogenic or vascular targeting approach (Nanda and St Croix, 2004). Several recent preclinical studies support the idea that TEM8 functions to promote tumor growth and that inhibition of TEM8 may represent a useful anti-tumor strategy. First, a soluble TEM8-Fc fusion protein containing the extracellular domain of TEM8 fused to the Fc region of mouse IgG was found to have potent tumoricidal activity against a variety of human tumor xenografts, presumably by competing for endogenous TEM8 ligand(s) (Duan et al., 2007). Second, DNA vaccines against TEM8 have slowed tumor growth in vivo (Ruan et al., 2009; Felicetti et al., 2007). Third, melanoma tumor growth was found to be impaired in TEM8-deficient mice (Cullen et al., 2009). Finally, anthrax toxin proteins have been shown to possess potent tumoricidal activity in a number of preclinical studies when judiciously administered at sub-toxic doses (Abi-Habib et al., 2006; Rouleau et al., 2008; Liu et al., 2003), an activity that appears to be mediated primarily through targeting of the tumor vasculature (Liu et al., 2008; Duesbery et al., 2001). Although TEM8, CMG2 or both receptors may be responsible for the anti-tumor activity of anthrax toxin proteins, antibody-based therapeutics directed against a single receptor could potentially have similar efficacy with less toxicity.

The inventors found that TEM8, in its native cell-surface expressed state is in fact "masked" by two cellular factors, α-smooth muscle actin and transgelin, both of which play an important role in the actin cytoskeleton. This provided a plausible explanation as to why antibodies made using traditional approaches—peptides or purified antigens—failed to recognize the normal cell surface form of TEM8. Using an innovative approach, the inventors produced a new anti-TEM8 antibody that is able to recognize the predominant form of TEM8 on the surface of live cells independent of its conformational status.

Thus, the present invention provides antibodies that can be delivered in the same manner as currently approved anti-cancer therapies, but that target a particular antigen, TEM8, expressed on the tumor vascular endothelia. Importantly, the antibodies can bind to the predominant form of cell surface TEM8 that is concealed in its native state by other proteins that bind to it. These and other aspects of the invention are discussed in detail below.

I. Definitions

The term "antibody" as used herein refers to an immunoglobulin which possesses the ability to combine with an antigen. It comprises at least two heavy (H) chains and two light (L) chains inter-connected by disulfide bonds. Non-limiting examples of antibodies include monoclonal antibodies (e.g., full length or intact monoclonal antibodies), polyclonal antibodies, multivalent antibodies, and multi-specific antibodies (e.g., bi-specific antibodies as long as they exhibit the desired biological activity). An antibody can be human, humanized or affinity-matured, or combinations thereof.

The term "antibody fragment" comprises only a portion of an intact antibody, wherein the portion preferably retains at least one, preferably most or all, of the functions normally associated with that portion when present in an intact antibody. Examples of antibody fragments include Fab, Fab', F(ab')2, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody. In one embodiment, an antibody fragment is a monovalent antibody that has an in vivo half-life substantially similar to an intact antibody. For example, such an antibody fragment may comprise an antigen-binding arm linked to an Fc sequence capable of conferring in vivo stability to the fragment.

An "isolated" antibody is one which has been identified and separated or recovered, or both, from a component of its natural environment. Contaminant components of an isolated antibody's natural environment are materials which would interfere with diagnostic or therapeutic uses of the antibody. Non-limiting examples of such contaminants include enzymes, hormones, and other proteinaceous or non-proteinaceous solutes. In some embodiments, for example, the antibody may be purified to greater than 95% by weight of antibody as determined by the Lowry method, and sometimes more than 99% by weight. Isolated antibody includes the antibody in situ within recombinant cells because at least one component of the antibody's natural environment will not be present. Ordinarily, however, isolated antibody will be prepared by at least one purification step.

The terms "monoclonal antibody" or "monoclonal antibody composition" as used herein refer to a preparation of antibody molecules of single molecular composition. A monoclonal antibody composition displays a single binding specificity and affinity for a particular epitope. The monoclonal antibodies herein specifically include "chimeric" antibodies in which a portion of the heavy or light chain, or both, is identical with or homologous to corresponding sequences in antibodies derived from a particular species or belonging to a particular antibody class or subclass, while the remainder of the chain or chains are identical with or homologous to corresponding sequences in antibodies derived from another species or belonging to another antibody class or subclass, as well as fragments of such antibodies so long as they exhibit the desired biological activity.

The term "variable" refers to the fact that certain portions of the variable domain sequences differ extensively among antibodies and are important to the binding and specificity of each particular antibody for its particular antigen. However, such variability is not evenly distributed throughout the variable domains of antibodies and is concentrated in three segments called complementarity-determining regions (CDRs) or hypervariable regions which occur in both of the light-chain and the heavy-chain variable domains. The more highly conserved portions of variable domains are called the framework (FR). The variable domains of native heavy and light chains each comprise four FR regions (largely adopting a beta-sheet configuration) connected by three CDRs (which form loops connecting, and in some cases forming part of, the beta sheet structure). The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

The term "hypervariable region," "HVR," or "HV," when used herein, refers to the regions of an antibody variable domain which are hypervariable in sequence or form structurally defined loops, or both. Generally, antibodies comprise six hypervariable regions; three in the VH (H1, H2, H3), and three in the VL (L1, L2, L3).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody may comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally may also comprise at least a portion of an immunoglobulin constant region (Fc), typically that of a human immunoglobulin.

The term "recombinant human antibody," as used herein, includes all human antibodies that are prepared, expressed, created or isolated by recombinant means, such as (a) antibodies isolated from an animal (e.g., a mouse) that is transgenic or trans-chromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo. In other certain embodiments, pre-assembled trinucleotides are used in the chemical synthesis of the CDR sequences for such recombinant human antibodies.

"Chimeric" antibodies (immunoglobulins) have a portion of the heavy or light chain, or both, that is identical or homologous to corresponding sequences in antibodies derived from a particular species or belonging to a particular antibody class or subclass, while the remainder of the chain or chains are identical or homologous to corresponding sequences in antibodies derived from another species or belonging to another antibody class or subclass, as well as fragments of such antibodies, so long as they exhibit the desired biological activity. Humanized antibody as used herein is a subset of chimeric antibodies.

"Single-chain Fv" or "scFv" antibody fragments comprise the $V_H$ and $V_L$ domains of antibody, wherein these domains are present in a single polypeptide chain. Generally, the scFv polypeptide further comprises a polypeptide linker between the $V_H$ and $V_L$ domains which enables the scFv to form the desired structure for antigen binding.

An "antigen" is a predetermined antigen to which an antibody can selectively bind. The target antigen may be polypeptide, carbohydrate, nucleic acid, lipid, hapten or other naturally occurring or synthetic compound.

An "epitope" is the portion of the antigen to which the antibody selectively binds. For a polypeptide antigen, the epitope is generally a peptide portion of about four to ten amino acids.

The term "diabodies" refers to small antibody fragments with two antigen-binding sites, such fragments comprise a heavy-chain variable domain ($V_H$) connected to a light-chain variable domain ($V_L$) in the same polypeptide chain ($V_H$—$V_L$). By using a linker that is too short to allow pairing between the two domains on the same chain, the domains are forced to pair with the complementary domains of another chain and create two antigen-binding sites.

A "human antibody" is one which possesses an amino acid sequence which corresponds to that of an antibody produced by a human or has been made using any of the techniques for making human antibodies as disclosed herein, or both. This definition of a human antibody specifically excludes a humanized antibody comprising non-human antigen-binding residues.

An "affinity-matured" antibody is one with one or more alterations in one or more CDRs thereof which result in an improvement in the affinity of the antibody for antigen, compared to a parent antibody which does not possess those alteration(s). For example, affinity-matured antibodies may have nanomolar or even picomolar affinities for the target antigen. Affinity-matured antibodies are produced by procedures well-known in the art.

A "blocking" antibody or an "antagonist" antibody is one which inhibits or reduces biological activity of the antigen it binds. Preferred blocking antibodies or antagonist antibodies substantially or completely inhibit the biological activity of the antigen.

A "disorder" or "disease" is any condition that would benefit from treatment with a substance/molecule or method of the invention. This includes chronic and acute disorders or diseases including those pathological conditions which predispose subjects to the disorder in question. Non-limiting examples of disorders to be treated herein include malignant and benign tumors.

The terms "cell proliferative disorder" and "proliferative disorder" refer to disorders that are associated with some degree of abnormal cell proliferation. In one embodiment, the disorder is a disorder associated with abnormal proliferation of vascular endothelial cells.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

The terms "cancer" and "cancerous" refer to or describe the physiological condition in mammals that is typically characterized by unregulated cell growth/proliferation. Examples of cancer include, but are not limited to, carcinoma, lymphoma, blastoma, sarcoma, and leukemia. More particular examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer. Dysregulation of angiogenesis can lead to many disorders that can be treated by compositions and methods of the invention. These disorders include both non-neoplastic and neoplastic conditions. Neoplastic conditions include but are not limited those described above.

"Non-neoplastic disorders" include but are not limited to undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

A cell which "expresses native cell surface TEM8" is a cell which expresses TEM8 at the cell surface. Aspects of the present invention pertain to methods of treating a cancer or tumor that includes cells that express native cell surface TEM8.

"Treatment" as used herein refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, reduction of any direct or indirect pathological consequences of the disease, decreasing the rate of disease progression, amelioration or palliation of the disease state, and remission or improved prognosis. In some embodiments, antibodies of the invention are used to delay development of a disease or disorder. In non-limiting examples, antibodies of the invention may be used to reduce the rate of tumor growth or reduce the risk of metastasis of a cancer.

An "individual," "subject," or "patient" is a vertebrate, e.g. a mammal, including especially a human. Mammals include, but are not limited to, humans, domestic and farm animals, and zoo, sports, or pet animals, such as dogs, horses, cats, cows, rats, mice, etc.

An "effective amount" refers to an amount effective, at dosages and for periods of time necessary, to achieve the desired therapeutic or prophylactic result.

A "therapeutically effective amount" of a substance/molecule of the invention refers to an amount of a drug effective to treat a disease or disorder in a mammal. It may vary according to factors such as the disease state, age, sex, and weight of the individual, and the ability of the substance/molecule to elicit a desired response in the individual. A therapeutically effective amount is also one in which any toxic or detrimental effects of the substance/molecule are outweighed by the therapeutically beneficial effects.

A "prophylactically effective amount" refers to an amount effective, at dosages and for periods of time necessary, to achieve the desired prophylactic result. As a prophylactic dose is used in subjects prior to or at an earlier stage of disease. The prophylactically effective amount typically, but not necessarily, will be less than the therapeutically effective amount.

The term "cytotoxic agent" as used herein refers to a substance that inhibits or prevents the function of cells or causes destruction of cells, or both. The term is intended to include radioactive isotopes, chemotherapeutic agents, and toxins such as small molecule toxins or enzymatically active toxins of bacterial, fungal, plant or animal origin, including synthetic analogs and derivatives thereof.

A "chemotherapeutic agent" is a chemical compound useful in the treatment of cancer. Non-limiting examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; bisphosphonates, such as clodronate; antibiotics such as the enediyne antibiotics (e.g., calicheamicin, especially calicheamicin gamma 1I and calicheamicin omega 1 (see, e.g., Anger, Chem Intl. Ed. Engl., 33: 183-186 (1994)) and anthracyclines such as annamycin, AD 32, alcarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, detorubicin, 6-diazo-5-oxo-L-norleucine, doxorubicin (ADRIAMYCIN®, including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; folic acid analogues such as denopterin, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate, anti-metabolites such as 5-fluorouracil (5-FU) and its prodrugs such as UFT, S-1 and capecitabine, and thymidylate synthase inhibitors and glycinamide ribonucleotide formyltransferase inhibitors such as raltitrexed (TOMUDEX™, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitracrine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacyto sine; arabinoside ("Ara-C"); cyclophosphamide; thiotepa; taxoids and taxanes, e.g., TAXOL® paclitaxel (Bristol-Myers Squibb Oncology, Princeton, N.J.), ABRAXANE™ Cremophorfree, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; platinum; platinum analogs or platinum-based analogs such as cisplatin, oxaliplatin and carboplatin; vinblastine (VELB AN®); etoposide (VP-16); ifosfamide; mitoxantrone; vincristine (ONCOVIN®); vinca alkaloid; vinorelbine (NAVELB INE®); novantrone; edatrexate; daunomycin; aminopterin; xeloda; ibandronate; topoisomerase inhibitor RFS 2000; difluorometlhylomithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU, leucovorin, and ADCETRIS™ (Brentuximab Vedotin).

Also included in the definition of chemotherapeutic agents are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in adherent cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above. Also included in this definition are small molecule toxins, such as a calicheamicin, maytansinoids, dolastatins, aurostatins, a trichothecene, and CC1065.

The term "EGFR-targeted drug" as used herein refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBITUX®) and reshaped human 225 (H225) (see, WO 96/40210, Imclone Systems Inc.); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO 98/50433, Abgenix). The anti-EGFR antibody may be conjugated with a cyotoxic agent, thus generating an immunoconjugate (see, e.g., EP 659,439A2, Merck Patent GmbH). Examples of small molecules that bind to EGFR include ZD1839 or Gefitinib (IRESSA™; Astra Zeneca), Erlotinib HCl (CP-358774, TARCEVA™; Genentech/OSI) and AG1478, AG1571 (SU 5271; Sugen).

A "tyrosine kinase inhibitor" as used herein is a molecule which inhibits to some extent tyrosine kinase activity of a tyrosine kinase such as an ErbB receptor. Examples of such inhibitors include the EGFR-targeted drugs noted in the preceding paragraph as well as quinazolines such as PD 153035,4-(3-chloroanilino) quinazoline, pyridopyrimidines, pyrimidopyrimidines, pyrrolopyrimidines, such as CGP 59326, CGP 60261 and CGP 62706, and pyrazolopyrimidines, 4-(phenylamino)-7H-pyrrolo[2,3-d]pyrimidines, curcumin (diferuloyl methane, 4,5-bis(4-fluoroanilino)phthalimide), tyrphostines containing nitrothiophene moieties; PD-0183805 (Warner-Lambert); antisense molecules (e.g., those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-ErbB inhibitors such as CI-1033 (Pfizer); Affinitac (ISIS 3521; Isis/Lilly); Imatinib mesylate (Gleevac; Novartis); PKI 166 (Novartis); GW2016 (Glaxo SmithKline); CI-1033 (Pfizer); EKB-569 (Wyeth); Semaxanib (Sugen); ZD6474 (AstraZeneca); PTK-787 (Novartis/Schering AG); INC-1C11 (Imclone); or as described in any of the following patent publications: U.S. Pat. No. 5,804,396; WO 99/09016 (American Cyanamid); WO 98/43960 (American Cyanamid); WO 97/38983 (Warner Lambert); WO 99/06378 (Warner Lambert); WO 99/06396 (Warner Lambert); WO 96/30347 (Pfizer, Inc); WO 96/33978 (Zeneca); WO 96/3397 (Zeneca); and WO 96/33980 (Zeneca).

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. The anti-angiogenic agent may also be a fragment of a growth factor receptor. For example, the anti-antiogenic agent may be all or part of an extracellular domain of a growth factor receptor. Non-limiting examples of growth factor receptors are set forth elsewhere in this specification.

A "liposome" is a small vesicle composed of various types of lipids, phospholipids or surfactant, or combinations thereof, which is useful for delivery of a drug to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications or warnings concerning the use of such therapeutic products, or combinations thereof.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

"Polynucleotide" or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A nucleic acid is "operably linked" when it is placed into a functional relationship with another nucleic acid sequence.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome (such as an adenoviral vector, a lentiviral vector, etc.). Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors").

The term "peptide" as used herein refers to a consecutive series of two to 500 amino acid.

The term "polypeptide" as used herein refers to a consecutive series of two or more amino acids.

The term "sequence identity" (or "sequence similarity") is herein defined as a relationship between two or more nucleic acid (polynucleotide) or amino acid (polypeptide) sequences, as determined by comparing the sequences. Usually, sequence identities or similarities are compared, typically over the whole length of the sequences compared. However, sequences may be compared over shorter comparison windows. In the art, "identity" also means the degree of relatedness between nucleic acid or amino acid sequences, as the case may be, as determined by the match between strings of such sequences.

"Alkylyl" is $C_1$-$C_{18}$ hydrocarbon containing normal, secondary, tertiary or cyclic carbon atoms. Examples are methyl (Me, —CH$_3$), ethyl (Et, —CH$_2$CH$_3$), 1-propyl(n-Pr, n-propyl, —CH$_2$CH$_2$CH$_3$), 2-propyl(i-Pr, i-propyl, —CH(CH$_3$)$_2$), 1-butyl (n-Bu, n-butyl, —CH$_2$CH$_2$CH$_2$CH$_3$), 2-methyl-1-propyl(i-Bu, i-butyl, —CH$_2$CH(CH$_3$)$_2$), 2-butyl (s-Bu, s-butyl, —CH(CH$_3$)CH$_2$CH$_3$), 2-methyl-2-propyl(t-Bu, t-butyl, —C(CH$_3$)$_3$), 1-pentyl(n-pentyl, —CH$_2$CH$_2$CH$_2$CH$_2$CH$_3$), 2-pentyl(—CH(CH$_3$) CH$_2$CH$_2$CH$_3$), 3-pentyl(—CH(CH$_2$CH$_3$)$_2$), 2-methyl-2-butyl(—C(CH$_3$)$_2$CH$_2$CH$_3$), 3-methyl-2-butyl(—CH(CH$_3$)CH (CH$_3$)$_2$), 3-methyl-1-butyl(—CH$_2$CH$_2$CH(CH$_3$)$_2$), 2-methyl-1-butyl(CH$_2$CH(CH$_3$)CH$_2$CH$_3$), 1-hexyl(—CH$_2$CH$_2$CH$_2$CH$_2$CH$_2$CH$_3$), 2-hexyl(—CH(CH$_3$) CH$_2$CH$_2$CH$_2$CH$_3$), 3-hexyl(—CH(CH$_2$CH$_3$) (CH$_2$CH$_2$CH$_3$)), 2-methyl-2-pentyl(—C(CH$_3$)$_2$ CH$_2$CH$_2$CH$_3$), 3-methyl-2(—CH(CH$_3$)CH(CH$_3$)CH$_2$CH$_3$), 4-methyl-2-pentyl(—CH(CH$_3$)CH$_2$CH(CH$_3$)$_2$), 3-methyl-3pentyl(—C(CH$_3$)(CH$_2$CH$_3$)$_2$), 2-methyl-3-pentyl(—CH (CH$_2$CH$_3$)CH(CH$_3$)$_2$), 2,3-dimethyl-2-butyl(—C(CH$_3$)$_2$CH (CH$_3$)$_2$), 3,3-dimethyl-2-butyl(—CH(CH$_3$)C(CH$_3$)$_3$.

"Alkenyl" is $C_2$-$C_{18}$ hydrocarbon containing normal, secondary, tertiary or cyclic carbon atoms with at least one site of unsaturation, i.e. a carbon-carbon, sp$^2$ double bond. Examples include, but are not limited to: ethylene or vinyl (—CH=CH2), allyl (—CH$_2$CH=CH$_2$), cyclopentenyl(—C$_5$H$_7$), and 5-hexenyl (—CH$_2$CH$_2$CH$_2$CH$_2$CH=CH$_2$).

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—CH$_2$C≡CH).

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH$_2$—) 1,2ethyl-(—CH$_2$CH$_2$—), 1,3-propyl(—CH$_2$CH$_2$CH$_2$—), 1,4-butyl(—CH$_2$CH$_2$CH$_2$CH$_2$—). and the like.

"Alkenylene" refers to an unsaturated, branched or straight chain or cyclic hydrocarbonradical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (CH=CH—).

"Alkynylene" refers to an unsaturated, branched or straight chain or cyclic hydrocarbonradical of two to eighteen carbon atoms, and having two monovalent radical centers derived by the removal of two hydrogen atoms from the same or two different carbon atoms of a parent alkyne. Typical alkynylene radicals include, but are not limited to: acetylene(—C≡C—), propargyl(—CH$_2$C≡C—), and 4-pentynyl(CH$_2$CH$_2$CH$_2$C≡CH—).

"Aryl" means a monovalent aromatic hydrocarbon radical of six to twenty carbon atoms derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises six to twenty carbon atoms, e.g., the alkyl moiety, including alkanyl, alkenyl or alkynyl groups, of the arylalkyl group is one to six carbon atoms and the aryl moiety is five to fourteen carbon atoms.

"Heteroarylalkyl" refers to an acyclic alkyl radical in which one of the hydrogen atoms bonded to a carbon atom, typically a terminal or sp³ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g., the alkyl moiety, including alkanyl, alkenylor alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl", "substituted aryl", and "substituted arylalkyl" mean alkyl, aryl, and arylalkyl respectively, in which one or more hydrogen atoms are each independently replaced with a substituent. Typical substituents include, but are not limited to, —X, —R, —O⁻, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(=O)(OR)$_2$. —PO⁻$_3$, —PO$_3$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, —C(=NR)NR$_2$, where each X is independently a halogen: F, Cl, Br, or I; and each R is independently —H, C$_2$-C$_{18}$ alkyl, C$_6$-C$_{20}$ aryl, C$_3$-C$_{14}$ heterocycle, protecting group or prodrug moiety. Alkylene, alkenylene, and alkynylene groups as described above may also be similarly substituted.

"Heteroaryl" and "Heterocycle" refer to a ring system in which one or more ring atoms is a heteroatom, e.g., nitrogen, oxygen, and sulfur. The heterocycle radical comprises 1 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected
from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system.

Heterocycles are described in Paquette, LeoA.; "Principles of Modem Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-earbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2,3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" means a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

"Linker", "Linker Unit", or "link" means a chemical moiety comprising a covalent bond or a chain of atoms that covalently attaches an antibody to a drug moiety. In various embodiments, a linker is specified as LU. Linkers include a divalent radical such as an alkyldiyl, an aryldiyl, a heteroaryldiyl, moieties such as: —(CR$_2$)$_n$O(CR$_2$)$_n$—, repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and capromide.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

The term "$C_1$-$C_8$ alkyl," as used herein refers to a straight chain or branched, saturated or unsaturated hydrocarbon having from 1 to 8 carbon atoms. Representative "$C_1$-$C_8$ alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched $C_1$-$C_8$ alkyls include, but are not limited to, -isopropyl, -sec-butyl, -isobutyl, -tert-butyl, -isopentyl, 2-methylbutyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1-butynyl. methyl, ethyl, propyl, isopropyl, n-butyl, isobutyl, sec-butyl, tert-butyl, n-pentyl, isopentyl, neopentyl, n-hexyl, isohexyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methyl-hexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —$SO_3$R', —S(O)$_2$R', —S(O)R', —OH, -halogen, —$N_3$, —$NH_2$, —NH(R'), —N(R')$_2$ and —CN; where each R' is independently selected from H, —$C_1$-$C_8$ alkyl and aryl.

A "$C_3$-$C_8$ carbocycle" is a 3-,4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH2, —C(O)NHR', —C(O)N(R')$_2$NHC(O)R', —S(O)$_2$R', —S(O)R', —OH, -halogen, —$N_3$, —$NH_2$, —NH(R'), —N(R')$_2$ and —CN; where each R' is independently selected from H, —$C_1$-$C_8$ alkyl and aryl.

A "C3-C8 carbocyclo" refers to a C3-C8 carbocycle group defined above wherein one of the carbocycle groups' hydrogen atoms is replaced with a bond.

A "$C_1$-$C_{10}$ alkylene" is a straight chain, saturated hydrocarbon group of the formula —$(CH_2)_{1-10}$—. Examples of a $C_1$-$C_{10}$ alkylene include methylene, ethylene, propylene, butylene, pentylene, hexylene, heptylene, ocytylene, nonylene and decalene.

An "arylene" is an aryl group which has two covalent bonds and can be in the ortho, meta, or para configurations as shown in the following structures:

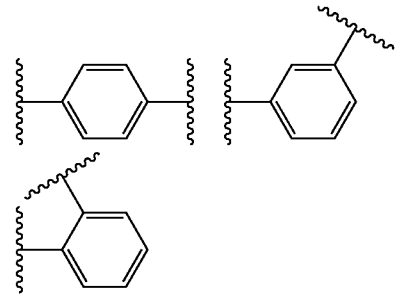

in which the phenyl group can be unsubstituted or substituted with up to four groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$NHC(O)R', —S(O)$_2$R', —S(O)R', —OH, -halogen, —$N_3$, —$NH_2$, —NH(R'), —N(R')$_2$ and —CN; wherein each R' is independently selected from H, —C1-$C_8$ alkyl and aryl.

A "$C_3$-$C_8$ heterocycle" refers to an aromatic or non-aromatic $C_3$-$C_8$ carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

"$C_3$-$C_8$ heterocyclo" refers to a $C_3$-$C_8$ heterocycle group defined above wherein one of the heterocycle group's hydrogen atoms is replaced with a bond. A $C_3$-$C_8$ heterocyclo can be unsubstituted or substituted with up to six groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

The phrase "pharmaceutically acceptable salt," as used herein, refers to pharmaceutically acceptable organic or inorganic salts of an Exemplary Compound or Exemplary Conjugate. The Exemplary Compounds and Exemplary Conjugates contain at least one amino group, and accordingly acid addition salts can be formed with this amino group. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterionmay be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counte-non.

"Pharmaceutically acceptable solvate" or"solvate" refer to an association of one or more solvent molecules and a compound of the invention, e.g., an Exemplary Compound or Exemplary Conjugate. Examples of solvents that form pharmaceutically acceptable solvates include, but are not limited to, water, isopropanol, ethanol, methanol, DMSO, ethyl acetate, acetic acid, and ethanolamine.

"Phage display" is a laboratory technique used for the high-throughput screening of protein interactions. For example, in the case of M13 filamentous phage display, DNA encoding the protein or peptide of interest is ligated into the pIII or pVIII gene, encoding either the minor or major coat protein, respectively. Multiple cloning sites are sometimes used to ensure that the fragments are inserted in all three possible frames so that the cDNA fragment is translated in the proper frame. The phage gene and insert DNA hybrid is then transformed into *Escherichia coli* (*E. coli*) bacterial cells such as TG1, SS320, ER2738, or XL1-Blue *E. coli*. If a "phagemid" vector is used (a simplified display construct vector) phage particles will not be released from the *E. coli* cells until they are infected with helper phage, which enables packaging of the phage DNA and assembly of the mature virions with the relevant protein fragment as part of their outer coat on either the minor (pIII) or major (pVIII) coat protein. By immobilizing a relevant DNA or protein target to the surface of a well, a phage that displays a protein that binds to one of those targets on its surface will remain while others are removed by washing. Phage that remain can be eluted, used to produce more phage (by bacterial infection with helper phage), and thus produce a phage mixture that is enriched with relevant (i.e. binding) phage. The repeated cycling of these steps is referred to as 'panning', in reference to the enrichment of a sample of gold by removing undesirable materials. Phage eluted in the final step can be used to infect a suitable bacterial host, from which the phagemids can be collected and the relevant DNA sequence excised and sequenced to identify the relevant, interacting proteins or protein fragments.

A "phage display library" is a collection of recombinant phage, each displaying a different antigen-binding domain on its surface. In much the same way that antibodies specific for a particular antigen can be isolated from a complex mixture by affinity chromatography, phage-expressing antigen-binding domains specific for a particular antigen can be isolated by selecting the phage in the library for binding to that antigen. The phage particles that bind are recovered and used to infect fresh bacteria. Each phage isolated in this way will produce a monoclonal antigen-binding particle analogous to a monoclonal antibody. The genes encoding the antigen binding site, which are unique to each phage, can then be recovered from the phage DNA and used to construct genes for a complete antibody molecule by joining then to parts of immunoglobulin genes that encode the invariant parts of the an antibody. When these reconstructed antibody genes are introduced into a suitable host cell line, the transfected cells can secrete antibodies with all the desirable characteristics of monoclonal antibodies of the suitable host cell line.

II. Antibodies and Antibody Fragments and Methods of Making Same

A. General Methods for the Production of Antibodies and Nucleic Acids Encoding Antibodies The invention includes isolated antibodies or antibody fragments that bind immunologically to native cell surface-expressed TEM8 and isolated polynucleotides comprising sequences encoding one or more antibodies or antibody fragments that bind to TEM8. The invention also includes pharmaceutical compositions that include antibodies or antibody fragments that binds immunologically to native cell surface-expressed TEM8 and polynucleotides comprising sequences encoding one or more antibodies or antibody fragments that bind to TEM8.

In particular embodiments the anti-TEM8 antibodies of the invention are monoclonal antibodies. Monoclonal antibodies of the present invention can be produced by a variety of techniques, such as by conventional monoclonal antibody methodology using standard somatic cell hybridization techniques and viral or oncogenic transformation of B lymphocytes.

Monoclonal antibodies may be obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-TEM8 monoclonal antibodies of the invention can be made using a hybridoma method, or may be made by recombinant DNA methods well-known to those of ordinary skill in the art.

Regarding the hybridoma method, the first step is immunization of an appropriate host, as may be achieved by coupling a peptide or polypeptide immunogen to a carrier. Exemplary carriers are keyhole limpet hemocyanin (KLH), bovine serum albumin (BSA, ovalbumin, mouse serum albumin and rabbit serum albumin. As also is well known in the art, the immunogenicity of a particular immunogen composition can be enhanced by the use of non-specific stimulators of the immune response, known as adjuvants.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. One or more additional booster injections may be given. The process of boosting and titering is repeated until a suitable titer is achieved. When a desired level of immunogenicity is obtained, the immunized animal can be bled and the serum isolated and stored, and/or the animal can be used to generate monoclonal antibodies.

Following immunization, somatic cells with the potential for producing antibodies, specifically B lymphocytes (B cells), are selected for use in the monoclonal antibody-generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized. Any one of a number of myeloma cells may be used, as are known to those of skill in the art. For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One particular murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line. Additional fusion partner lines for use with human B cells include KR12 (ATCC CRL-8658; K6H6/B5 (ATCC CRL-1823 SHM-D33 (ATCC CRL-1668) and HMMA2.5 (Posner et al., 1987). In a particular embodiment, the line used to generate the antibody in this invention is OUR-1.

Methods for generating hybrids of antibody-producing spleen or lymph node cells and myeloma cells usually comprise mixing somatic cells with myeloma cells in the presence of an agent or agents (chemical or electrical) that promote the fusion of cell membranes.

The viable, fused hybrids may be differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

Hypoxanthine aminopterm thymidine (HAT) may be used as a selection medium. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoas says, enzyme immunoassays, cytotoxicity assays, plaque assays, dot immunobinding assays, and the like.

The selected hybridomas are then serially diluted and cloned into individual antibody-producing cell lines, which clones can then be propagated indefinitely to provide monoclonal antibodies. The cell lines may be exploited for monoclonal antibody production using any method known to those of ordinary skill in the art. In one example, a sample of the hybridoma can be injected (often into the peritoneal cavity) into an animal (e.g., a mouse). Optionally, the animals are primed with a hydrocarbon, especially oils such as pristane (tetramethylpentadecane) prior to injection.

When human hybridomas are used in this way, it is optimal to inject immunocompromised mice, such as severe combined immunodeficient (SCID) mice, to prevent tumor rejection. The injected animal develops tumors secreting the specific monoclonal antibody produced by the fused cell hybrid. The body fluids of the animal, such as serum or ascites fluid, can then be tapped to provide monoclonal antibodies in high concentration. The individual cell lines could also be cultured in vitro, where the monoclonal antibodies are naturally secreted into the culture medium from which they can be readily obtained in high concentrations.

In the hybridoma method, a mouse or other appropriate host animal is immunized to elicit lymphocytes that produce or are capable of producing antibodies that will specifically bind to the protein used for immunization. Antibodies to TEM8 may generally be raised in animals by multiple subcutaneous (sc) or intraperitoneal (ip) injections of TEM8 and an adjuvant. TEM8 may be prepared using methods well-known in the art.

In some embodiments, lymphocytes may be immunized in vitro. Lymphocytes then are fused with myeloma cells using a suitable fusing agent, such as polyethylene glycol, to form a hybridoma cell.

The hybridoma cells thus prepared may be seeded and grown in a suitable culture medium that preferably contains one or more substances that inhibit the growth or survival of the unfused, parental myeloma cells. Culture medium in which hybridoma cells are growing is assayed for production of monoclonal antibodies directed against TEM8. The binding specificity of monoclonal antibodies produced by hybridoma cells may be determined be techniques well-known to those in the art, such as by immunoprecipitation or by an in vitro binding assay (e.g., radioimmunoassay (RIA) or enzyme-linked immunoabsorbent assay (ELISA)). The binding affinity of the monoclonal antibody can, for example, be determined by a Scatchard analysis. After hybridoma cells are identified that produce antibodies of the desired specificity, affinity, and/or activity, the clones may be subcloned by limiting dilution procedures and grown by standard methods. The monoclonal antibodies secreted by the subclones may be suitably separated from the culture medium by conventional immunoglobulin purification procedures such as, for example, protein A-Sepharose, hydroxylapatite chromatography, gel electrophoresis, dialysis, or affinity chromatography.

The anti-TEM8 antibodies of the invention can be made by using combinatorial libraries, such as a phage display library, to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. In a certain embodiment, the anti-TEM8 antibodies are produced in bacteria and the library is screened using phage display to identify the antibody with a high affinity to TEM8.

In a particular embodiment to prepare antibodies against TEM8 in its native cell-surface conformation, recombinant cells were produced that express full-length human TEM8 by employing CMV-promoter driven expression vector. First CHO cells lacking expression of TEM8 or CMG2 were made (designated CHO-PR230 cells). These cells (CHO-PR230 cells) were enriched for highly stable TEM8 expression by flow cytometry sorting using phycoerythrin-conjugated protective antigen. For immunization, 2.5 million CHO/TEM8 cells were injected intraperitoneally once per month for four months into young Balb/c female mice and spleens harvested three days after the final boost. Hybridomas were prepared by fusing OUR-1 mouse myeloma cells with splenocytes. Flow cytometry screening of CHO and CHO/TEM8 cells was performed to identify TEM8-specific antibodies from supernatants of individual hybridoma clones. As a secondary screen, hybridoma supernatants were used in an enzyme-linked immunoassay performed on membrane preparations made by sonication of CHO or CHO/TEM8 cells as previously described (Frankel et al., 1985). The AF344 hybridoma produced an IgMλ which reacted specifically with CHO/TEM8 but not CHO or CHO/CMG2 cells. The AF344 hybridoma maintained stable expression after subcloning three times, and antibodies were purified from hybridoma supernatants by gel filtration.

Monoclonal antibodies produced by any means may be further purified, if desired, using any technique known to those of ordinary skill in the art, such as filtration, centrifugation and various chromatographic methods such as FPLC or affinity chromatography or any other method known to those of ordinary skill in the art.

Nucleic acids encoding antibody gene fragments may be obtained from immune cells harvested from humans or animals. If a library biased in favor of anti-TEM8 clones is desired, the subject is immunized with TEM8 to generate an antibody response, and spleen cells and/or circulating B cells or other peripheral blood lymphocytes (PBLs) are recovered for library construction. Additional enrichment for anti-TEM8 reactive cell populations can be obtained by using a suitable screening procedure to isolate B cells expressing TEM8-specific membrane bound antibody. Alternatively, the use of spleen cells and/or B cells or other PBLs from an unimmunized donor provides a better representation of the possible antibody repertoire, and also permits the construction of an antibody library using any animal (human or non-human) species in which TEM8 is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, etc. Nucleic acid encoding antibody variable gene segments are recovered from the cells of interest and amplified.

Nucleic acid sequence encoding a TEM8 polypeptide can be designed using the amino acid sequence of the desired region of TEM8. Alternatively, the cDNA sequence (or fragments thereof) may be used. DNAs encoding TEM8 can be prepared by a variety of methods known in the art. Following construction of the DNA molecule encoding TEM8, the DNA molecule is operably linked to an expression control sequence in an expression vector, such as a plasmid, wherein the control sequence is recognized by a host cell transformed with the vector. Suitable vectors for expression in prokaryotic and eukaryotic host cells are known in the art. Optionally, the DNA encoding TEM8 is operably linked to a secretory leader sequence resulting in secretion of the expression product by the host cell into the culture medium. Host cells are transfected and preferably transformed with the expression or cloning vectors of this invention and cultured in conventional nutrient media modified as appropriate for inducing promoters, selecting transformants, or amplifying the genes encoding the desired sequences.

The purified TEM8 can be attached to a suitable matrix such as agarose beads, acrylamide beads, glass beads, cellulose, various acrylic copolymers, hydroxyl methacrylate gels, polyacrylic and polymethacrylic copolymers, nylon, neutral and ionic carriers, and the like, for use in the affinity chromatographic separation of phage display clones. Alternatively, TEM8 can be used to coat the wells of adsorption plates, expressed on host cells affixed to adsorption plates or used in cell sorting, or conjugated to biotin for capture with streptavidin-coated beads, or used in any other art-known method for panning phage display libraries. The phage library samples are contacted with immobilized TEM8 under conditions suitable for binding of at least a portion of the phage particles with the adsorbent. Normally, the conditions, including pH, ionic strength, temperature and the like are selected to mimic physiological conditions. The phages bound to the solid phase are washed and then eluted. Moreover, the enriched phages can be grown in bacterial culture and subjected to further rounds of selection.

DNA encoding the hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as $E.\ coli$ cells, simian COS cells, Chinese hamster ovary (CHO) cells, or myeloma cells that do not otherwise produce immunoglobulin protein, to obtain the synthesis of the desired monoclonal antibodies in the recombinant host cells.

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In a preferred embodiment, a Fv clone derived from human variable DNA is fused to human constant region DNA to form coding sequence(s) for all human, full or partial length heavy and/or light chains.

DNA encoding anti-TEM8 antibody derived from a hybridoma of the invention can also be modified, for example, by substituting the coding sequence for human heavy- and light-chain constant domains in place of homologous murine sequences derived from the hybridoma clone. DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

B. Antibody Fragments

The present invention encompasses antibody fragments. In certain circumstances there are advantages of using antibody fragments, rather than whole antibodies. The smaller size of the fragments may allow for rapid clearance, and may lead to improved access to solid tumors.

Non-limiting examples of antibody fragments include Fab, Fab', Fab'-SH and F(ab')2 fragments of the anti-TEM8 antibodies provided herein. These antibody fragments can be created by traditional means, such as enzymatic digestion, or may be generated by recombinant techniques. Some antibody fragments may be chimeric or humanized. These fragments are useful for the diagnostic and therapeutic purposes set forth below.

Various techniques may be used for the production of antibody fragments. Traditionally, these fragments were derived via proteolytic digestion of intact antibodies, such as with pepsin or papain and/or by cleavage of disulfide bonds by chemical reduction. However, these fragments can now be produced directly by recombinant host cells. For example, Fab, Fv and ScFv antibody fragments can all be expressed in and secreted from E. coli, thus allowing the facile production of large amounts of these fragments. Alternatively, monoclonal antibody fragments encompassed by the present invention can be synthesized using an automated peptide synthesizer.

Antibody fragments can be isolated from the antibody phage libraries discussed above. Alternatively, Fab'-SH fragments can be directly recovered from E. coli and chemically coupled to form F(ab')2 fragments. According to another approach, F(ab')2 fragments can be isolated directly from recombinant host cell culture. Other techniques for the production of antibody fragments will be apparent to the skilled practitioner. In other embodiments, the antibody of choice is a single chain Fv fragment (scFv). Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. The antibody fragment may also be a "linear antibody.". Such linear antibody fragments may be monospecific or bispecific.

C. Humanized Antibodies

The present invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed using any method known to those of ordinary skill in the art. Accordingly, such "humanized" antibodies are chimeric antibodies wherein substantially less than an intact human variable domain has been substituted by the corresponding sequence from a non-human species. In practice, humanized antibodies are typically human antibodies in which some hypervariable region residues.

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

D. Human Antibodies

Human anti-TEM8 antibodies (or fragments thereof) of the invention can be constructed by combining Fv clone variable domain sequence(s) selected from human-derived phage display libraries with known human constant domain sequences(s) as described above. Alternatively, human monoclonal anti-TEM8 antibodies of the invention can be made by the hybridoma method. Other methods known to those of ordinary skill in the art can be utilized.

Transgenic animals (e.g. mice) can be produced that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Gene shuffling can also be used to derive human antibodies from non-human, e.g. rodent, antibodies, where the human antibody has similar affinities and specificities to the starting non-human antibody. According to one method, which is also called "epitope imprinting," either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained. Unlike traditional humanization of non-human antibodies by CDR grafting, this technique provides completely human antibodies, which have no FR or CDR residues of non-human origin.

E. Bispecific Antibodies

Bispecific antibodies are monoclonal, preferably human or humanized, antibodies that have binding specificities for at least two different antigens. In the present case, one of the binding specificities is for TEM8 and the other is for any other antigen. Exemplary bispecific antibodies may bind to two different epitopes of the TEM8 protein. Bispecific antibodies may also be used to localize cytotoxic agents to cells which express TEM8. These antibodies possess a TEM8-binding arm and an arm which binds the cytotoxic agent (e.g. saporin, anti-interferon-.alpha., vinca alkaloid, ricin A chain, methotrexate or radioactive isotope hapten). Bispecific antibodies can be prepared as full length antibodies or antibody fragments (e.g. F(ab')2 bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities.

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In some embodiments, the bispecific antibodies are composed of a hybrid immunoglobulin heavy chain with a first binding specificity in one arm, and a hybrid immunoglobulin heavy chain-light chain pair (providing a second binding specificity) in the other arm. According to another approach, the interface between a pair of antibody molecules can be engineered to maximize the percentage of heterodimers which are recovered from recombinant cell culture.

Techniques for generating bispecific antibodies from antibody fragments have also been described in the literature. For example, bispecific antibodies can be prepared using chemical linkage.

Various techniques for making and isolating bispecific antibody fragments directly from recombinant cell culture have also been described. For example, bispecific antibodies have been produced using leucine zippers. The "diabody" technology provides an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments involves the use of single-chain Fv (sFv) dimmers.

F. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody may comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. In some embodiments, the multivalent antibody comprises (or consists of) three to about eight, but preferably four, antigen binding sites. The multivalent antibody comprises at least one polypeptide chain (and preferably two polypeptide chains), wherein the polypeptide chain(s) comprise two or more variable domains.

G. Antibody Variants

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

Amino acid sequence insertions include amino- and/or carboxyl-terminal fusions ranging in length from one residue to polypeptides containing a hundred or more residues, as well as intrasequence insertions of single or multiple amino acid residues. Non-limiting examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody or to a therapeutic amino acid sequence such as a thrombogenic polypeptide.

Another type of amino acid variant of the antibody alters the original glycosylation pattern of the antibody. Such altering includes deleting one or more carbohydrate moieties found in the antibody, and/or adding one or more glycosylation sites that are not present in the antibody. Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

One type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity). In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. In accordance with this description and the teachings of the art, it is contemplated that in some embodiments, an antibody used in methods of the invention may comprise one or more alterations as compared to the wild type counterpart antibody, e.g. in the Fc region. These antibodies would nonetheless retain substantially the same characteristics required for therapeutic utility as compared to their wild type counterpart.

H. Antibody Derivatives

The antibodies of the present invention can be further modified to contain additional non-proteinaceous moieties that are known in the art and readily available. For example, in some embodiments, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In these contexts, one may to link such antibodies to diagnostic or therapeutic agents, or use them as capture agents or competitors in competitive assays.

III. Screening for Antibodies with Desired Properties

The antibodies of the invention bind native cell surface-expressed TEM8, and in some embodiments, may modulate one or more aspects of any TEM8-associated effects, including but not limited to disruption of any biologically relevant TEM8 function. Non-limiting examples include modulation of TEM8 binding to collagen or extracellular matrix proteins, or modification of TEM8 to promote pathological angiogenesis.

Any technique known to those of ordinary skill in the art can be used to characterize the purified antibodies. Non-limiting examples of such techniques include N-terminal sequencing, amino acid analysis, non-denaturing size exclusion, high pressure liquid chromatography (HPLC), mass spectrometry, ion exchange chromatography and papain digestion.

In some embodiments, the antibodies of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays.

Anti-TEM8 antibodies of the invention possessing the properties described herein can be obtained by screening anti-TEM8 hybridoma clones for the desired properties by any convenient method. For example, if an anti-TEM8 monoclonal antibody that competes or does not compete for TEM8 binding with an antibody comprising a light chain variable domain comprising a sequence selected from SEQ ID NO: 1 and a heavy chain variable domain comprising a sequence selected from SEQ ID NO: 2 is desired, the candidate antibody can be tested in a binding competition assay. Competition assays are well known in the art.

Other functional assays to determine the inhibitory capacity of anti-TEM8 antibodies are known in the art. In some embodiments, the present invention contemplates altered antibodies that possess some but not all effector functions, which make it a desired candidate for many applications in which the half life of the antibody in vivo is important yet certain effector functions are unnecessary or deleterious. In some embodiments, the invention provides altered antibodies that possess increased effector functions and/or increased half-life.

In some embodiments there are methods for producing or manufacturing an anti-TEM8 antibody. Reagents and methods for producing antibodies are well known, including large-scale production of antibodies (Shukla et al., Trends in Biotechnol. 2010 May; 28(5):253-61, which is hereby incorporated by reference).

IV. Vectors, Host Cells and Recombinant Methods

For recombinant production of an antibody of the invention, the nucleic acid encoding it can be isolated and inserted into a replicable vector for further cloning (amplification of the DNA) or for expression. DNA encoding the antibody is isolated and sequenced using conventional procedures (e.g., by using oligonucleotide probes that are capable of binding specifically to genes encoding the heavy and light chains of the antibody). Many vectors are available. The choice of vector depends in part on the host cell to be used. Host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

A. Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

Plasmid vectors containing replicon and control sequences which are derived from species compatible with the host cell may be used. The vector may carry a replication site, as well as marking sequences which are capable of providing phenotypic selection in transformed cells. In addition, phage vectors containing replicon and control sequences that are compatible with the host microorganism may be used as transforming vectors in connection with these hosts.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Some examples of prokaryotic host cells suitable for expressing antibodies include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In some embodiments, Gram-negative cells are used. In some embodiments, *E. coli* cells are used as hosts for the invention.

B. Antibody Production

Host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells.

Prokaryotic cells used to produce the polypeptides of the invention are grown in media known in the art and suitable for culture of the selected host cells. In some embodiments, the media also contains a selection agent, chosen based on the construction of the expression vector, to selectively permit growth of prokaryotic cells containing the expression vector.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents such as glutathione, cysteine, cystamine, thioglycollate, dithioerythritol or dithiothreitol.

The prokaryotic host cells are cultured at suitable temperatures. The pH of the medium may be any pH ranging from about 5 to about 9, depending mainly on the host organism.

If an inducible promoter is used in the expression vector of the invention, protein expression is induced under conditions suitable for the activation of the promoter. A variety of other inducers may be used, according to the vector construct employed, as is known in the art.

The expressed polypeptides of the present invention are secreted and recovered from the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Antibody production may be conducted in large quantity by a fermentation process. Various large-scale fed-batch fermentation procedures are available for production of recombinant proteins. Large-scale fermentations have at least 1,000 liters of capacity.

In a fermentation process, induction of protein expression is typically initiated after the cells have been grown under suitable conditions to a desired density. A variety of inducers may be used, according to the vector construct employed, as is known in the art and described above. Cells may be grown for shorter periods prior to induction. To improve the production yield and quality of the polypeptides of the invention, various fermentation conditions can be modified.

Antibodies can also be generated from eukaryotic host cells. The vector components generally include, but are not limited to, one or more of the following: a signal sequence, an origin of replication, one or more marker genes, an enhancer element, a promoter, and a transcription termination sequence. A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders are available. The DNA for such precursor region is ligated in reading frame to DNA encoding the antibody. An origin of replication component may not be needed for mammalian expression vectors. Expression and cloning vectors may optionally contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc. Alternatively, host cells transformed or co-transformed with DNA sequences encoding an antibody can be selected by cell growth in medium containing a selection agent for the selectable marker such as an aminoglycosidic antibiotic.

Expression and cloning vectors usually contain a promoter that is recognized by the host organism and is operably linked to the antibody polypeptide nucleic acid. Promoter sequences are known for eukaryotes. Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems. Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs.

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC® CRL 1651); human embryonic kidney line (293 or 293 cells subcloned for growth in suspension culture); baby hamster kidney cells (BHK, ATCC® CCL 10); Chinese hamster ovary cells/-DHFR(CHO); mouse sertoli cells; monkey kidney cells (CV1 ATCC® CCL 70); African green monkey kidney cells (VERO-76, ATCC® CRL-1587); human cervical carcinoma cells (HELA, ATCC® CCL 2); canine kidney cells (MDCK, ATCC® CCL 34); buffalo rat liver cells (BRL 3A, ATCC® CRL 1442); human lung cells (W138, ATCC® CCL 75); human liver cells (Hep G2, HB 8065); mouse mammary tumor (MMT 060562, ATCC® CCL51); TR1 cells; MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce an antibody of this invention may be cultured in a variety of media known to those of skill in the art. Examples of some commercially available media include Ham's F10 (Sigma), Minimal Essential Medium ((MEM), (Sigma), RPMI-1640 (Sigma), and Dulbecco's Modified Eagle's Medium ((DMEM), Sigma). Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™. drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

C. Antibody Purification

Standard protein purification methods known in the art can be employed to purify any antibody- or antibody fragment-containing composition of the present invention. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75. The antibody composition prepared from the cells may also be purified using, for example, hydroxylapatite chromatography, gel electrophoresis, dialysis, and affinity chromatography, with affinity chromatography being the preferred purification technique.

A preparation derived from a cell culture may be applied to or immobilized on a solid phase to allow specific binding of the antibody of interest. The solid phase is then washed to remove contaminants non-specifically bound to the solid phase. Finally the antibody of interest is recovered from the solid phase by elution.

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

V. Antibody Conjugates

In some embodiments there are immunoconjugates (also interchangeably termed "antibody-drug conjugates") comprising any of the anti-TEM8 antibodies described herein conjugated to a diagnostic or therapeutic agent.

A. Diagnostic Conjugates

Antibodies of the present invention may be linked to at least one agent to form an antibody conjugate. In order to increase the efficacy of antibody molecules as diagnostic or therapeutic agents, it is conventional to link or covalently bind or complex at least one desired molecule or moiety. By contrast, a reporter molecule is defined as any moiety which may be detected using an assay. Non-limiting examples of reporter molecules which have been conjugated to antibodies include enzymes, radioisotopes, haptens, fluorescent labels, phosphorescent molecules, chemilluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies. The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, "chlorine, $^{57}$cobalt, $^{58}$cobalt, copper", $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$, $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., B. Therapeutic Conjugates As stated above, in certain embodiments, the antibody may be conjugated to an effector molecule such as a therapeutic agent. Therapeutic agents comprise molecules having a desired activity, e.g., cytotoxic activity, immunomodulatory, or thrombogenic activity. Non-limiting examples of therapeutic agents which have been attached to antibodies include thrombogenic agents, toxins, anti-tumor agents (chemotherapeutic discussed above), therapeutic enzymes, lymphocyte binding domains, radionuclides (discussed above), cytokines, growth factors, and oligo- or polynucleotides. Some of these agents are discussed in greater deal elsewhere in this document, and that discussion will not be repeated here. Some particular agents of interest are described below.

The antibody also may be conjugated to a ribosome-inhibitory toxin (RIT). RITs are potent inhibitors of protein synthesis in eukaryotes. The enzymatic domain of these proteins acts as a cytotoxic n-glycosidase that is able to inactivate catalytically ribosomes once they gain entry to the intracellular compartment. This is accomplished by cleaving the n-glycosidic bond of the adenine at position 4324 in the 28srRNA, which irreversibly inactivates the ribosome apparently by disrupting the binding site for elongation factors. RITs, which have been isolated from bacteria, are prevalent in higher plants. In plants, there are two types: Type I toxins possess a single polypeptide chain that has ribosome inhibiting activity, and Type II toxins have an A chain, comparable to the Type I protein, that is linked by a disulfide bond to a B chain possessing cell-binding properties. Examples of Type I RITs are gelonin, dodecandrin, tricosanthin, tricokirin, bryodin, mirabilis antiviral protein, barley ribosome-inactivating protein (BRIP), pokeweed antiviral proteins (PAPs), saporins, luffins, and momordins. Type II toxins include ricin and abrin.

Toxins may be conjugated or expressed as a fusion protein with any of the polypeptides discussed herein. Toxins used in antibody-toxin conjugates include bacterial toxins such as diphtheria toxin, plant toxins such as ricin, small molecule toxins such as geldanamycin. The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Saporin is a protein that is useful in biological research applications, especially studies of behavior. Saporin is a so-called ribosome inactivating protein (RIP), due to its N-glycosidase activity, from the seeds of *Saponaria officinalis* (common name: soapwort). It was first described in 1983 in an article that illustrated the unusual stability of the protein. Among the RIP's are some of the most toxic molecules known, including ricin and abrin. These toxins contain second protein strand that inserts the RIP into a cell, making it able to enzymatically inactivate the ribosomes, shutting down protein synthesis and resulting in cell death, and eventually causing death of the victim. Saporin has no chain capable of inserting it into the cell. Thus, it and the soapwort plant are safe to handle. This has aided its use in research.

If given a method of entry into the cell, saporin becomes a very potent toxin, since its enzymatic activity is among the highest of all RIP's. The enzymatic activity of RIPs is unusually specific: a single adenine base is removed from the ribosomal RNA of the large subunit of the ribosome. This is the Achilles' heel of the ribosome; the removal of this base completely inhibits the ability of that ribosome to participate in protein synthesis. The fungal toxin alpha-sarcin cuts the ribosomal RNA at the adjacent base, also causing protein synthesis inhibition.

The conversion of saporin into a toxin has been used to create a series of research molecules. Attachment of saporin to something that enters the cell will convert it into a toxin for that cell. If the agent is specific for a single cell type, by being an antibody specific for some molecule that is only presented on the surface of the target cell type, then a set group of cells can be removed. This has many applications, some more successful than others. Saporin is not the only molecule that is used in this way; the enzymatic chain of ricin, the RIP gelonin, the enzymatic chain of *Pseudomonas* exotoxin, the enzymatic chain of diphtheria toxin have also been used, again with variations in success.

Other exemplary toxins include ricin A-chain (Burbage, 1997), diphtheria toxin A (Massuda et al., 1997; Lidor, 1997), pertussis toxin A subunit, *E. coli* enterotoxin toxin A subunit, cholera toxin A subunit and *Pseudomonas* toxin c-terminal are suitable. It has demonstrated that transfection of a plasmid containing the fusion protein regulatable diphtheria toxin A chain gene was cytotoxic for cancer cells. Still further exemplary toxins envisioned as useful for the present invention include abrin, A/B heat labile toxins, Botulinum toxin, *Helix pomatia*, Jacalin or Jackfruit, Peanut agglutinin, *Sambucus nigra*, Tetanus, *Ulex*, and Viscumin.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *sapaonaria officinalis* inhibitor, gelonin, mitogellin, restrictocin, phenomycin, enomycin, and the tricothecenes.

A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al. (1987). Carbon-14-labeled 1-isothiocyanatobenzyl-3-methyldiethylene triaminepentaacetic acid (MX-DTPA) is an exemplary chelating agent for conjugation of radionucleotide to the antibody.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein. Maytansinoids are mitototic inhibitors which act by inhibiting tubulin polymerization. In some embodiments, the immunoconjugate comprises an antibody of the invention conjugated to dolastatins or dolostatin peptidic analogs and derivatives, the auristatins. Dolastatins and auristatins have been shown to interfere with microtubule dynamics, GTP hydrolysis, and nuclear and cellular division and have anticancer. In other embodiments, the immunoconjugate comprises an antibody of the invention conjugated to one or more calicheamicin molecules. The calicheamicin family of antibiotics are capable of producing double-stranded DNA breaks at sub-picomolar concentrations.

In particular embodiments, the therapeutic agent is a thrombogenic agent. Non-limiting examples of thrombogenic agents include tissue factor (or a tissue factor peptide), cancer thrombogenic factor (CTF), doxorubicin, factor VIII, thalidomide, and homocysteine. The amino acid sequence of isoforms of human tissue factor is set forth as GenBank Accession No. NP_001984.1 (SEQ ID NO:22) and GenBank Accession No. NP_001171567.1 (SEQ ID NO:23), both of which are hereby incorporated by reference. The thrombogenic moiety may be a human tissue factor peptide of 5-100 amino acids in length, 5-50 amino acids in length, or 5-25 amino acids in length.

The monoclonal antibodies and antibody fragments of the present invention may also be conjugated to an anti-CD3 moiety.

The monoclonal antibodies and antibody fragments of the present invention may also be conjugated to other therapeutic monoclonal antibodies, such as anti-CD3 monoclonal antibodies (e.g., Muormonab-CD3) and anti-CD7 monoclonal antibodies. The conjugates may further be conjugated to a toxin moiety or thrombogenic agent.

In particular embodiments the therapeutic agent is an antiangiogenic agent. Non-limiting examples include drugs that block the proangiogenic function of vascular endothelial growth factor (VEGF). Other examples include SU5416, AG3340, endostatin, angiostatin, squalamine, thalidomide, CAI, Neovastat, and 2-methoxyestradiol.

VI. Nucleic Acid Molecules Encoding Antibodies or Antibody Fragments

Another embodiment pertains to nucleic acid molecules that encode the antibodies or antibody fragments described herein. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. A nucleic acid of the invention can be, for example, DNA or RNA and may or may not contain intronic sequences. In a specific embodiment, the nucleic acid is a cDNA molecule.

Nucleic acids of the invention can be obtained using standard molecular biology techniques. For antibodies expressed by hybridomas, cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the invention are those encoding the $V_H$ and $V_L$ sequences of SEQ ID NO:1 and SEQ ID NO:2. Other preferred nucleic acids of the invention are nucleic acids encoding amino acid sequences having at least 80% sequence identity, such as at least 85%, at least 90%, at least 95%, at least 98% or at least 99% sequence identity, with a nucleic acid encoding either SEQ ID NO:1 or SEQ ID NO:2, which nucleic acids encode an antibody of the invention, or an antigen-binding portion thereof. In some embodiments, the nucleic acid of the present invention comprises or consists of SEQ ID NO:19 and/or SEQ ID NO:20.

DNA fragments encoding $V_H$ and $V_L$ segments may be obtained, and these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the VH-encoding DNA to another DNA molecule encoding heavy chain constant regions (CH1, CH2 and CH3). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker.

VII. Uses

Antibodies may be used in, for example, in vitro, ex vivo, in situ, and in vivo therapeutic methods as well as diagnostic methods.

A. Therapeutic Methods

In some embodiments, methods are provided for reducing or inhibiting angiogenesis in a subject having a pathological condition associated with angiogenesis, comprising administering to the subject an effective amount of an anti-TEM8 antibody described herein. These conditions include, e.g., neoplasms, (including carcinomas) and certain eye conditions, such as conditions associated with neovascularization (e.g., age-related macular degeneration and other macular degenerations).

The cancers amendable for treatment by the present invention include, but not limited to, carcinoma, lymphoma, blastoma, sarcoma, and leukemia or lymphoid malignancies. More particular examples of such cancers include breast cancer, colon cancer, rectal cancer, colorectal cancer, kidney or renal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as abnormal vascular proliferation associated with phakomatoses, edema (such as that associated with brain tumors), and Meigs' syndrome. Preferably, the cancer is selected from the group consisting of breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, and multiple myeloma. More preferably, the cancer is colorectal cancer. The cancerous conditions amendible for treatment of the invention include metastatic cancers. The present invention is particularly suitable for the treatment of vascularized tumors.

The eye conditions amenable for treatment by the present invention include ocular neovascular diseases, including, but not limited to, age-related macular degeneration, diabetic macular edema, proliferative diabetic retinopathy, central retinal vein occlusion with cystoid macular edema, branch retinal vein occlusion with cystoid macular edema, rubeosis irides, pathologic myopia/CNV, Von Hippel Lindau Syndrome, pterygium, POHS (Histoplasmosis)/CNV, choroidal hemangiomas, retinopathy of prematurity (ROP), radiation retinopathy, intraocular tumors (e.g. melanoma, retinoblastoma, metastases, and cavernous hemangiomas of the orbit), polypoidal choroidopathy, idiopathic juxtafoveal telangiectasis, Eales' Disease, cavernous hemangiomas of the orbit, orbital lymphangiomas, capillary hemangiomas of the eyelid, corneal graft vascularization, corneal graft neovascularization, Coats Disease, and wound healing problems associated with glaucoma surgery.

Moreover, at least some of the antibodies of the invention can bind antigen from other species. Accordingly, the antibodies of the invention can be used to bind specific antigen activity, e.g., in a cell culture containing the antigen, in human subjects or in other mammalian subjects having the antigen with which an antibody of the invention cross-reacts (e.g. chimpanzee, baboon, marmoset, cynomolgus and rhesus, pig or mouse). In some embodiments, the antibody of the invention can be used for inhibiting antigen activities by contacting the antibody with the antigen such that antigen activity is inhibited. Preferably, the antigen is a human protein molecule.

In some embodiments, an antibody or antibody fragment of the invention can be used in a method for binding an antigen in a subject suffering from a disorder associated with increased antigen expression and/or activity, comprising administering to the subject an antibody of the invention such that the antigen in the subject is bound. Preferably, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the immunoglobulin cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration).

The antibodies of the invention can be used to treat, inhibit, delay progression of, prevent/delay recurrence of, ameliorate, or prevent diseases, disorders or conditions associated with expression and/or activity of TEM8.

In certain embodiments, an immunoconjugate comprising an antibody conjugated with one or more therapeutic agent (s) is administered to the patient. In some embodiments, the immunoconjugate and/or antigen to which it is bound is/are internalized by the cell, resulting in increased therapeutic efficacy of the immunoconjugate in killing the target cell to which it binds. In one embodiment, the cytotoxic agent targets or interferes with nucleic acid in the target cell. In one embodiment, the cytotoxic agent targets or interferes with microtubule polymerization. Examples of such cytotoxic agents include any of the chemotherapeutic agents noted herein (such as a maytansinoid, auristatin, dolastatin, or a calicheamicin), a radioactive isotope, or a ribonuclease or a DNA endonuclease.

A different therapeutic approach to increase the radiation dose delivered to tumor compared with blood and other normal tissues has involved reengineering of the targeting antibody molecule as a bispecific antibody (bsAb). This is made chemically or recombinantly from monovalent antibody fragments that target 2 different antigens, one at the tumor (surface TEM8) and the other a hapten chelate. After the bsAb localizes in the tumor and clears from normal tissues, the second agent, which binds selectively to the second arm of the antibody and delivers the radioactivity to the tumor, is administered.

B. Diagnostic Methods

The anti-TEM8 antibodies are useful in assays detecting TEM8 expression (such as diagnostic or prognostic assays) in specific cells or tissues wherein the antibodies are labeled as described below and/or are immobilized on an insoluble matrix.

Methods are provided for detection of TEM8. In some embodiments, methods compare detecting TEM8-anti-TEM8 antibody complex in the sample. The term "detection" as used herein includes qualitative and/or quantitative detection (measuring levels) with or without reference to a control.

Also provided are methods for diagnosing a disorder associated with TEM8 expression and/or activity. In some embodiments, the methods comprise detecting TEM8-anti-TEM8 antibody complex in a biological sample from a patient having or suspected of having the disorder. In additional embodiments, the TEM8 expression is increased expression or abnormal (undesired) expression.

Embodiments may involve any of the anti-TEM8 antibodies described herein. In some embodiments the anti-TEM8 antibody comprises a detectable label. Isotopes may be conjugated to monoclonal antibodies (mAbs) or fragments of the invention for use in dual imaging and therapy (radioimmunodetection and radioimmunotherapy).

Compositions and methods may involve a complex of any of the anti-TEM8 antibodies described herein and TEM8. In some embodiments, the complex is in vivo or in vitro. In some embodiments, the complex comprises a cancer cell. In some embodiments, the anti-TEM8 antibody is detectably labeled.

Anti-TEM8 antibodies can be used for the detection of TEM8 in any one of a number of well known detection assay methods. For example, a biological sample may be assayed for TEM8 by obtaining the sample from a desired source, admixing the sample with anti-TEM8 antibody to allow the antibody to form antibody/TEM8 complex with any TEM8 present in the mixture, and detecting any antibody/TEM8 complex present in the mixture. The biological sample may be prepared for assay by methods known in the art which are suitable for the particular sample. The methods of admixing the sample with antibodies and the methods of detecting antibody/TEM8 complex are chosen according to the type of assay used. Such assays include immunohistochemistry, competitive and sandwich assays, and steric inhibition assays.

Analytical methods for TEM8 all use one or more of the following reagents: labeled TEM8 analogue, immobilized TEM8 analogue, labeled anti-TEM8 antibody, immobilized anti-TEM8 antibody and steric conjugates. The labeled reagents also are known as "tracers."

The label used is any detectable functionality that does not interfere with the binding of TEM8 and anti-TEM8 antibody. Numerous labels are known for use in immunoassay, examples including moieties that may be detected directly, such as fluorochrome, chemiluminescent, and radioactive labels, as well as moieties, such as enzymes, that must be reacted or derivatized to be detected.

The label used is any detectable functionality that does not interfere with the binding of TEM8 and anti-TEM8 antibody. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes 32P, 14C, 125I, 3H, and 131I, fluorophores such as rare earth chelates or fluorescein and its derivatives, rhodamine and its derivatives, dansyl, umbelliferone, luceriferases, e.g., firefly luciferase and bacterial luciferase, luciferin, 2,3-dihydrophthalazinediones, horseradish peroxidase (HRP), alkaline phosphatase, .beta.-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. Examples of labels herein are enzymes such as horseradish peroxidase and alkaline phosphatase. The conjugation of such label, including the enzymes, to the antibody is a standard manipulative procedure for one of ordinary skill in immunoassay techniques.

Immobilization of reagents is required for certain assay methods. Immobilization entails separating the anti-TEM8 antibody from any TEM8 that remains free in solution. This conventionally is accomplished by either insolubilizing the anti-TEM8 antibody or TEM8 analogue before the assay procedure, as by adsorption to a water-insoluble matrix or surface.

The expression of proteins in a sample may be examined using immunohistochemistry and staining protocols. Immunohistochemical staining of tissue sections has been shown to be a reliable method of assessing or detecting presence of proteins in a sample. Immunohistochemistry ("IHC") techniques utilize an antibody to probe and visualize cellular antigens in situ, generally by chromogenic or fluorescent methods. For sample preparation, a tissue or cell sample from a mammal (typically a human patient) may be used. The sample can be obtained by a variety of procedures known in the art including, but not limited to surgical excision, aspiration or biopsy. The tissue may be fresh or frozen. In one embodiment, the sample is fixed and embedded in paraffin or the like. The tissue sample may be fixed (i.e. preserved) by conventional methodology. One of ordinary skill in the art will appreciate that the choice of a fixative is determined by the purpose for which the sample is to be histologically stained or otherwise analyzed. One of ordinary skill in the art will also appreciate that the length of fixation depends upon the size of the tissue sample and the fixative used.

IHC may be performed in combination with additional techniques such as morphological staining and/or fluorescence in-situ hybridization. Two general methods of IHC are available; direct and indirect assays. According to the first assay, binding of antibody to the target antigen (e.g., TEM8) is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available for this purpose.

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. The label may be an enzymatic label which catalyzes a chemical alteration of the chromogenic substrate such as 3,3'-diaminobenzidine chromogen. The enzymatic label may be conjugated to antibody which binds specifically to the primary antibody (e.g. the primary antibody is rabbit polyclonal antibody and secondary antibody is goat anti-rabbit antibody).

Other assay methods, known as competitive or sandwich assays, are well established and widely used in the commercial diagnostics industry. The assay may be a competitive assay.

Sandwich assays may also be used for the determination of TEM8 or anti-TEM8 antibodies. The foregoing are merely exemplary detection assays for TEM8. Other methods now or hereafter developed that use anti-TEM8 antibody for the determination of TEM8 are included within the scope hereof, including the bioassays described herein.

In still further embodiments, the present invention concerns immunodetection methods for binding, purifying, removing, quantifying and otherwise generally detecting tumor endothelial cells expressing TEM8. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of RSV antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample and contacting the sample with a first antibody in accordance with the present invention, as the case may be, under conditions effective to allow the formation of immunocomplexes.

These methods include methods for purifying a TEM8-expressing cell or related antigens from a sample. The antibody will preferably be linked to a solid support, such as in the form of a column matrix, and the sample will be applied to the immobilized antibody. The unwanted components will be washed from the column, leaving the antigen immunocomplexed to the immobilized antibody, which is then collected by removing the organism or antigen from the column.

The immunobinding methods also include methods for detecting and quantifying the amount of TEM8-expressing cells in a sample and the detection and quantification of any immune complexes formed during the binding process. Here, one would obtain a sample, and contact the sample with an antibody, followed by detecting and quantifying the amount of immune complexes formed under the specific conditions. In terms of antigen detection, the biological sample analyzed may be any sample, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

VIII. Administration of Anti-TEM8 Antibodies

The use of anti-TEM8 antibodies and antisera to treat cancer is contemplated in embodiments, and optionally for the in situ diagnosis of cancer and other diseases associated with abnormal angiogenesis. The antibodies may themselves be therapeutic effectors, or alternatively, they may be conjugated to therapeutic agents such as toxins, radionuclides or chemotherapeutic agents. It is contemplated that the antibodies will be administered in such dosages, routes and regimens to effect a therapeutic benefit, ranging from destruction of cancer cells and tumor tissue, to inhibition or reduction of tumor growth, reduction of tumor burden, reduction in metastatic potential, rendering the cancer/tumor susceptible to another treatment (e.g., rendering a drug-resistant tumor drug-sensitive, rendering an inoperable tumor operable), or simply improve the quality of life or longevity of a cancer patient.

The antibody/antibody fragment composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above.

The antibody of the invention (and adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody may be administered by pulse infusion, particularly with declining doses of the antibody. Dosing can be by any suitable route, e.g. by injections, such as intravenous or subcutaneous injections, depending in part on whether the administration is brief or chronic.

For the prevention or treatment of disease, the appropriate dosage of an antibody or antibody fragment of the invention when used alone or in combination with other agents will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 0.01 microgram/kg to 15 mg/kg (e.g. 0.1 mg/kg-10 mg/kg) of antibody is an initial candidate dosage for administration to the patient, whether, for example, by one or more separate administrations, or by continuous infusion. One typical daily dosage might range from about 1 microgram/kg to 100 mg/kg or more, depending on the factors mentioned above. For repeated administrations over several days or longer, depending on the condition, the treatment is sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Therapeutic formulations comprising an antibody and/or antibody fragment of the invention are prepared for storage by mixing the antibody or fragment having the desired degree of purity with optional physiologically acceptable carriers, excipients or stabilizers (see, e.g., Remington: The Science and Practice of Pharmacy 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides, copolymers of L-glutamic acid and .gamma. ethyl-L-glutamate, non-degradable ethylene-vinyl acetate, degradable lactic acid-glycolic acid copolymers. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37.degree. C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

In a particular embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection.

The ingredients of compositions of the invention may be in unit dosage form. Where the composition is to be administered by infusion, it can be dispensed with an infusion bottle containing sterile pharmaceutical grade water or saline.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Antibodies or antibody fragments of the invention can be used either alone or in combination with other compositions in a therapy. For instance, an antibody or antibody fragment of the invention may be co-administered with chemotherapeutic agent(s) (including cocktails of chemotherapeutic agents), other cytotoxic agent(s), anti-angiogenic agent(s), cytokines, thrombotic agents, and/or growth inhibitory agent(s). Such combined therapies noted above include combined administration (where the two or more agents are included in the same or separate formulations), and separate administration, in which case, administration of the antibody of the invention can occur prior to, and/or following, administration of the adjunct therapy or therapies.

Combination therapy may be achieved by use of a single pharmaceutical composition that includes both agents, or by administering two distinct compositions at the same time, wherein one composition includes the antibody of the present invention and the other includes the second agent(s).

The two therapies may be given in either order and may precede or follow the other treatment by intervals ranging from minutes to weeks. In embodiments where the other agents are applied separately, one would generally ensure that a significant period of time did not expire between the time of each delivery, such that the agents would still be able to exert an advantageously combined effect on the patient. In such instances, it is contemplated that one may administer both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Administration of the secondary agent will follow general protocols for that drug, taking into account the toxicity, if any. It is expected that the treatment cycles would be repeated as necessary. Various combination therapies are considered, as discussed below, but in particular, therapies that complement the anti-angiogenic activity of anti-TEM8 antibodies are particularly useful, such as Bevacizumab, Sunitinib, Sorafenib, Macugen, Lucentis, Tryptophanyl-tRNA, AdPEDF, VEGF-TRAP-EYE, AG-013958, JSM6427, TG100801, ATG3, Endostatin, Pazopanib and Perceiva. In general, an "anti-cancer" agent or therapy for use in combination with the present invention includes any therapeutic modality capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. Some examples of these therapies include chemotherapy. Some examples of chemotherapeutic agents have been previously set forth; other examples include cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristine, vinblastine and methotrexate, Temazolomide (an aqueous form of DTIC), or any analog or derivative variant of the foregoing.

In particular embodiment, the secondary agent is an agent that has activity against MET-HSF such as but not limited to anti-MET antibodies or MET tyrosine kinase inhibitors. Non-limiting examples of such agents include BMS-777607. Examples of molecules that inhibit MET function can be found in U.S. 20080058312, US 20070213319, U.S. 20070123534, U.S. 20070117802, US 20070179130, and U.S. 20070203136, each of which is herein specifically incorporated by reference in its entirety.

The antibodies and antibody fragments of the present invention may also be administered in combination with radiotherapy, surgical therapy, immunotherapy (particularly radioimmunotherapy), gene therapy, or any other therapy known to those of ordinary skill in the art for treatment of a disease or disorder associated with vascular proliferation, such as any of the diseases or disorders discussed elsewhere in this specification.

IX. Kits

Embodiments also concern kits that include an article of manufacture such as a container comprising antibodies or antibody fragments of the invention. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition(s) effective for treating, preventing and/or diagnosing the condition and may have a sterile access port (for example the container may be an intravenous solution bag or a vial having a stopper pierceable by a hypodermic injection needle). At least one active agent in the composition is an antibody or antibody fragment of the invention. The label or package insert indicates that the composition is used for treating the condition of choice, such as cancer. Moreover, the article of manufacture may comprise (a) a first container with a composition contained therein, wherein the composition comprises an antibody or antibody fragment of the invention; and (b) a second container with a composition contained therein. The article of manufacture in this embodiment of the invention may further comprise a package insert indicating that the first and second antibody or antibody fragment compositions can be used to treat a particular condition, e.g. cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In still further embodiments, the present invention concerns immunodetection kits for use with the immunodetection methods described above. As the anti-TEM8 antibodies may be used to detect TEM8 antigens, the antibodies will be included in the kit. The immunodetection kits will thus comprise, in suitable container means, a first antibody or antibody fragment that binds to TEM8, and optionally an immunodetection reagent.

In certain embodiments, the anti-TEM8 antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present invention.

The kits may further comprise a suitably aliquoted composition of the TEM8 antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kit may include a column and/or column packing material. The kits of the present invention will also typically include a means for containing the antibody, antigen, and any other reagent containers in close confinement for commercial sale. Such containers may include injection or blow-molded plastic containers into which the desired vials are retained.

The kit of the present invention may optionally include one or more nucleic acid sequences each comprising a primer sequence as set forth in the present disclosure. Primer sequences are set forth in the examples section below. In certain embodiments, methods and compositions may involve any of SEQ ID NOs:1-28. In certain embodiments, 1, 2, 3, 4 or more of SEQ ID NOs 1-28 are involved.

X. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods

Cell Lines and Culture Conditions. 293 cells, DLD-1, SK-BR-3, HUVEC and T/G HA-VSMC were from ATCC. HT29 was from the DCTD Tumor Repository at NCI (Frederick, Md.) HAECs were from Coriell (Camden, N.J.), HMECs were from the CDC (Atlanta, Ga.), and coronary SMC and uterine SMC were from Lonza (Walkersville, Md.). Endothelial cells were cultured in EBM-2 (Lonza), smooth muscle cells in SmGM-2, (Lonza), and all other cells in DMEM supplemented with 10% fetal bovine serum.

Incorporation of a FLAG-tag onto TEM8. A two-step PCR-based strategy was used to incorporate a 3×FLAG-tag onto the N-terminus of TEM8 immediately following the signal peptide. In the first step, two separate PCR products were generated on either side of the FLAG insertion site using as template a TEM8/pcDNA3.1 vector containing a CMV-driven full length human TEM8 cDNA (sv1 isoform, Genbank Acc. # AF279145). The primers used for product A were:

```
A-For:
                                           (SEQ ID NO: 29)
5'-AGGCGTGTACGGTGGGAG-3'
and A-Rev:
                                           (SEQ ID NO: 30)
5'-CTTGTCATCGTCATCCTTGTAATCGATGTCATGATCTTTATAATC
ACCGTCATGGTCTTTGTAGTCCCCGGCGCAGATGAGC-3'
``` and for product B were:

```
B-For:
                                           (SEQ ID NO: 31)
5'-GATTACAAGGATGACGATGACAAGCAAGGGGACGCAGGG-3'
and B-Rev:
                                           (SEQ ID NO: 32)
5'-CTGGTGAAGTTGATGCAGCG-3'.
```

The primers included a 3×-FLAG tag DNA sequence as indicated by bold lettering, and a small 24 bp complementary region of overlap between the two products (underlined). After PCR amplification, the two PCR products were gel purified, mixed, and used as a template in a second PCR reaction that utilized the outside primers: A-For and B-Rev. The resultant PCR product containing the FLAG sequence, product C, was then digested with the restriction enzymes BamH1 and EcoR1 and gel purified to remove the amplicon ends. The parent TEM8/pcDNA3.1 vector was also digested BamH1 and EcoR1, and the vector backbone gel purified. The PCR-generated purified product C was cloned into the vector backbone, and the resulting plasmid, called 3×-FLAG-T8/pcDNA3.1, was verified mutation-free by DNA sequencing.

Immunomagnetic Bead Selection. SB5 was biotinylated (Pierce, Rockford, Ill.) and mixed with Streptavidin M-280 magnetic Dynabeads (Invitrogen, Carlsbad, Calif.) to generate SB5-beads. Prior to positive cell selection with SB5-beads, cells were pre-incubated with streptavidin-beads pre-bound to biotin-labeled non-specific IgG to remove any non-specific binders. Following positive selection, cells were expanded and passaged until no bead-bound cells were visible, and the selection was repeated until all cells were SB5-positive by flow cytometry.

Immunoblotting. Immunoblotting was performed as previously described (Nanda et al., 2004). Partial epitope mapping of the SB2, SB4, SB8 and SB12 mAbs was performed using GST-TEM8 peptide deletions as described for SB5 (Cullen et al., 2009). To evaluate cross-reactivity with CMG2, cellular lysates were derived from CHO-PR230 (CHO) cells, CHO/TEM8 cells and CHO/CMG2 cells (cells were a kind gift from Drs. Stephan H. Leppla and Shihui Liu). To evaluate cross-reactivity with mouse TEM8, an expression vector (pcDNA3/mTEM8) was generated, sequence verified, and stably transfected into 293 cells.

Immunoprecipitation. αSMA was cloned into the expression vector pcDNA3.1/hygro (Invitrogen) and stably transfected into 293/T8-SB5 cells. Total cell lysates were incubated overnight with SB5 anti-TEM8 antibodies, anti-αSMA antibody (Sigma, St. Louis, Mo.) or nonspecific mouse IgG control antibody at 4° C. Protein G-agarose beads (Roche, Indianapolis, Ind.) or streptavidin agarose beads (Sigma) were added and incubated at 4° C. for 2 hrs. Precipitated proteins were separated by SDS-PAGE and detected by immunoblotting with either SB5 anti-TEM8 antibody, anti-αSMA antibody or anti-FLAG antibody (Sigma, M2 clone) followed by HRP-anti-mouse IgG F(ab')2 fragment specific (Jackson Immunoresearch).

Biotinylation experiments. 293, 293/TEM8c1, or 293/T8-SB5 cells grown on Poly-D-lysine coated plates were rinsed with cold PBS and labeled with 0.5 mM sulfo-NHS-SS-biotin (Thermo Scientific—Pierce) in cold PBS for 40 min. at 4° C. according to the manufactures protocol. Immunoprecipitation and immunoblotting of biotinylated proteins was performed as outlined above (previous two sections)

Immunofluorescence. Cells grown on poly-L-lysine treated chamber slides were chilled on ice and SB5 anti-TEM8 or anti-FLAG mAbs (M2 clone) were added directly to the growth medium for 30 min at 4° C. Cells were washed with cold medium, fixed in cold 4% paraformaldehyde in PBS and labeled with FITC-conjugated goat anti-mouse IgG. To detect TEM8 with SB5 (a mouse $IgG_1\kappa$) and AF334 (a mouse IgM κ) simultaneously, in this case the primary antibodies were detected with either a DyLight 488-conjugated goat anti-mouse IgG1, Fcγ specific (Jackson, cat #115-485-205) or a DyLight 594-goat anti-mouse IgM, μ chain specific antibody (Jackson, cat #115-515-075). For dual-color staining of TEM8 and αSMA, FlagT8-SB5/αSMA cells which had been permeabilized with 0.1% Triton-X 100 were labeled with rat-anti-FLAG (Biolegend) and mouse anti-α-SMA mAbs followed by a secondary layer of FITC-linked goat anti-rat and biotin-linked donkey anti-mouse IgG (Jackson) and a third layer of 488-linked donkey anti-FITC and Texas red-streptavidin (Vector). Sections were counterstained with DAPI and immunofluorescent images captured using a Nikon Eclipse E600 microscope or a Zeiss LSM510 confocal microscope.

TEM8 Internalization Experiment. SB5 or control IgG labeled with Cy5.5 (Thermo Fisher Scientific) was added to the culture medium of cells grown on poly-L-lysine treated chamber slides and incubated at 37° C. for 3 hr. On ice, cells were rinsed with PBS, fixed with 4% paraformaldehyde, and TEM8 present on the cell surface was detected by post-staining with FITC-conjugated goat anti-mouse IgG antibody.

Identification of Genes that Regulate SB5-Toxin Sensitivity by Expression Cloning. An MMLV-based cDNA library from uterus (ViraPortXR, Stratagene) was prepared and used to infect exponential-phase 293/FlagT8-SB5 cells on ten 100 mm plates according to the manufactures recommendations. Virus infected FlagT8-SB5 cells were treated with 40 nM TSA and 5 nM saporin-streptavidin (Advanced Targeting Systems) and biotinylated-SB5. Surviving colonies were expanded and selected with magnetic Dynabeads (Pan-mouse IgG, Invitrogen) that had been pre-armed with anti-Flag mAbs. After repeating the SB5-toxin treatment and SB5-bead selection once more, surviving cells were cloned by limiting dilution and genomic DNA from each clone was isolated using the DNeasy blood and tissue kit (Qiagen). Each insert was identified by PCR using the primer pair, F: CAGCTTGGATACACGCCG (SEQ ID NO:3), and R: TGCCAAACCTACAGGTGGG (SEQ ID NO:4).

Cell Viability Assay. Cells were plated on poly-L-lysine treated 96-well plates overnight. The next day, biotinylated SB5 and saporin-streptavidin or mouse anti-Flag mAbs and anti-mouse-saporin conjugates were pre-incubated together at RT for 20 min and then added to cells. 72 hours later, medium was replaced with fresh medium containing 10% AlarmarBlue (Invitrogen) and fluorescence measured at 560 nm/590 nm (Ex/Em) in a spectrophotometer 4 hours later. Brightfield images were captured 72 hr or 96 hours post-treatment.

Flow Cytometry. Following trypsinization, at 4° C. cells were rinsed in PBS/0.5% BSA (PBS/BSA), incubated in PBS/BSA containing primary mAbs, rinsed, incubated with PBS/BSA containing FITC-conjugated secondary (Jackson Immunoresearch), rinsed and analyzed in a FACSCalibur flow cytometer (BD).

RT-PCR. RT-PCR was performed using total RNA isolated from cells using RNeasy mini kit (Qiagen) and cDNA was synthesized using Superscript III 1$^{st}$ strand synthesis system (Invitrogen). The primer pairs used were

```
vWF-F:
                                            (SEQ ID NO: 5)
CGGCAGGTCATCCACGG vWF-R:
                                            (SEQ ID NO: 6)
CGGACAGCTTGTAGTACCCAG

VE-Cad-F:
                                            (SEQ ID NO: 7)
TGCTAACCCTGCCCAACG

VE-Cad-R:
                                            (SEQ ID NO: 8)
CCTCTCAATGGCGAACACG

PDGFRβ-F:
                                            (SEQ ID NO: 9)
TGTCCCTGTCCGAGTGCTG

PDGFRβ-R:
                                            (SEQ ID NO: 10)
CCAGGATGGCTGAGATCACC

TAGLN-F:
                                            (SEQ ID NO: 11)
CCCATCCTGTCTGTCCGAAC
```

-continued

TAGLN-R:
(SEQ ID NO: 12)
CACGCCATTCTTCAGCCAG

α-SMA-F:
(SEQ ID NO: 13)
GCCGACCGAATGCAGAAG

α-SMA-R:
(SEQ ID NO: 14)
GGACATTCACAGTTGTGTGCTAG

TEM8-F:
(SEQ ID NO: 15)
GCCAACGGTAGACGCCTC

TEM8-R:
(SEQ ID NO: 16)
TAGGACCCACAAGGCATCG

Eif4H-F:
(SEQ ID NO: 17)
CGTAGCCAGAAGGAGTTGCC

Eif4H-R:
(SEQ ID NO: 18)
ATGTCCACACGAAGTGACCG.

Generation of AF334 Anti-TEM8 mAb. CHO cells and CHO cells transfected with full-length human TEM8 (CHO/TEM8) (Chen et al., 2007) were maintained in alpha MEM supplemented with glutamine, gentamicin, HEPES and hygromycin. CHO/TEM8 cells were enriched for high surface expression of TEM8 by three sequential rounds of flow cytometry sorting (BD FACSAria) by staining cells with PA. PA was prepared as described (Watson et al., 2007) and conjugated with sulfo-NHS-LC-biotin using a kit (Thermo Fisher Scientific). Cells were labeled in 0.5 mL PBS/1% BSA on ice for 15 min with 10 mcg/mL biotin-PA, rinsed with PBS, incubated with 2 mcg/mL streptavidin-R-PE (BioLegend, San Diego, Calif.) in PBS/1% BSA, rinsed, and resuspended with PBS. The highest 6% positive cells were selected in each sort. 2.5 million TEM8 surface-enriched CHO/TEM8 cells were administered by intraperitoneal injection in 0.2 mL PBS monthly to BALB/c female two month old mice. Monthly inoculations were repeated three additional times and splenocytes harvested three days after the last boost. Splenocytes were fused 1:1 with OUR-1 mouse myeloma cells in Opti-MEM in the presence of 50% PEG (Invitrogen) following the manufactures protocol. Hybridomas were grown in Opti-MEM supplemented with HAT and 10% FBS. Supernatants were screened by differential flow cytometry binding to CHO/TEM8 versus CHO cells using FITC conjugated goat anti-mouse Ig (Invitrogen). A secondary screen was done using an enzyme-linked immunoassay with membrane preparations made by sonication of CHO or CHO/TEM8 cells as previously described (Chen et al., 2007). The hybridoma showing the highest supernatant reactivity was subcloned three times by limiting dilution, expanded, cryopreserved, and designated AF334. The AF334 hybridoma produced an IgMκ which reacted specifically with CHO/TEM8 but not CHO or CHO/CMG2 cells by flow cytometry. AF334 also reacted with both 293/mTEM8 and 293/hTEM8 cells, but not 293 cells, demonstrating cross-reactivity with the mouse protein. The AF334 hybridoma maintained stable expression after weaning into serum free PFHM II medium (Invitrogen). Supernatants were concentrated and antibodies were purified by gel filtration.

Example 2

Results and Discussion

SB Antibodies are specific for TEM8 and recognize the soluble extracellular domain. A panel of mouse mAbs, the "SB" series, was previously developed against the full extracellular domain of human TEM8 using purified recombinant proteins (Nanda et al., 2004). To determine if these mAbs cross-react with the mouse TEM8 protein (mTEM8), the inventors tested them by western blotting using lysates of 293 cells transfected with a full-length mTem8 expression vector. Four of the five mAbs tested, called SB2, SB4, SB5 and SB12, reacted with both mouse and human TEM8, whereas SB8 was human-specific (FIG. 1A). High cross-species reactivity is not unexpected given the high level of similarity (98%) between the mouse and human proteins. The inventors also tested SB mAbs by western blotting against cells transfected with CMG2, the closest homologue of TEM8, and found that none of the mAbs cross-react (FIG. 1A).

Figure 1C:
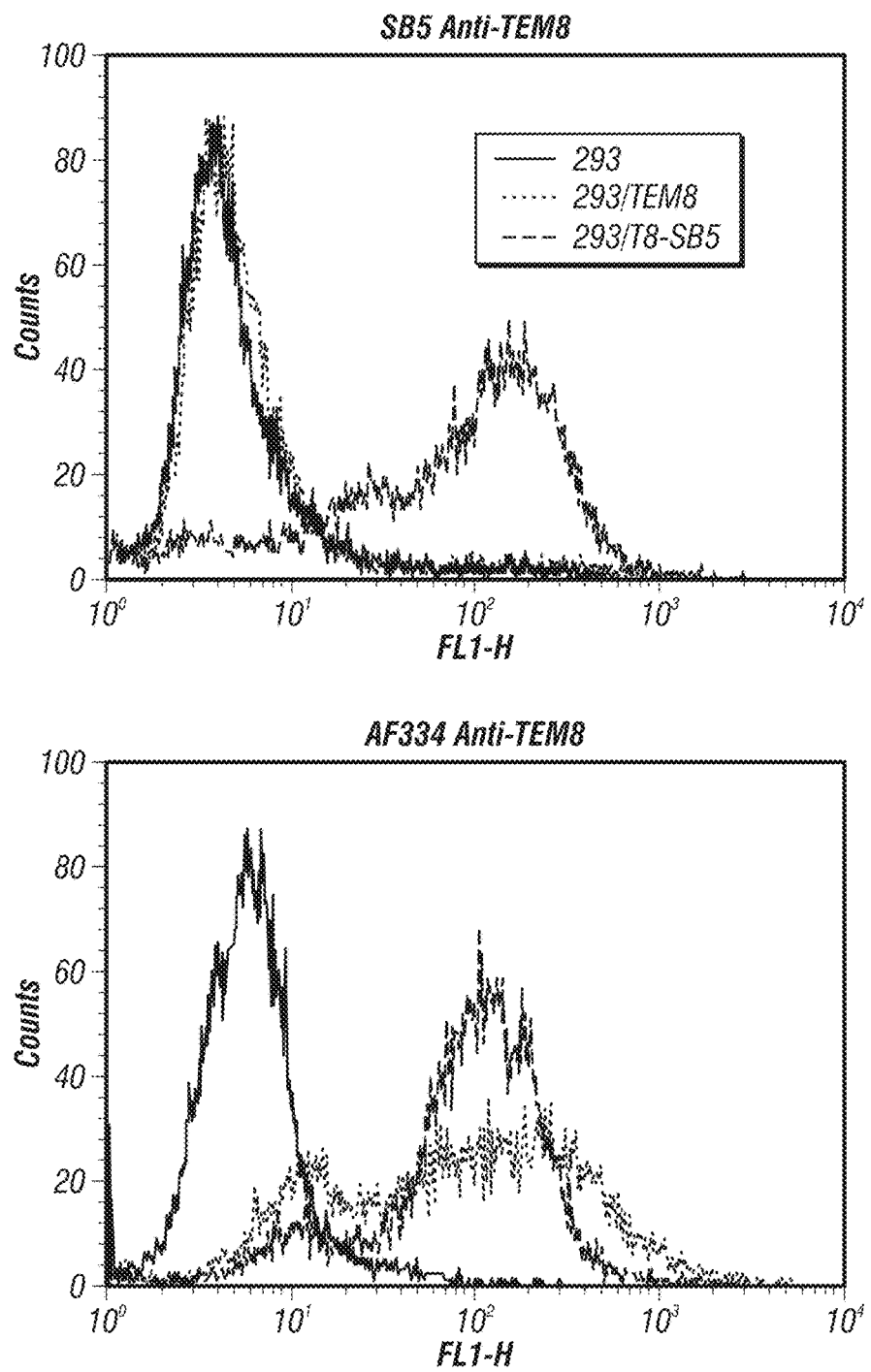

Next, the inventors developed a capture ELISA to determine if any of the SB mAbs could bind the native extracellular domain of TEM8 fused to alkaline phosphatase (AP-TEM8). Although several mAbs were able to bind soluble AP-TEM8 fusion protein, SB5 bound best and none of the mAbs reacted with the control proteins AP-TEM7 or AP alone (FIG. 1B). SB5 antibody also worked best for western blotting and immunoprecipitation of TEM8, without any apparent cross-reactivity to other proteins (see Nanda et al., 2004). However, each of the SB mAbs failed to detect significant levels of cell-surface TEM8 on 293 cells stably transfected with a full-length TEM8 expression vector (FIG. 1C). They also tested several commercially available antibodies each of which failed to detect native TEM8 at the cell surface. The lack of cell surface staining was not cell type specific because these antibodies also failed to detect TEM8 on the surface of TEM8-positive primary endothelial cells and TEM8 transfected CHO cells. Despite this lack of staining, TEM8 was presumably present on the surface of 293/TEM8 cells based on cell surface labeling with non-permeable biotin and subsequent studies which employed a tagged version of the receptor and a newly developed antibody (see below). Based on this, the inventors hypothesized that the epitope for SB5 and other currently available anti-TEM8 antibodies is normally masked on the surface of 293/TEM8 cells.

SB5 antibodies recognize a cryptic subpopulation of 293/TEM8 cells. While performing immunofluorescence staining for cell surface TEM8 in 293/TEM8 cells using SB5 antibodies, the inventors noticed a very small fraction of the cells (<0.5%) were strongly positive, while 293 parent cells were completely negative. These positive cells were not apparent by flow cytometry analysis due to their low frequency. In order to determine if this rare fraction of the 293/TEM8 parent population could be enriched, the inventors purified these cells using SB5-linked magnetic beads. After expanding the SB5-bead bound cells in culture and repeating the selection and expansion 3 more times, they were able to obtain a variant subline, called 293/hT8-SB5, that uniformly reacted with SB5 mAbs by both immunofluorescence and flow cytometry. Likewise, when they repeated the SB5-selection using 293 cells transfected with mouse TEM8 (293/mT8-SB5) again they were able to derive sublines, this time with mTEM8 detectable on the cell surface, while parallel control selections performed on parent 293 cells failed to result in any enrichment. Importantly, SB8 human-specific anti-TEM8 mAbs labeled the cell surface of 293/hT8-SB5 cells similar to SB5 but failed to detect mouse TEM8 on the surface of 293/mT8-SB5 cells. Because SB5 and SB8 recognize independent epitopes, this result confirmed the specificity of these antibodies for TEM8. Preliminary mapping of the SB antibody binding sites using peptide deletions of the TEM8 extracellular domain revealed that SB5 and SB8 mAbs recognize distinct epitopes separated by at least 123 amino acids (FIG. 1A). Immunoblotting with several independent SB mAbs also revealed smaller 35 to 50 kDa products in the SB5-selected cells which presumably represent intracellular degradation products of the TEM8 extracellular domain because these fragments, unlike the full-length 85 kDa product, were not labeled with biotin immediately following cell surface biotinylation. Throughout these studies, the small TEM8 fragments were always observed in cells that displayed surface-exposed SB5 binding sites, but never in cells with an SB5-masked form of TEM8, thus providing an index of SB5 accessibility.

SB5 anti-TEM8 Antibodies are Internalized. Anthrax toxin proteins bind TEM8 or CMG2 and are taken up into cells through a highly regulated endocytosis-mediated process (Singh et al., 1999; Abrami et al., 2003), but internalization of anti-TEM8 antibodies has not yet been described. To determine if SB5 mAbs could be taken up by 293/T8-SB5 cells, the inventors labeled SB5 with Cy5.5 and followed its uptake in live cells. Cy5.5-SB5 could be readily observed inside cells as early as 30 minutes following treatment, and most was taken up into the cells by 3 hours. Some Cy5.5-SB5 signal (red) could also be detected on the surface 3 hours following internalization, which was verified by fixing the cells and amplifying the surface bound Cy5.5-SB5 signal with a FITC-labeled anti-mouse secondary antibody.

Figure 2B:
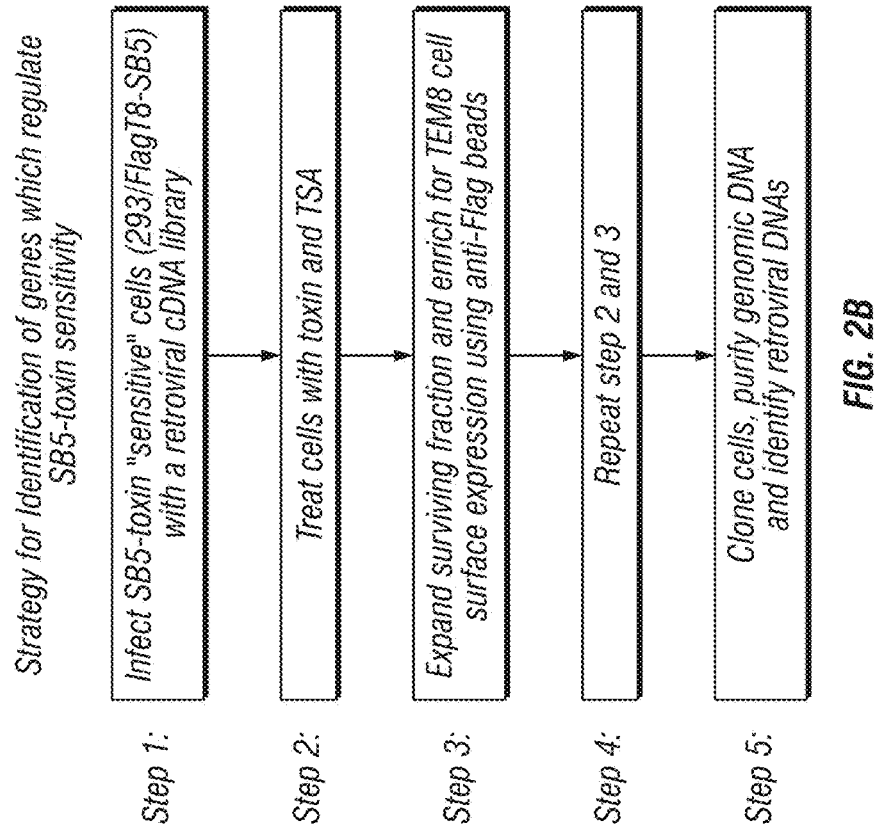
FIGS. 2A-B. SB5-saporin immunotoxins are internalized and selectively kill 293/T8-SB5 cells. A. 1 nM or 10 nM of saporin-streptavidin toxin combined with biotin-labeled SB5 selectively killed 293/T8-SB5 cells (bottom panel) compared to saporin-streptavidin alone (top panel).
Figure 2A:
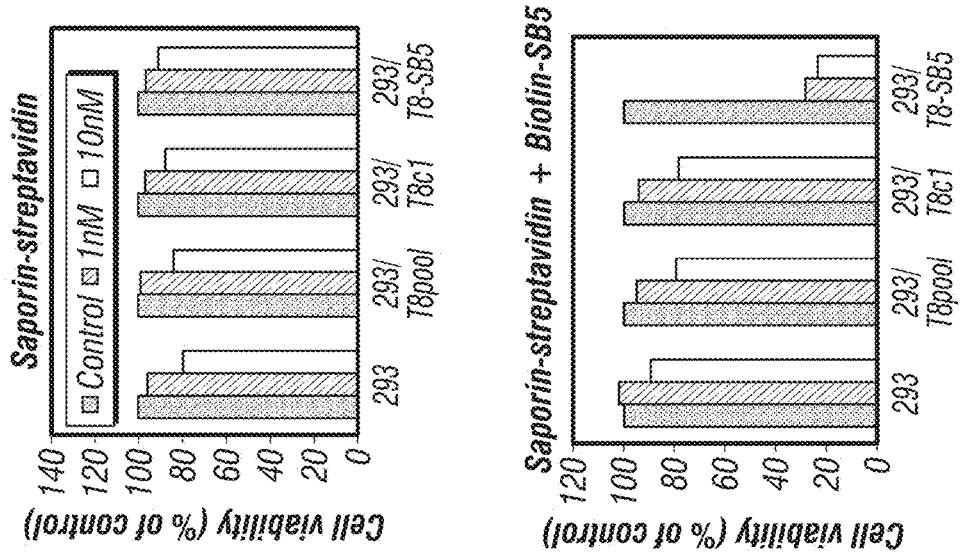

To determine if 293/T8-SB5 cells were sensitive to anti-TEM8 immunotoxin, the inventors treated cells with biotinylated SB5 antibody and streptavidin-saporin. Saporin is a type I ribosome-inactivating protein that has no known specificity in mammalian cells and can be internalized only if conjugated to an appropriate antibody. 72 hours following treatment with 1 nM of SB5-saporin toxin, viability of 293/T8-SB5 was reduced by ~70% while both 293 and 293/TEM8 cells were unaffected at this concentration (FIG. 2A). Thus, saporin-conjugated SB5 mAbs are selectively toxic to 293/T8-SB5 cells following binding and internalization.

Development of a Genetic Screen to Identify Host-Cell Factors that Regulate TEM8 Conformation. The above results suggested that the predominant form of TEM8 on the cell surface contains a masked SB5 binding site. Based on this, the inventors hypothesized that additional factors may be present in 293/TEM8 cells, which are reduced or absent from SB5-selected 293/T8-SB5 cells and are required for maintenance of TEM8 in its SB5-masked state. For example, additional TEM8 binding proteins present in 293/TEM8 cells, which could be cytosolic, membrane or extracellular, may facilitate a conformational change in TEM8 which masks the SB5 binding site. Alternatively, a membrane spanning or extracellular binding partner may interact with TEM8 and directly block the SB5 antibody/epitope interaction. To identify dominant-acting factors which can regulate SB5 binding, the inventors designed a phenotypic screen based on sensitivity of 293 cells to SB5-immunotoxins. The assay involved the transfer of a retroviral cDNA library derived from an SB5-toxin resistant (SB5-masked) cell line into a sensitive (SB5-exposed) cell line, selection with SB5-bound toxin, recovery of surviving colonies and the identification of individual cDNAs which can rescue cells from toxicity (FIG. 2B). The inventors initially considered using the parental 293/T8-SB5 cell line, or clones of this cell line, as "sensitive" recipients for infection. However, when they exposed the parental 293/T8-SB5 stable pool or multiple independent clones derived from this pool to toxin, they consistently found that a small subpopulation of the treated cells were highly resistant to the toxin (FIG. 3A).

When these rare surviving cells were expanded in culture for two weeks and then tested for TEM8 expression by flow cytometry and western blotting, TEM8 expression was near background levels (FIG. 3B). Although this result confirmed the remarkable specificity of the SB5 mAbs for TEM8, it also suggested that loss of TEM8 expression may lead to an excessive number of background colonies in our cDNA expression screen, and prompted us to explore possible mechanisms regulating the loss of TEM8 expression in SB5-toxin selected cells. Because TEM8 expression was lost in clones of 293/T8-SB5 which originated from single cells, the inventors reasoned that TEM8 expression in these surviving cells may have been silenced epigenetically, as reported for other genes (Sharma et al., 2010). To test this, the inventors treated the toxin-selected 293/T8-SB5 cells which had lost TEM8 expression with Trichostatin A (TSA), a histone deacetylase inhibitor. Indeed, TSA rescued TEM8 expression on the cell surface in a in a dose-dependent manner (FIG. 3C), suggesting that TEM8 expression is regulated by histone acetylation.

Because TSA itself demonstrated some toxicity at the concentration needed to recover full TEM8 expression, we considered using positive selection with anti-TEM8 immunomagnetic beads as an additional method to ensure the maintenance of TEM8 expression on the surface of all recipient SB5-toxin treated cells. Because each of the SB mAbs and others commercially available were unable to detect the SB5-masked form of TEM8, the inventors incorporated a 3×-FLAG tag into the N-terminus of TEM8. Immunofluorescence staining using anti-FLAG mAbs revealed FLAG-TEM8 on the cell surface of non-permeabilized 293/FlagT8 cells immediately following transfection. As expected, however, SB5 staining remained undetectable by flow cytometry, and SB5 only labeled the occasional cell by immunofluorescence staining. Next, we repeated our selection of 293/FlagT8 cells using SB5-linked magnetic beads, and then cloned the selected cells by limiting dilution. One of the clones, called 293/FlagT8-SB5, was chosen as the recipient for infection of our cDNA expression library.

To identify genes in our screen, 293/FlagT8-SB5 recipient cells were infected with a retroviral cDNA library derived from uterus, a tissue that expressed high levels of TEM8, and then treated with saporin-linked SB5 antibody along with 40 nM TSA, a concentration found in our earlier studies to be minimally-toxic to the cells. Importantly, the number of surviving colonies on each plate was 10-fold or higher in transduced versus non-transduced cells, suggesting a successful rescue by the cDNA library. After sorting cells with anti-FLAG-conjugated magnetic beads and repeating the toxin/TSA selection and sorting once more, cDNA was recovered from surviving clones and identified by DNA sequencing.

Genetic Screen Reveals Multiple Components of the Actin Cytoskeleton. A total of 99 cDNA inserts originating from 10 independent plates were recovered and sequenced, and 12 genes were identified two or more times (Table 1). Interestingly, 7 of the top 12 genes identified (~60%) are known to be directly or indirectly involved in regulation of the actin cytoskeleton. The most frequently observed genes were transgelin (TAGLN, SM22α) and alpha-smooth muscle actin (α-SMA, ACTA2), each identified 4 times from 4 independent plates. Transgelin is known to promote the cross-linking or "gelling" of actin and, similar to α-SMA, is thought to be important for contraction of smooth muscle cells (Hinz et al., 2001; Zeidan et al., 2004; Je and Sohn, 2007).

TABLE 1

Candidate genes recovered from transduced 293/FlagT8-SB5 cells following SB5-toxin treatment

| Gene | Name | Involved with actin | Plate of origin[a] |
|------|------|---------------------|---------------------|
| ACTA2 | Actin, alpha2, smooth muscle, aorta (α-SMA) | Y | 1, 2, 3, 4 |
| TAGLN | Transgelin | Y | 1, 3, 4, 8 |
| ARL1 | ADP-ribosylation factor-like 1 | N | 7, 8, 9 |
| ACTG2 | Actin, gamma 2, smooth muscle enteric | Y | 7, 10 |
| APOD | Apolipoprotein D | N | 1, 6 |
| COL6A2 | Collagen, type VI, alpha 2 | N | 6, 9 |
| GSN | Gelsolin | Y | 6, 7 |
| MYL9 | Myosin, light chain 9, regulatory | Y | 1, 4 |
| RPS6 | Ribosomal protein S5 | N | 1, 3 |
| SMARCB1 | SWI/SNF related, matrix associated, actin dependent regulator of chromatin | Y | 7, 8 |
| TPM2 | Tropomyosin 2 (beta) | Y | 5, 10 |
| TPT1 | Tumor protein, translationally controlled 1 | N | 2, 9 |

[a]Clones were isolated from 10 independent plates that were infected with virus separately.

Several of the identified genes, including smooth muscle actin and transgelin, are known to be expressed predominantly by vascular pericytes or smooth muscle cells. However, TEM8 was originally identified in a screen for genes overexpressed in tumor endothelial cells (St. Croix, 2000). To determine if smooth muscle cells also express TEM8 the inventors evaluated TEM8 mRNA expression in primary or immortalized endothelial or smooth muscle cells, and for comparison included three tumor cell lines of epithelial origin. TEM8 was found to be expressed in both vascular pericytes and endothelial cells, while expression was undetectable in the tumor cells analyzed.

Figure 4A:
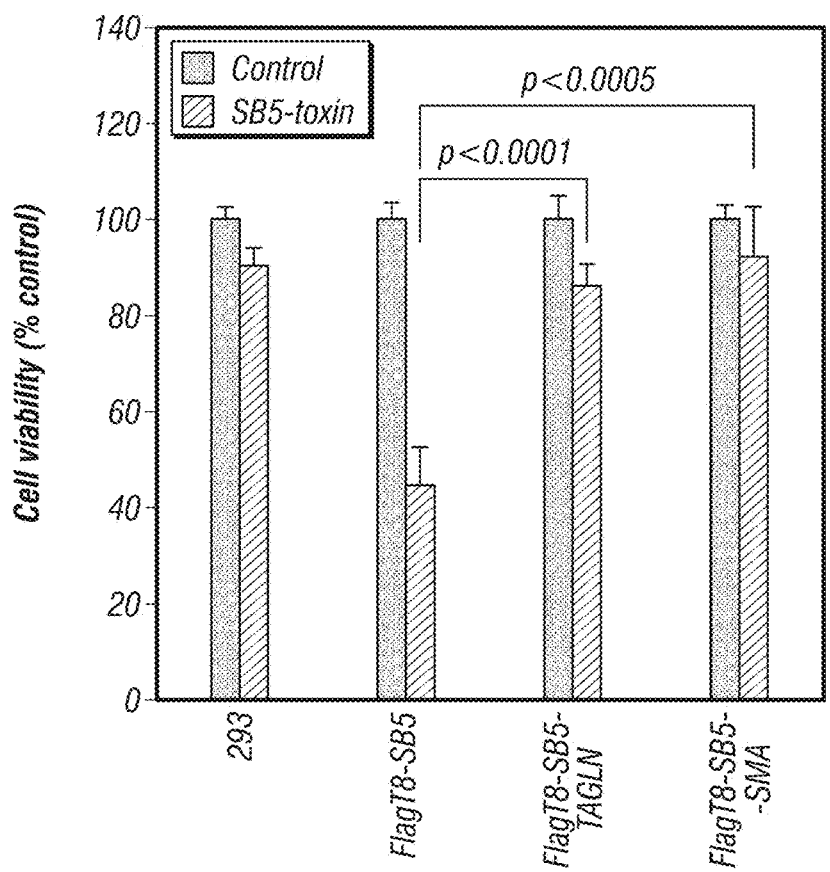
Figure 4B:
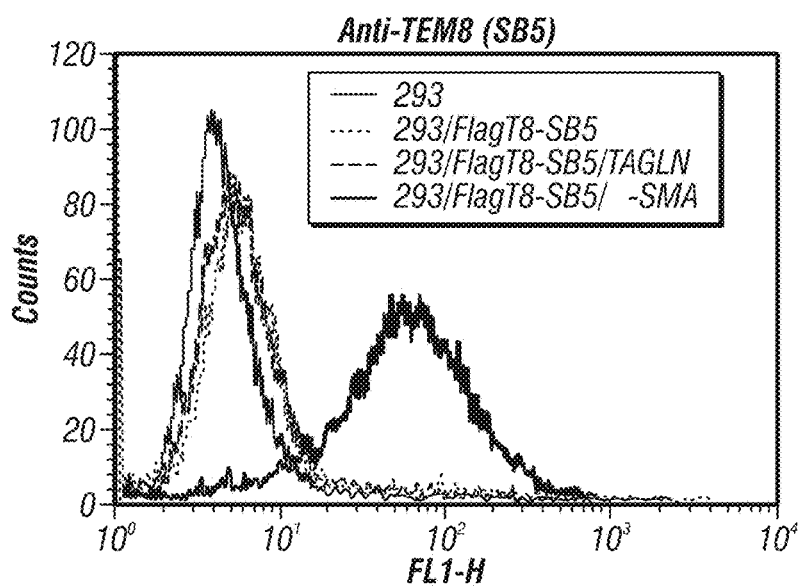
Figure 4B:
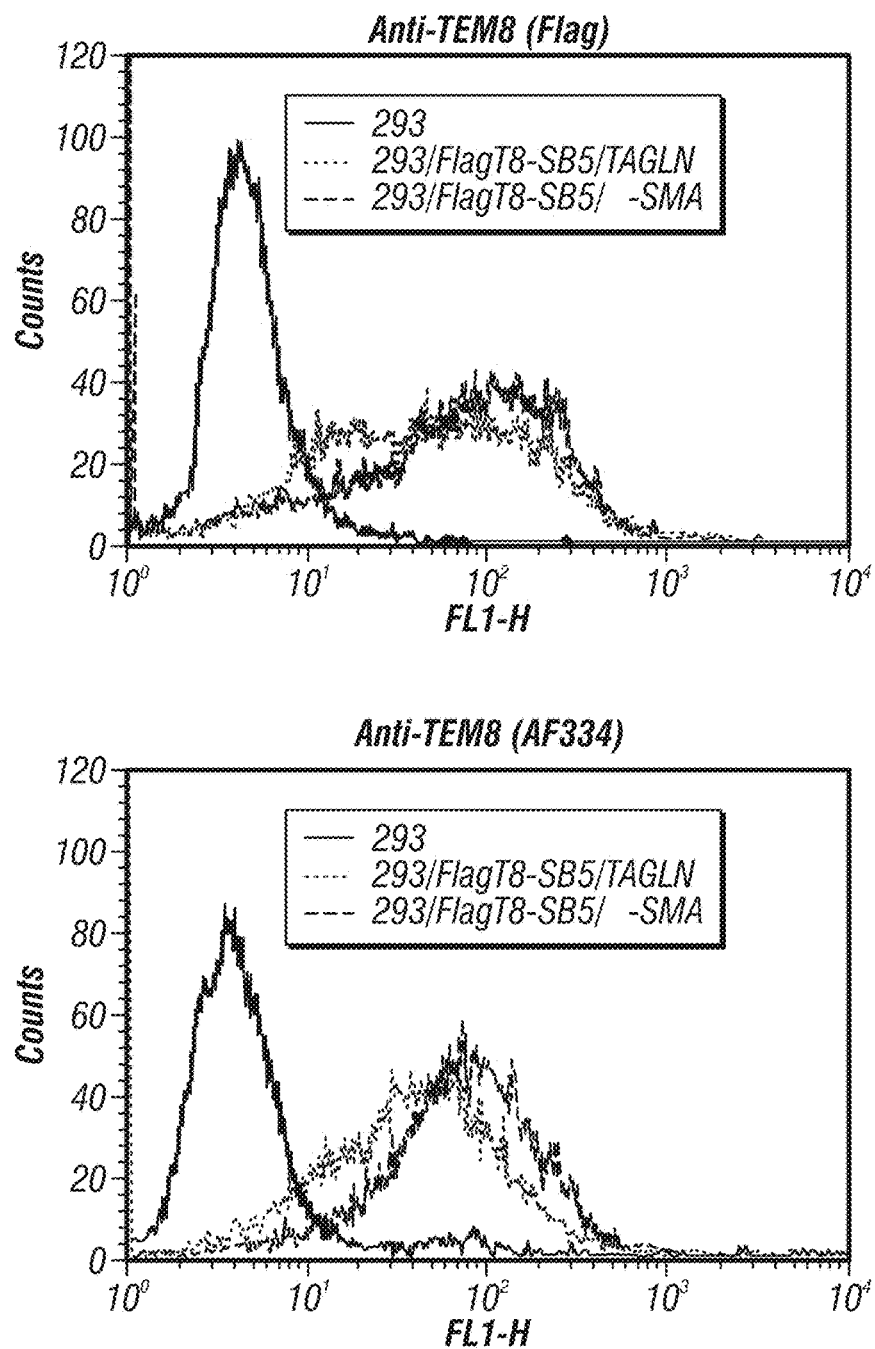

Transgelin and α-SMA Regulate TEM8 Cell Surface Structure. To determine if transgelin or α-SMA were responsible for mediating resistance to SB5-saporin, the inventors transfected these genes into 293/FlagT8-SB5 cells and then treated cells with the SB5 antibody-toxin. Importantly, at 5 nM of SB5-saporin, expression of either transgelin or α-SMA rescued 293/FlagT8-SB5 cells from toxicity (FIG. 4A). An analysis of SB5 binding by flow cytometry revealed that SB5 was unable to bind TEM8 on the surface of transgelin- or α-SMA-transfected 293/FlagT8-SB5 cells, even though the non-transfected 293/FlagT8-SB5 cells labeled strongly (FIG. 4B). Importantly, however, TEM8 expression remained high in transgelin or □-SMA transfected 293/FlagT8-SB5 cells by immunoblotting, and staining of cells with anti-FLAG mAbs by flow cytometry verified the expression of TEM8 on the cell surface of 293/FlagT8-SB5-TAGLN or 293/FlagT8-SB5-SMA cells (FIG. 4B). These results suggest that an alteration in the structure of TEM8 at the cell surface is responsible for masking the SB5 epitope.

Next, we set out to determine if an alteration in TEM8 structure could be the consequence of a direct interaction between TEM8 and α-SMA or transgelin. Indeed, TEM8 co-immunoprecipitated with α-SMA and these proteins were also found to co-localize at the cell surface by immunofluorescence staining. Although we have not yet been able to co-immunoprecipitate transgelin and TEM8, this could be due to a limitation of the mAbs currently available. Alternatively, TEM8 may bind transgelin indirectly.

Because the SB5-exposed form of TEM8 was derived from a cryptic population and was only observed on the majority of cells following cell surface enrichment with SB5-beads, these studies indicate that an SB5-masked form of TEM8 is generally present on the cell surface of TEM8-positive cells. To determine if the predominant SB5-masked form of TEM8 could also be internalized upon antibody binding, similar to the SB5-exposed form, we treated non-selected 293/FlagT8 cells with saporin-bound anti-FLAG antibodies. Saporin-anti-FLAG antibodies were selectively toxic to 293/FlagT8 cells compared to parental 293 cells suggesting that antibodies which can recognize the predominant SB5-masked form of TEM8 on the cell surface can also be internalized effectively.

Figure 5:
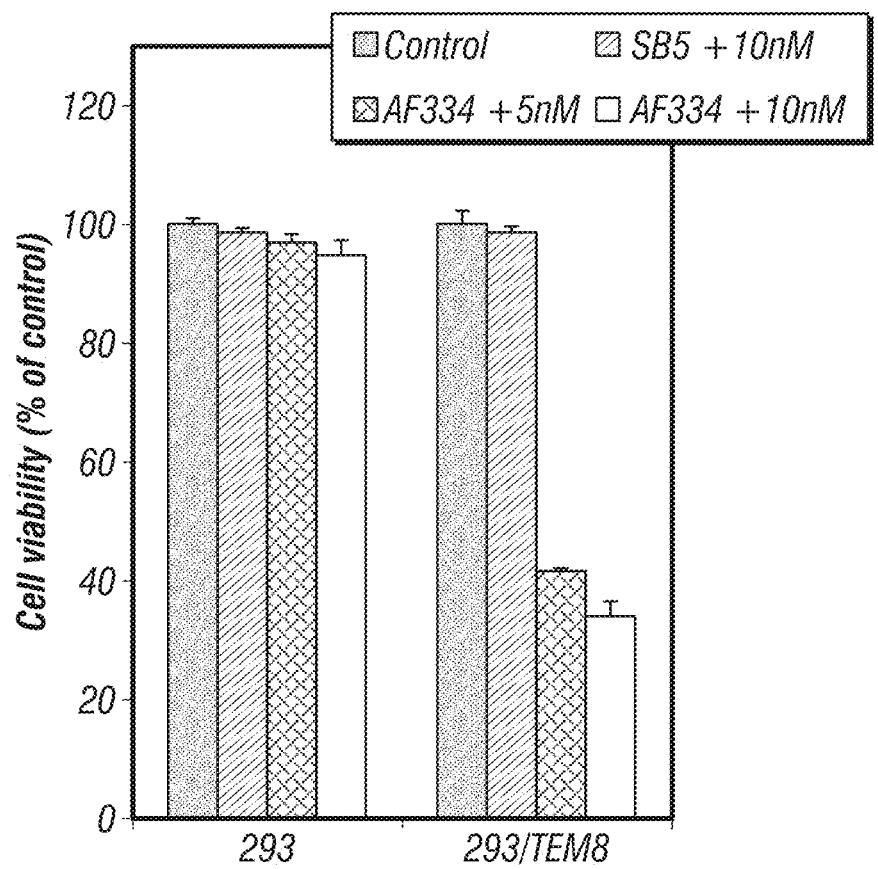

Development of an Antibody that Recognizes the SB5-Masked Form of TEM8. Encouraged by these results, the inventors set out to develop a new monoclonal antibody which can recognize the predominant SB5-masked form of TEM8. Rather that using recombinant TEM8 protein as the immunogen, this time they employed an alternative method for antibody generation based on immunization of mice with TEM8-expressing cells followed by flow cytometry-based screening (see Example 1—Materials and Methods for details). Using this strategy, a monoclonal antibody, called AF334, was identified that, like SB5, was able to bind both mouse and human TEM8 by flow cytometry. AF334 was also able to bind the SB5-exposed form of TEM8 on the surface of SB5-selected 293/hT8-SB5 cells. Importantly, however, AF334 differed from previously developed anti-TEM8 antibodies in that it also reacted strongly with the predominant SB5-masked form of TEM8 on the cell surface (FIG. 1C). Next, the inventors treated cells expressing the SB5-masked form of TEM8 with an AF334-saporin immunotoxin. Unlike SB5, AF334 was toxic towards 293/TEM8 cells but not 293 cells (FIG. 5), demonstrating the ability of this antibody to selectively deliver toxin into cells expressing the predominant SB5-masked form of TEM8. The hybridoma cell line for AF334 was deposited with ATCC (ATCC Patent Deposit Designation PTA-11454).

Example 3

Antibody (AF334) Sequence Information

VL (AF334)-SEQ ID NO: 1:
DIVMTQTPPSVPVTPGESVSISCRSSKSLLHSNGNTYLYWF
LQRPGQSPQLLIYRMSNLASGVPDRFSGSGSGTAFTLRISR
VEAEDVGVYYCMQHLEYPFTFGSGTKLEIKRA

SEQ ID NO: 19: nucleic acid sequence encoding VL (AF334):
Gacattgtgatgacccagactccaccctctgtacctgtcac tcctggagagtcagtatccatctcctgcaggtctagtaaga gtctcctgcatagtaatggcaacacttacttgtattggttc ctgcagaggccaggccagtctcctcagctcctgatatatcg gatgtccaaccttgcctcaggagtcccagacaggttcagtg -continued

```
gcagtgggtcaggaactgctttcacactgagaatcagtaga gtggaggctgaggatgtgggtgtttattactgtatgcaaca tctagaatatccattcacgttcggctcggggacaaagttgg aaataaaacgggct
```

VH (AF334)-SEQ ID NO: 2:
QVKLEESGAELVRPGVSVKISCKGSGYTFTDYAMHWVKQSH
AKSLEWIGVISTYFGDATYNQKFKGKATMTVDKSSSTAYME
LARLTSEDSAIYYCAREDYVPFAYWGQGTLVTVSA

SEQ ID NO: 20: nucleic acid sequence
encoding VH (AF334):
```
Caggttaagctggaggagtcaggggctgagctggtgaggcc tggggtctcagtgaagatttcctgcaagggttctggctaca cattcactgattatgctatgcactgggtgaagcagagtcat gcaaagagtctagagtggattggagttattagtacttactt tggtgatgctacctacaaccagaagttcaagggcaaggcca caatgactgtagacaaatcctccagcacagcctatatggaa cttgccagactgacatctgaggattctgccatctattactg tgcaagagaggattacgtcccgtttgcttactggggccaag ggactctggtcactgtctctgca
```

The primers used for cloning AF334 VL and VH by PCR. MH1 and MH2 are described below. Heavy chain frame region primers were used. Also, IgM is heavy chain constant region primer; Kc is primer for cloning mouse kappa chain constant region; Mk is mouse kappa chain frame region universal primer.
Primers:

MH1:
                                             (SEQ ID NO: 24)
5' ctt ccg gaa ttc SAR GTN MAG CTG SAG SAG TC-3'

MH2:
                                             (SEQ ID NO: 25)
5X-ctt ccg gaa ttc SAR GTN MAG CTG SAG SAG TCW GG-3'

IgM:
                                             (SEQ ID NO: 26)
5X-gga aga tct GAC ATT TGG GAA GGA CTG ACT CTC-3'

Kc:
                                             (SEQ ID NO: 27)
5X-ggt gca tgc GGA TAC AGT TGG TGC AGC ATC-3'

Mk:
                                             (SEQ ID NO: 28)
5X-gg gag ctc GAY ATT GTG MTS ACM CAR WCT MCA-3'

See Wang et al., *J. Immunol. Meth.* 223 (200) 167-177, 2000, which is hereby incorporated by reference.

Example 4

Binding of cAF334 to the Extra Cellular Domain of TEM8

Figure 9A:
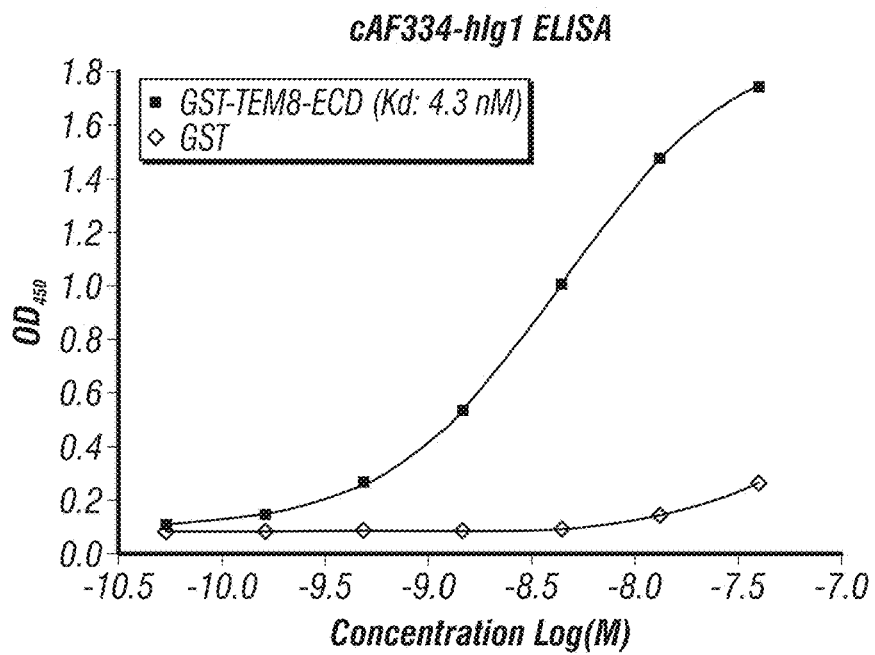
Figure 9B:
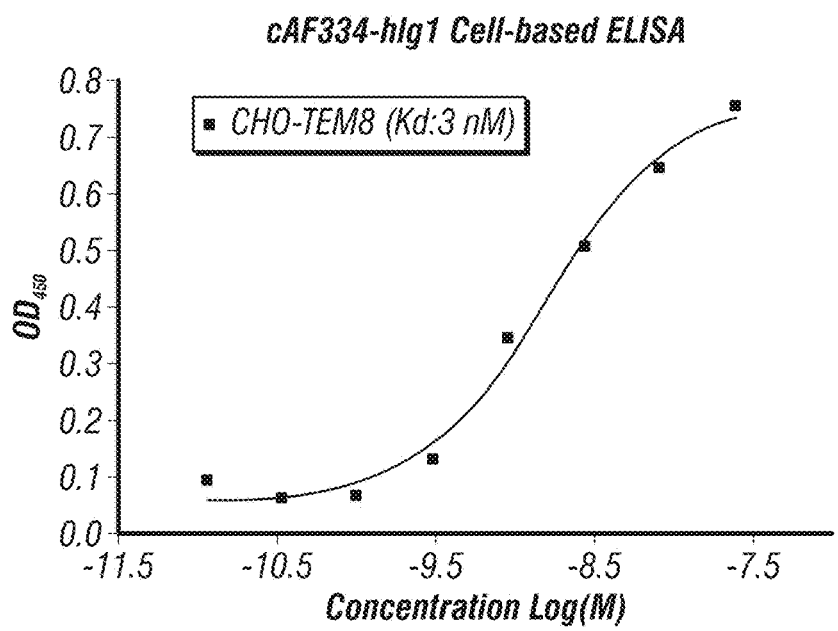
Figure 10B:
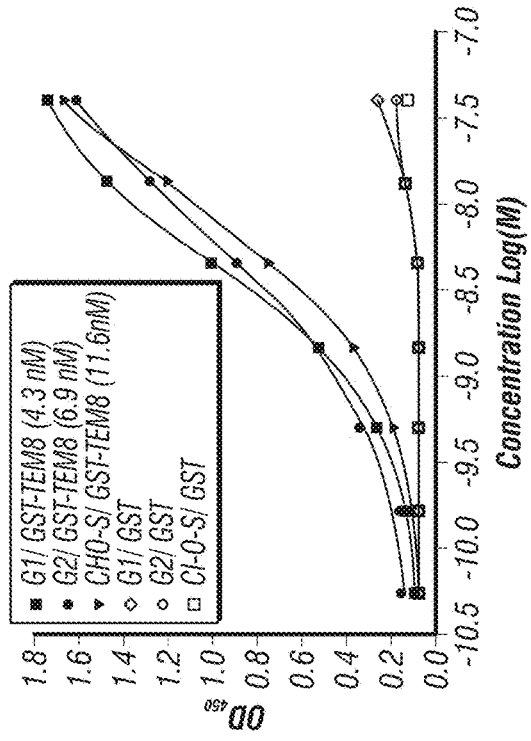
FIG. 10A-B. Binding of cAF334 to GST-TEM8-ECD.
Figure 10A:
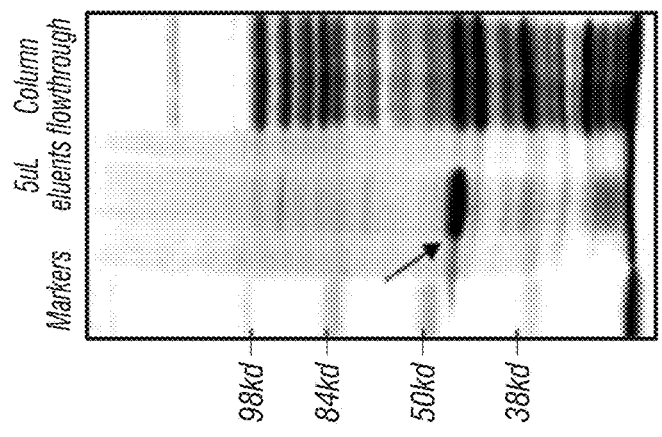
Figures 11A, 11B:
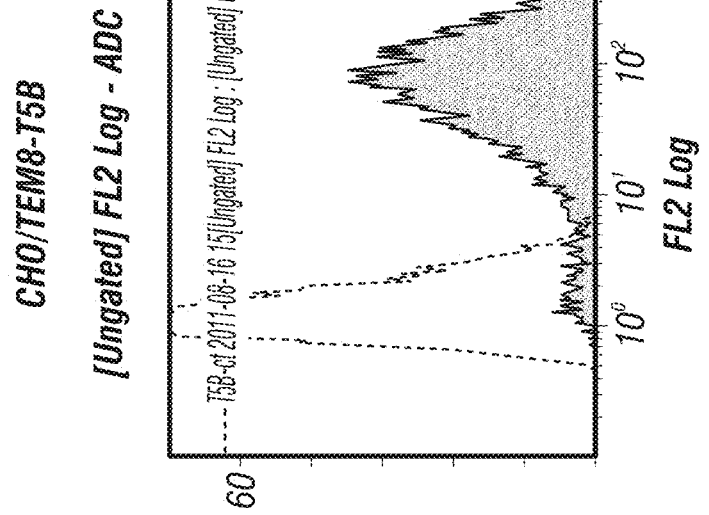
FIG. 11A-B. Results of Flow Cytometry. Binding of purified cAF334-hIg1 to cell surface TEM8 was analyzed by flow cytometry with (A) parental CHO/PR230 cells; and (B) CHO/PR230 transfected with TEM8 expression plasmid. This TEM8 transfected CHO/PR230 cells (clone T5B) were selected for high levels of cell surface TEM8. Briefly, monolayer cultured cells were harvested and pre-blocked by 3% normal goat serum, and incubated with 20 mcg/ml of cAF334-hIg at 4° C. for 1 hour. PE-conjugated goat-anti-human Fc antibody (1/100 dilution) was used as the secondary antibody.

Binding of cAF334 to the extra-cellular domain (ECD) of TEM8 was evaluated in two assays: enzyme-linked immunosorbent assay (ELISA) and cell-based ELISA. FIG. 9A depicts results of the ELISA: GST-TEM8-ECD fusion proteins expressed in and purified from bacterial overexpression system were used to coat 96-well glutathione plates. A serial dilution of purified cAF334 (G1 batch) was then added into each well of the plates. The bound cAF334 was detected by horse radish peroxidase (HRP)-conjugated goat anti-human antibodies and HRP substrates. The binding affinity (Kd) was measured at 4.3 nM. FIG. 9B depicts results of a cell-based ELISA: CHO cells overexpressing full-length TEM8 on the cell surface (clone T5B) were cultured in 96-well plates ($5 \times 10^4$ cells/well) at 37° C./5% $CO_2$ incubator for overnight. Cells were fixed by 3% formaldehyde at room temperature for 10 minutes. These non-permeablized cells were blocked by 10% normal goat serum at room temperature for 30 minutes. The addition of cAF334 antibodies and detection are identical to ELISA protocol in (A). The binding affinity (Kd) was measured at 3 nM.

Example 5

Additional Studies on cAF334

Eight additional experiments were performed as described in this section. In summary, these studies show that the cAF334 antibody binds with high affinity to a specific epitope on the extracellular domain of TEM8 that is highly conserved from mouse to man. Further, the antibody triggers internalization of TEM8 to early endosomes from which diphtheria toxin and monomethylauristatin is able to reach the cytosol. Further, the antibody drug conjugate binds and is cytotoxic to the neuroblastoma cell line IMR-32. This cell line was derived from a child with MYCN amplification and poor-risk disease.

With a distinct anti-TEM8 antibody, TEM8 expression has been demonstrated on colorectal carcinoma, breast carcinoma, lung carcinoma, and melanoma as well as neuroblastoma. In these studies, different anti-TEM8 antibody or control mouse immunoglobulin was incubated at 10 ug/mL for 30 minutes at 4 degrees C. with cells, washed and detected with FITC-rabbit anti-mouse immunoglobulin, and applied to a flow cytometer. These results indicate that TEM8 is expressed on a number of tumor types.

The lysyl oxidase protein is associated with highly metastatic cancers and induces TEM8 expression on endothelial and epithelial carcinoma cells. HUVEC lysate immunoblots reacted with polyclonal anti-TEM8 or polyclonal b-actin after addition of conditioned collected from colorectal cancer cells. SW480 are non-metastatic and have low LOX and low angiogenesis. SW480+LOX are metastatic, have high LOX+angiogenesis. SW620 are metastatic (isolated from same patient) and have high LOX+angiogenesis. SW620shLOX are non-metastatic, have low LOX+angiogenesis.

Biacore experiments confirmed that cAF334 binds to the human TEM8 extracellular domain (ECD) with a $K_D$ of 7 nM (FIG. 12). cAF334 bound to a Biacore chip and flow included different concentrations of TEM8 ECD-GST. Bound mass was detected as response (RU).

Figures 12, 13:
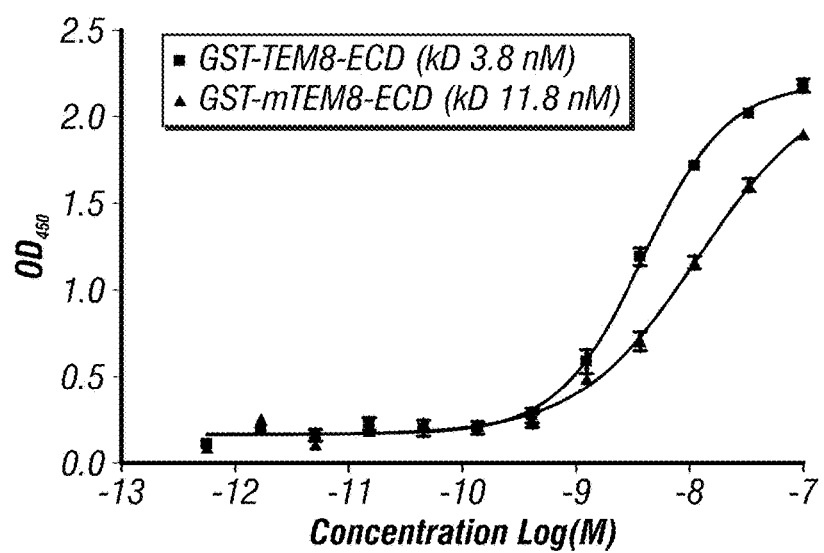
FIG. 12. Biacore experiments confirm cAF334 binding to human TEM8 extracellular domain (ECD) with $K_D$ of 7 nM. cAF334 bound to Biacore chip and flow included different concentrations of TEM8 ECD-GST. Bound mass is detected as response (RU).
FIG. 13. ELISA reactivity of cAF334 with human and mouse TEM8 ECD. 96-well GSH plate coated with 100 ng/well of GST-TEM8-ECD or GST-mTEM8-ECD. A serial dilution of cAF334 was added to each well and incubated at room temperature for 1 hour. Anti-GST antibody and HRP-conjugated anti-mouse antibody were used for detection.

FIG. 13 depicts ELISA reactivity of cAF334 with human and mouse TEM8 ECD. 96-well GSH plates were coated with 100 ng/well of GST-TEM8-ECD or GST-mTEM8-ECD. A serial dilution of cAF334 was added to each well and incubated at room temperature for 1 hour. Anti-GST antibody and HRP-conjugated anti-mouse antibody were used for detection.

Figure 14:
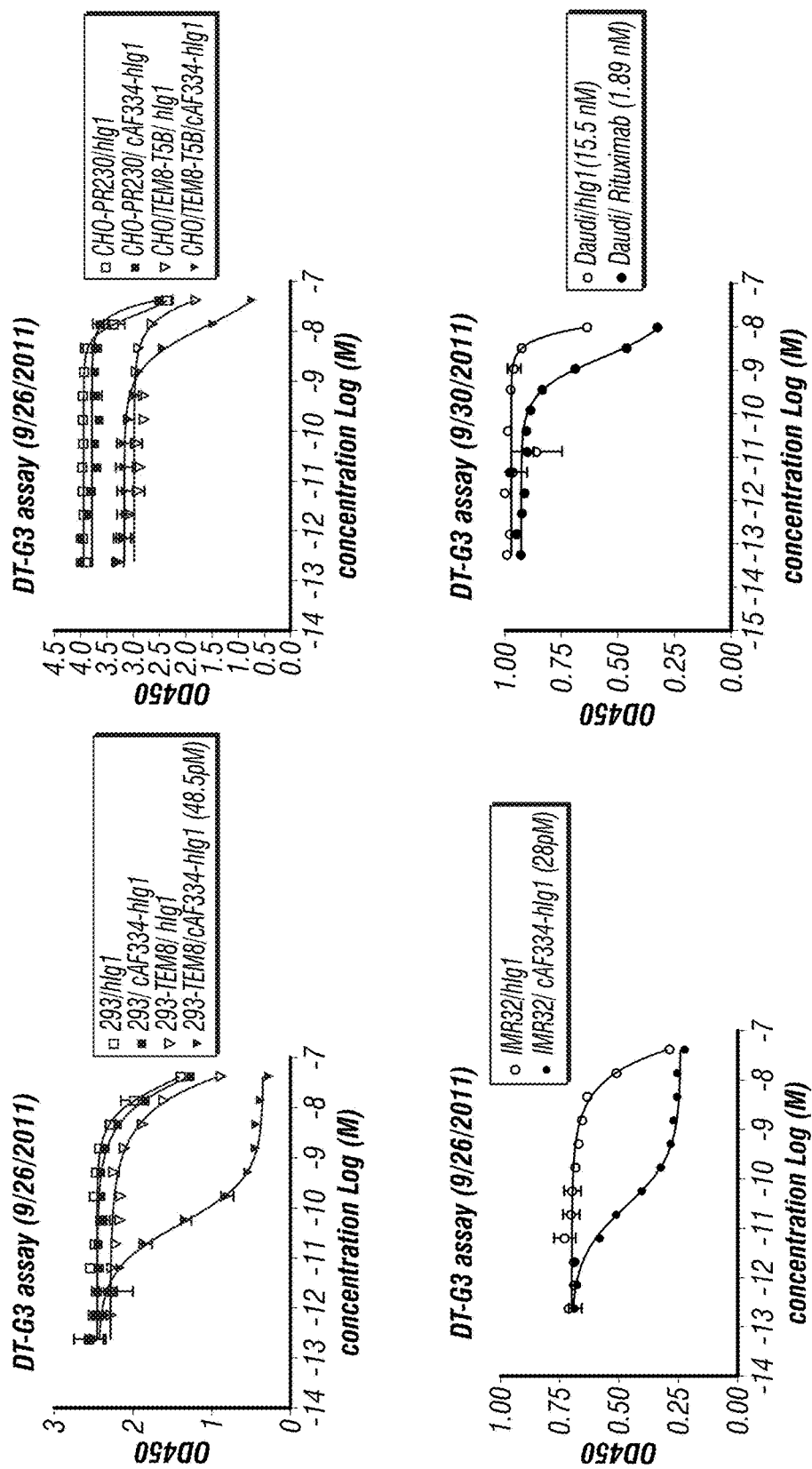
FIG. 14. Cytotoxicity assays with DTG3-conjugated cAF334 and Rituximab confirm antibody internalization and toxin potency.

FIG. 14 depicts results of cytotoxicity assays with DTG3-conjugated cAF334 and Rituximab which confirmed antibody internalization and toxin potency. Mixtures of DTG3 and antibody (cAF334, rituximab, or human IgG1) with a molar ratio of 2:1 were incubated at room temperature for 1 hour before the addition of 20 mM dimethyl-pimelimidate (DMP) for 10 minutes. Unused DMP were neutralized by Tris-HCl pH8.0. In these assays, mixtures were diluted 1:5 into culture medium in the first well of a dilution 96-well plate and a serial of 1:3 dilutions was made for each cell line. 50 ml of diluted antibodies were added into each well with $1\times10^4$ cells and incubate in a 37 degrees C./5% CO2 incubator for ~66 hours. 10 ml of CCK-8 cell counting dye were added into each well and continue incubation at 37 degrees C. for another 4 hours. OD450 was measured and plotted into curves with Prism software.

Figures 15, 16:
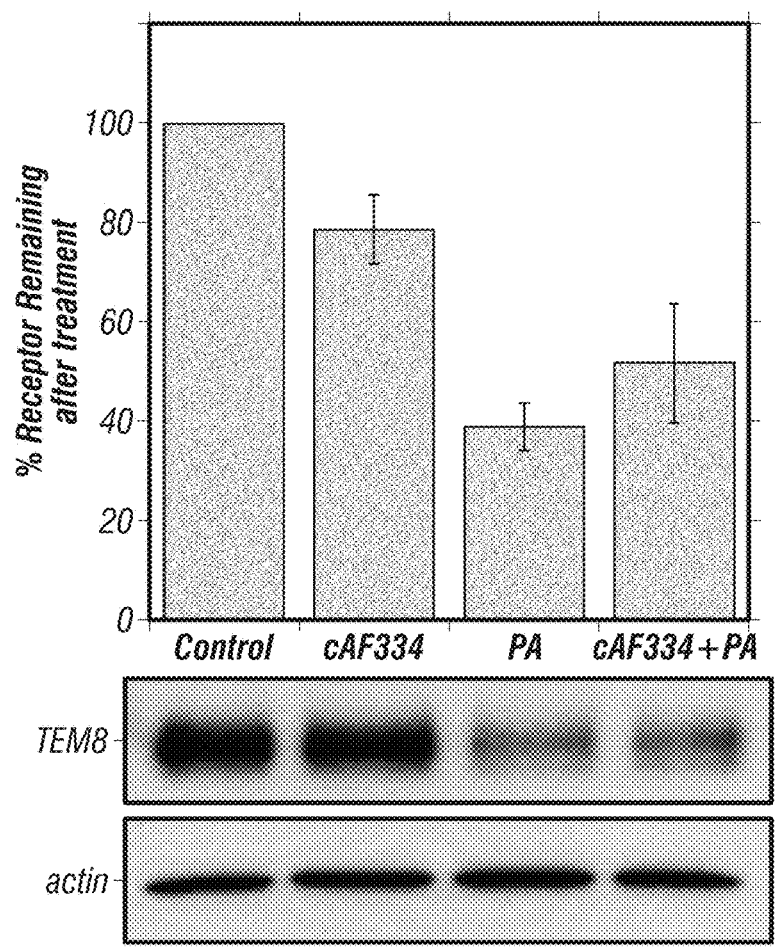
FIG. 15. TEM8-MMAE conjugates confirm selective cytotoxicity and potency of cAF334 antibody drug conjugates.
FIG. 16. TEM8 internalizes to early endosomes.

TEM8-MMAE conjugates confirmed the selective cytotoxicity and potency of cAF334 antibody-drug conjugates (FIG. 15). Incubation with ADC for 84 h then addition 1 µCi 3H-thymidine for 12 h and then harvested and counted. IC50 is concentration ADC producing 50% inhibition of 3H-thymidine incorporation relative to control. Quadruplicate samples were done.

Further studies demonstrated that TEM8 internalizes to early endosomes. The antibody cAF334 is internalized: TEM8 expressing Hek293 were incubated for 1 h with 1 ug/ml cAF344 in HBSS for 1 h at 4 degrees C. Excess antibody was washed and cells were fixed immediately or after 45 minutes at 37 degrees C. Staining for cAF334 using a goat anti-human polyclonal antibody and for TEM8 reveal surface co-localization at 4 degrees C. and in intracellular compartments after the 37 degrees C. incubation.

In other studies, staining for TEM8, cAF334 and Lamp-1 was used to evaluate localization of these proteins in late endosomes. The presence of cAF334 did not significantly increase localization of TEM8 in late endosomes after 45 minutes, which suggests that the antibody does not induce receptor degradation. The low levels of cAF334 and Lamp-1 colocalization indicates that antibody cAF344 accumulates in an intracellular compartment different from Lamp-1 positive late endosomes.

FIG. 16 shows that TEM8 internalizes to early endosomes. Permanently TEM8 expressing Hek293 cells were incubated for 6 hours with 10 ug/ml of cycloheximide and in the absence or presence of 1 ug/ml cAF334 or 1 ug/ml Protective Antigen. TEM8 levels were evaluated in cell lysates by western blot. The average of 2 experiments is shown in FIG. 16. This experiment shows that cAF344 does not promote significant receptor degradation, being less efficient than Protective Antigen. This result correlates with microscopy findings.

The antibody cAF344 was found to accumulate in transferrin receptor positive intracellular compartments: Non transfected or TEM8 expressing Hek293 cells were incubated for 1 h with 1 ug/ml cAF334 at 4° C. Excess antibody was washed and cells were shifted for 45 min at 37° C. as before. Immunofluorescence staining for the antibody, TEM8 and transferin receptor showed partial co-localization of the internalized antibody with transferin receptor. The presence of the antibody did not affect but rather seemed to increase the co-localization of TEM8 with transferin.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. References

The following references, to the extent that they provide exemplary procedural or other details supplementary to those set forth herein, are specifically incorporated herein by reference.

U.S. Pat. No. 4,472,509
U.S. Pat. No. 4,938,948
U.S. Pat. No. 5,196,066
U.S. Patent Publn. 20070117802
U.S. Patent Publn. 20070123534
U.S. Patent Publn. 20070179130
U.S. Patent Publn. 20070203136
U.S. Patent Publn. 20070213319
U.S. Patent Publn. 20080058312
Abi-Habib et al., *Clin. Cancer Res.*, 12:7437-7443, 2006.
Abrami et al., *J. Cell Biol.*, 160:321-328, 2003.
Atherton et al., *Biol. of Reproduction*, 32, 155-171, 1985.
Bell et al., *J. Cell Sci.*, 114:2755-2773, 2001.
Bradley et al., *Nature*, 414:225-229, 2001.
Burbage et al., *Leuk Res.*, 21(7):681-690, 1997.
Carson-Walter et al., *Cancer Res.*, 61:6649-6655, 2001.
Chen, et al., *J Biol Chem*, 282:9834-9845, 2007.
Cullen et al., *Cancer Res.*, 69:6021-6026, 2009.
De Jager et al., *Semin. Nucl. Med.* 23(2), 165-179, 1993.
Dholakia et al., *J. Biol. Chem.*, 264, 20638-20642, 1989.
Duan et al., *J. Natl. Cancer Inst.*, 99:1551-1555, 2007.
Duesbery et al., *Proc. Natl. Acad. Sci. USA*, 98:4089-4094, 2001.
Frankel et al., *J. Biol. Response Mod.*, 4:273-286, 1985.
Go et al., *Infect. Immun.*, 77:52-59, 2009.
Gulbis and Galand, *Hum. Pathol.* 24(12), 1271-1285, 1993.
Higa and Abraham, *Expert Rev. Anticancer Ther.*, 9:999-1007, 2009.
Hinz et al., *Mol. Biol. Cell*, 12:2730-2741, 2001.
Hotchkiss et al., *Exp. Cell Res.*, 305:133-144, 2005.
Je and Sohn, *Mol. Cells*, 23:175-181, 2007.
Khatoon et al., *Ann. of Neurology*, 26, 210-219, 1989.
King et al., *J. Biol. Chem.*, 269, 10210-10218, 1989.
Lidor et al., *Am. J. Obstet. Gynecol.*, 177(3):579-585, 1997.
Liu et al., *J. Biol. Chem.*, 283:529-540, 2008.
Liu et al., *Proc. Natl. Acad. Sci. USA*, 100:657-662, 2003.
Massuda et al., *Proc. Natl. Acad. Sci. USA*, 94(26):14701-14706, 1997.
Nakamura et al., In: *Enzyme Immunoassays: Heterogeneous and Homogeneous Systems*, Chapter 27, 1987.
Nanda et al., *Cancer Res.*, 64:817-820, 2004.
O'Shannessy et al., *J. Immun. Meth.*, 99, 153-161, 1987.
Owens and Haley, *J. Biol. Chem.*, 259, 14843-14848, 1987.
Posner et al., *Hybridoma.*, 6, 611-625, 1987.
Potter and Haley, *Meth. Enzymol.*, 91, 613-633, 1983.
Remington: The Science and Practice of Pharmacy 20th Ed., 2000.
Rouleau et al., *Int. J. Oncol.*, 32:739-748, 2008.
Ruan et al., *J. Immunother.*, 32:486-491, 2009.
Scobie et al., *Proc. Natl. Acad. Sci. USA*, 100:5170-5174, 2003.
Sharma et al., *Cell*, 141:69-80, 2010.
Singh et al., *Infect. Immun.*, 67:1853-1859, 1999.
St Croix et al., *Science*, 289:1197-1202, 2000.
Vitetta et al., *Science*, 238:1098, 1987.
Wang et al., *J. Immunol. Meth.* 223 (200) 167-177, 2000.
Watson et al., *PLoS One*, 2:e466, 2007.
Werner et al., *J. Biol. Chem.*, 281:23227-23236, 2006.
Zeidan et al., *FEBS Lett.*, 562:141-146, 2004.

What is claimed is:

1. A method of treating a subject with a vascularized tumor comprising administering to said subject an antibody or antibody fragment that binds immunologically to native cell-surface expressed Tumor Endothelial Marker 8 (TEM8), wherein the antibody or antibody fragment comprises the amino acid sequences of SEQ ID NO:45 (CDR1), SEQ ID NO:46 (CDR2), and SEQ ID NO:47 (CDR3) of a heavy chain variable region and amino acid sequences of SEQ ID NO:48 (CDR4), SEQ ID NO:49 (CDR5), and SEQ ID NO:50 (CDR6) of a light chain variable region.

2. The method of claim 1, wherein said antibody is an IgG antibody.

3. The method of claim 1, wherein said antibody or antibody fragment is humanized.

4. The method of claim 1, wherein said antibody is a single chain antibody.

5. The method of claim 1, wherein said antibody or antibody fragment is a bivalent antibody or antibody fragment.

6. The method of claim 1, wherein said antibody fragment is Fab' or F(ab')$_2$.

7. The method of claim 1, wherein said antibody or antibody fragment is conjugated to a therapeutic agent.

8. The method of claim 7, wherein said therapeutic agent is a chemotherapeutic, a radiotherapeutic or a toxin.

9. The method of claim 1, wherein said antibody or antibody fragment comprises a light chain variable region sequence of SEQ ID NO: 1 and a heavy chain variable region sequence of SEQ ID NO:2.

10. The method of claim 1, wherein the vascularized tumor is a brain tumor, an ocular tumor, a head & neck tumor, a skin tumor, a lung tumor, an esophageal tumor, a pancreatic tumor, a stomach tumor, a liver tumor, a prostate tumor, a colon tumor, a rectal tumor, a breast tumor, an ovarian tumor, a uterine tumor, a cervical tumor, a lymphoma, or a testicular tumor.

11. The method of claim 1, wherein said subject has recurrent cancer, metastatic cancer or multi-drug resistant cancer.

12. The method of claim 1, wherein said antibody or antibody fragment is administered systemically, regionally to the tumor, or local to the tumor.

13. The method of claim 1, wherein said antibody or antibody fragment is administered via intratumoral injection, injection into the tumor vasculature or into a resected tumor bed.

14. The method of claim 1, wherein said antibody or antibody fragment is administered to said subject at least two, three, four, five, six, seven, eight, nine or ten times.

15. The method of claim 1, wherein said subject is further administered a distinct cancer therapy.

16. The method of claim 15, wherein said distinct cancer therapy comprises surgery, radiotherapy, chemotherapy, toxin therapy, immunotherapy, cryotherapy or gene therapy.

17. The method of claim 15, wherein said distinct cancer therapy is administered at the same time as said antibody or antibody fragment.

18. The method of claim 15, wherein said distinct cancer therapy is administered prior to said antibody or antibody fragment.

19. The method of claim 15, wherein said distinct cancer therapy is administered after said antibody or antibody fragment.

20. The method of claim 1, further comprising detecting TEM8 expression on the cells of the subject prior to administering the antibody.

21. The method of claim 1, wherein said antibody or antibody conjugate is conjugated to a drug by a linker, and wherein said conjugate is a conjugate of formula VI:

$$Ab(L-D)p \qquad \text{formula VI}$$

or a pharmaceutically acceptable salt or solvate thereof, wherein Ab is an antibody or antibody fragment that binds immunologically to native cell-surface expressed TEM8, L is a linker unit, D is a drug unit, and p ranges from 1 to about 20.

22. The method of claim 1, wherein said antibody or antibody fragment is conjugated to a detectable label.

23. The method of claim 22, wherein the detectable label is colorimetric, fluorescent, enzymatic, or radioactive.

* * * * *

UNITED STATES PATENT AND TRADEMARK OFFICE
CERTIFICATE OF CORRECTION

PATENT NO. : 10,273,299 B2  
APPLICATION NO. : 15/090058  
DATED : April 30, 2019  
INVENTOR(S) : Frankel et al.

Page 1 of 1

It is certified that error appears in the above-identified patent and that said Letters Patent is hereby corrected as shown below:

On the Title Page

Item (73), after The United States of America, as Represented by the Secretary, Department of Health and Human Services, Washington, DC (US) please add --Scott & White Healthcare, Temple, TX (US); Wake Forest University Health Sciences, Winston-Salem, NC (US)--.

Signed and Sealed this  
Eleventh Day of April, 2023

Katherine Kelly Vidal  
*Director of the United States Patent and Trademark Office*